(12) United States Patent
Yeaman et al.

(10) Patent No.: US 9,133,257 B2
(45) Date of Patent: *Sep. 15, 2015

(54) ANTIMICROBIAL PEPTIDES AND DERIVED METAPEPTIDES

(71) Applicant: Los Angeles Biomedical Research Institute at Harbor-UCLA Medical Center, Torrance, CA (US)

(72) Inventors: Michael R. Yeaman, Redondo Beach, CA (US); Alexander J. Shen, Torrance, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/770,924

(22) Filed: Feb. 19, 2013

(65) Prior Publication Data

US 2013/0244928 A1 Sep. 19, 2013

Related U.S. Application Data

(63) Continuation of application No. 12/911,693, filed on Oct. 25, 2010, now Pat. No. 8,440,792, which is a continuation of application No. 09/648,816, filed on Aug. 25, 2000, now Pat. No. 7,820,619, which is a continuation-in-part of application No. 09/622,561, filed as application No. PCT/US99/03350 on Feb. 17, 1999, now abandoned, which is a continuation-in-part of application No. 09/025,319, filed on Feb. 18, 1998, now abandoned.

(51) Int. Cl.
C07K 14/47 (2006.01)
C07K 7/06 (2006.01)
C07K 7/08 (2006.01)
A61K 38/00 (2006.01)

(52) U.S. Cl.
CPC . *C07K 14/47* (2013.01); *C07K 7/06* (2013.01); *C07K 7/08* (2013.01); *C07K 14/4723* (2013.01); *A61K 38/00* (2013.01)

(58) Field of Classification Search
CPC ................................. C07K 14/47; C07K 7/08
USPC ................................................... 514/2.4, 3.3
See application file for complete search history.

(56) References Cited

U.S. PATENT DOCUMENTS 6,743,769 B1 * 6/2004 Yeaman et al. ................ 514/2.3

* cited by examiner

*Primary Examiner* — Anand Desai
(74) *Attorney, Agent, or Firm* — Sheppard Mullin Richter & Hampton

(57) ABSTRACT

The peptides and derivative metapeptides based upon natural antimicrobial peptides have potent and broad spectrum activity against pathogens exhibiting multiple antibiotic resistance. Specific peptides can also potentiate the antimicrobial functions of leukocytes, such as neutrophils. In addition, they exhibit lower inherent mammalian cell toxicities than conventional antimicrobial peptides, and overcome problems of toxicity, immunogenicity, and shortness of duration of effectiveness due to biodegradation, retaining activity in plasma and serum. The peptides and derivative metapeptides exhibit rapid microbicidal activities in vitro, can be used to potentiate conventional antimicrobial agents, to potentiate other antimicrobial peptides and are active against many organisms that exhibit resistance to multiple antibiotics currently in existence.

15 Claims, 25 Drawing Sheets

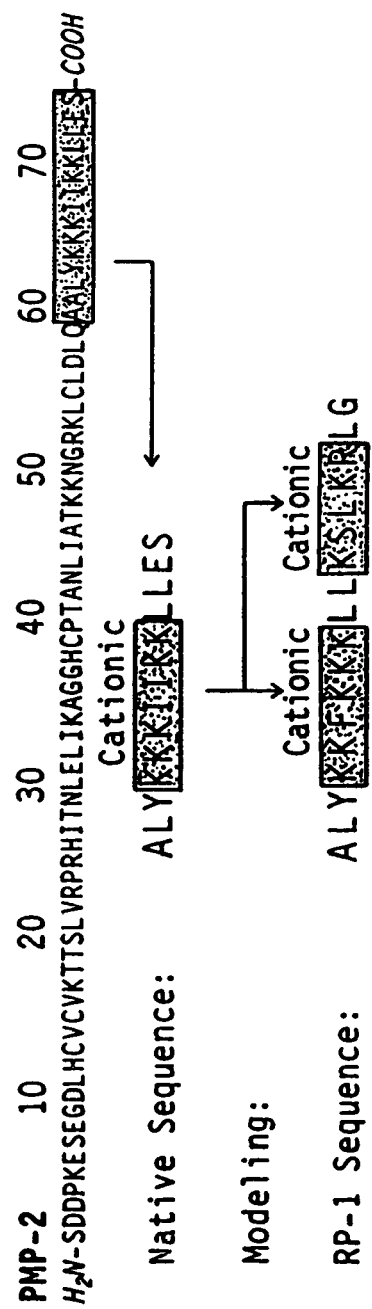

FIG. 12

| PMP-2 RESIDUE: | Sequence | MW (Da) |
|---|---|---|
| 1-74 | H₂N-SDDPKESEGDLHCVCVKTTSLVRPRHITNLELIKAGGHCPTANLIATKKNGRKLCLDLQAALYKKIIKKLLES-COOH | 7728 |
| 1-37 | H₂N-SDDPKESEGDLHCVCVKTTSLVRPRHITNLELIKAGG-COOH | 3805 |
| 38-74 | H₂N-HCPTANLIATKKNGRKLCLDLQAALYKKIIKKLLES-COOH | 3923 |
| 1-15 | H₂N-SDDPKESEGDLHCVC-COOH | 1544 |
| 13-27 | H₂N-CVCVKTTSLVRPRHI-COOH | 1619 |
| 25-39 | H₂N-RHITNLELIKAGGHC-COOH | 1572 |
| 37-51 | H₂N-GHCPTANLIATKKNG-COOH | 1443 |
| 49-63 | H₂N-KNGRKLCLDLQAALY-COOH | 1614 |
| 60-74 | H₂N-AALYKKIIKKLLES-COOH | 1653 |

GEOMETRIC MEAN MIC$_{100}$

| PATHOGEN | NUTRIENT BROTH | | | | MUELLER-HINTON BROTH | | | |
|---|---|---|---|---|---|---|---|---|
| | pH 5.5 | | pH 7.2 | | pH 5.5 | | pH 7.2 | |
| | 50% | 100% | 50% | 100% | 50% | 100% | 50% | 100% |
| SA | 70.7 | 100 | 3.1 | 3.1 | 100 | >100 | 6.3 | 25 |
| SE | 6.3 | 8.8 | 1.6 | 3.1 | 1.6 | 3.1 | 25 | 25 |
| EF | 50 | >100 | 25 | 50 | >100 | >100 | 25 | 35 |
| SM | 35.4 | 35.4 | 1.6 | 3.1 | 6.1 | 25 | 6.3 | 6.3 |
| EC | 25 | 25 | 12.5 | 12.5 | 12.5 | 25 | 12.5 | 12.5 |
| PA | 8.8 | 12.5 | 6.3 | 6.3 | 3.1 | 25 | 12.5 | 0.8 |
| CA | 17.7 | 35.4 | 6.3 | 12.5 | >100 | 100 | 25 | 25 |
| CN | 12.5 | 25 | 1.6 | 1.6 | >100 | 1.6 | 3.1 | 6.3 |

- ORGANISM INOCULUM = $1 \times 10^5$ CFU/ml; LOGARITHMIC-PHASE CELLS
- PEPTIDE CONCENTRATION = 10 μg/ml; (4.6 nmoles / ml ; 4.6 μM)
- INCUBATION 37°C, AMBIENT $CO_2$; MIC$_{100}$ READ AT 24HR (n ≥ 2)

FIG. 20

GEOMETRIC MEAN MIC$_{100}$

| | NUTRIENT BROTH | | | | MUELLER-HINTON BROTH | | | |
|---|---|---|---|---|---|---|---|---|
| | pH 5.5 | | pH 7.2 | | pH 5.5 | | pH 7.2 | |
| PATHOGEN | 50% | 100% | 50% | 100% | 50% | 100% | 50% | 100% |
| SA | 1.6 | 8.8 | 6.3 | 8.8 | 25 | 100 | >100 | 100% |
| SE | 3.1 | 3.1 | 3.1 | 3.1 | 3.1 | 3.1 | >100 | >100 |
| EF | 6.3 | 6.3 | 12.5 | 25 | 25 | 100 | 100 | >100 |
| SM | 3.1 | 1.6 | 3.1 | 3.1 | 12.5 | 50 | 12.5 | >100 |
| EC | 12.5 | 25 | 6.3 | 12.5 | 100 | >100 | >100 | >100 |
| PA | 4.4 | 8.8 | 6.3 | 12.5 | 50 | 100 | 100 | 25 |
| CA | 6.3 | 8.8 | 6.3 | 6.3 | 25 | 100 | 25 | 100 |
| CN | 1.6 | 1.6 | 2.2 | 1.6 | 3.1 | 1.6 | 3.1 | 50 |

FIG. 21

ORGANISM INOCULUM = 1×10$^5$ CFU/ml; LOGARITHMIC-PHASE CELLS
PEPTIDE CONCENTRATION = 10 μg/ml; (4.3 nmoles / ml ; 4.3 μM)
INCUBATION 37°C, AMBIENT CO$_2$; MIC$_{100}$ READ AT 24HR (n ≥ 2)

FIG. 22

GEOMETRIC MEAN MIC$_{100}$

| PATHOGEN | NUTRIENT BROTH | | | | MUELLER-HINTON BROTH | | | |
|---|---|---|---|---|---|---|---|---|
| | pH 5.5 | | pH 7.2 | | pH 5.5 | | pH 7.2 | |
| | 50% | 100% | 50% | 100% | 50% | 100% | 50% | 100% |
| SA | 1.6 | 6.3 | 3.1 | 2.2 | 50 | 100 | >100 | >100 |
| SE | 1.6 | 1.6 | 1.6 | 1.6 | 3.1 | 3.1 | >100 | >100 |
| EF | 2.2 | 3.1 | 17.7 | 35.4 | 50 | 100 | >100 | >100 |
| SM | 0.2 | 0.4 | 1.6 | 2.2 | 25 | 50 | >100 | >100 |
| EC | 6.3 | 8.8 | 3.1 | 6.3 | 100 | >100 | 12.5 | 6.3 |
| PA | 1.6 | 3.1 | 3.1 | 6.3 | 12.5 | 100 | 100 | 25 |
| CA | 4.4 | 4.4 | 3.1 | 4.4 | 25 | 50 | 12.5 | >100 |
| CN | 2.2 | 0.78 | 1.6 | 1.6 | 1.6 | 3.1 | 6.3 | 3.1 |

ORGANISM INOCULUM = $1 \times 10^5$ CFU/ml; LOGARITHMIC-PHASE CELLS
PEPTIDE CONCENTRATION = 10 μg/ml; (5.9 nmoles / ml ; 5.9 μM)
INCUBATION 37°C, AMBIENT $CO_2$; MIC$_{100}$ READ AT 24HR (n ≥ 2)

GEOMETRIC MEAN MIC$_{100}$

| | NUTRIENT BROTH | | | | MUELLER-HINTON BROTH | | | |
|---|---|---|---|---|---|---|---|---|
| | pH 5.5 | | pH 7.2 | | pH 5.5 | | pH 7.2 | |
| PATHOGEN | 50% | 100% | 50% | 100% | 50% | 100% | 50% | 100% |
| SA | 19.8 | 25 | >100 | >100 | 100 | 100 | >100 | >100 |
| SE | 5 | 6.3 | >100 | >100 | 100 | 6.25 | 100 | >100 |
| EF | 12.5 | 25 | >100 | >100 | 100 | 100 | 100 | >100 |
| SM | 6.3 | 19.8 | >100 | >100 | 50 | >100 | 100 | >100 |
| EC | 12.5 | 25 | >100 | >100 | 50 | >100 | 100 | 100 |
| PA | 9.9 | 19.8 | >100 | >100 | 50 | >100 | 100 | >100 |
| CA | 25 | 39.7 | 12.5 | 50 | >100 | >100 | >100 | >100 |
| CN | 12.5 | 12.5 | 12.5 | 25 | 25 | 100 | 50 | >100 |

FIG. 23

ORGANISM INOCULUM = $1 \times 10^5$ CFU/ml; LOGARITHMIC-PHASE CELLS
PEPTIDE CONCENTRATION = 10 μg/ml; (5.4 nmoles / ml ; 5.4 μM)
INCUBATION 37°C, AMBIENT $CO_2$; MIC$_{100}$ READ AT 24HR (n ≥ 2)

pH 7.2

| PEPTIDE | ANTIMICROBIAL ACTIVITY † | | | | | | | | TOXICITY ‡ | |
|---|---|---|---|---|---|---|---|---|---|---|
| | SA | SE | EF | SM | EC | PA | CA | CN | RBC$_{Hg}$ | HUVEC |
| RP-1 | 3.1 | 3.1 | 25 | 3.1 | 12.5 | 6.3 | 12.5 | 6.3 | >98% | <5% |
| RP-2 | 6.3 | 6.3 | 25 | 1.6 | 100 | 25 | >100 | 12.5 | 95% | 5% |
| RP-3 | 3.1 | 3.1 | 50 | 1.6 | 6.3 | 25 | 12.5 | 1.6 | 95% | 5% |
| RP-4 | 12.5 | 4.4 | 50 | 4.4 | >100 | 50 | 12.5 | 3.1 | 97% | 7% |
| RP-5 | 8.8 | 3.1 | 50 | 4.4 | 100 | 25 | 17.7 | 4.4 | 95% | 6% |
| RP-7 | 70.7 | 12.5 | 50 | 25 | 100 | >100 | 50 | 25 | 85% | 12% |
| RP-8 | 6.3 | 3.1 | 25 | 3.1 | 12.5 | 12.5 | 6.3 | 1.6 | 90% | 7% |
| RP-11 | 6.3 | 1.6 | 35.4 | 2.2 | 6.3 | 6.3 | 4.4 | 3.1 | 87% | 8% |
| RP-13 | >100 | >100 | >100 | >100 | >100 | >100 | >100 | >100 | 94% | 5% |

· ORGANISM INOCULUM = $1 \times 10^5$ CFU/ml; LOGARITHMIC-PHASE CELLS
· PEPTIDE CONCENTRATION = 10 μg/ml; 37°C, AMBIENT $CO_2$; 24 OR 48HR
· † GEOMETRIC MEANS OF $MIC_{100}$ ($n \geq 2$); ‡ IN VITRO TOXICITY MARKERS

FIG. 24 pH 5.5

| PEPTIDE | ANTIMICROBIAL ACTIVITY † | | | | | | | | TOXICITY ‡ | |
|---|---|---|---|---|---|---|---|---|---|---|
| | SA | SE | EF | SM | EC | PA | CA | CN | RBC_Hg | HUVEC |
| RP-1 | 70.7 | 6.3 | 50 | 35.4 | 25 | 8.8 | 17.7 | 12.5 | ND | ND |
| RP-2 | >100 | 12.5 | 100 | 12.5 | >100 | 100 | >100 | 50 | ND | ND |
| RP-3 | 100 | >100 | 50 | 12.5 | 100 | 100 | 25 | 25 | ND | ND |
| RP-4 | 8.8 | 2.2 | 50 | 6.3 | 70.7 | 17.7 | 25 | 3.1 | ND | ND |
| RP-5 | 4.4 | 0.4 | 25 | 0.8 | 50 | 8.8 | 12.5 | 3.1 | ND | ND |
| RP-7 | 100 | 25 | 100 | 50 | >100 | 100 | 100 | 12.5 | ND | ND |
| RP-8 | 3.1 | 3.1 | 6.3 | 1.6 | 12.5 | 8.8 | 8.8 | 3.1 | ND | ND |
| RP-11 | 3.1 | 1.6 | 25 | 0.4 | 12.5 | 3.1 | 6.3 | 3.1 | ND | ND |
| RP-13 | 12.5 | 6.3 | 25 | 19.8 | 25 | 19.8 | 12.5 | 6.3 | ND | ND |

· ORGANISM INOCULUM = 1×10⁻⁵ CFU/ml; LOGARITHMIC-PHASE CELLS
· PEPTIDE CONCENTRATION = 10 μg/ml; 37C, AMBIENT $CO_2$; 24 OR 48HR
· † GEOMETRIC MEANS OF $MIC_{100}$ (n ≥ 2); ‡ IN VITRO TOXICITY MARKERS

FIG. 25

ANTIMICROBIAL PEPTIDES AND DERIVED METAPEPTIDES

RELATED APPLICATIONS

This present application is a continuation of U.S. application Ser. No. 12/911,693, filed Oct. 25, 2010, now U.S. Pat. No. 8,440,792, issued May 14, 2013, which is a continuation of U.S. application Ser. No. 09/648,816, filed Aug. 25, 2000, now U.S. Pat. No. 7,820,619, issued Oct. 26, 2010, which is a continuation-in-part of U.S. application Ser. No. 09/622,561, having a 35 U.S.C. 371(c) date of Oct. 6, 2000, now abandoned, which is the U.S. national stage application of International Application No. PCT/US99/03350, filed Feb. 17, 1999, which is a continuation-in-part of U.S. application Ser. No. 09/025,319, filed Feb. 18, 1998, now abandoned, the contents of which are incorporated herein by reference in their entireties.

BACKGROUND OF THE INVENTION

1. Field of the Invention

This invention relates generally to antimicrobial agents, and more specifically pertains to peptides useful as antimicrobial agents for the prevention and treatment of infections caused by organisms, such as bacteria and fungi, many of which are resistant to conventional antibiotics.

2. Description of Related Art

Human infections due to antibiotic-resistant bacteria and fungi are increasing in frequency and severity. Microbial pathogens exhibiting resistance to one or more antibiotics can now commonly be found in community and nosocomial settings. Antibiotic resistant pathogens currently of the greatest concern are methicillin (multiple) resistant *Staphylococcus aureus* (MRSA), vancomycin intermediate-resistant *S. aureus* (VISA) or vancomycin-resistant *S. aureus* (VRSA), vancomycin resistant *Enterococcus faecalis* or *Enterococcus faecium* (VRE), multi drug-resistant *Streptococcus pneumoniae* (MDRSPn) or *Streptococcus pyogenes* (MDRSPy), multidrug-resistant *Pseudomonas aeruginosa* (MDRPA), and azole resistant *Candida albicans* (ARCA).

Antimicrobial peptides have heretofore generally been considered to have undesirable toxicity, immunogenicity, and short half-lives due to biodegradation. However, endogenous antimicrobial peptides are believed to be integral to non-oxidative mechanisms of antimicrobial host defense. Stable, peptide-resistant mutants are rare, likely because microbicidal peptides appear to target the cytoplasmic membrane or other essential structures and/or functions of pathogens.

Investigations conducted over the past decade have demonstrated the existence of potent microbicidal peptides from various mammalian tissues. Perhaps the most thoroughly studied among these are defensins from neutrophil azurophilic granules. Related peptides such as β-defensins and cryptdins have also been isolated and characterized. To date, nearly 20 distinct defensins have been found in mammalian neutrophils.

Aside from neutrophils, the probability that platelets play an integral role in host defense against infection has been demonstrated by the following facts: i) platelets are the earliest and predominant cells at sites of microbial infection of vascular endothelium; ii) platelets adhere to and internalize microbial pathogens; iii) bacterial, fungal, and protozoal pathogens are damaged or killed by activated platelets in vitro; iv) thrombocytopenia increases susceptibility to and severity of some infections; v) rabbit and human platelets release platelet microbicidal proteins (PMPs) when stimulated with microorganisms or platelet agonists integral to infection in vitro; and vi) PMPs exert rapid and potent microbicidal activities against a broad spectrum of pathogens in vitro. It has been hypothesized that PMPs substantially contribute to platelet antimicrobial host defense by direct microbicidal actions, and may amplify cell mediated immune mechanisms such as neutrophil microbicidal activity. Similar to defensins, PMPs appear to disrupt microbial cytoplasmic membranes to achieve microbicidal activity. Present data indicates that PMP-2 (Sequence No. 1), tPMP-1, and defensin hNP-1 employ distinct mechanisms, and that these differences are related to differences in protein structure.

The majority of known mammalian antimicrobial peptides have been localized within leukocytes (e.g., defensins), or secreted onto epithelial surfaces such as intestinal lumen or tracheal epithelium (e.g., cryptdins, tracheal antimicrobial peptide). Prohibitive levels of mammalian cell toxicity have been noted with many of these peptides when they have been tested as antimicrobial therapeutics. In contrast, PMPs exert potent in vitro microbicidal activity against a broad spectrum of bacteria and fungi under physiological conditions that exist in the intravascular space. Several PMPs are released from platelets stimulated with agonists associated with infection. Therefore, in response to tissue injury, PMPs are likely released into the mammalian bloodstream at localized sites of infection. In preliminary studies, tPMP-1 and PMP-2 (Sequence No. 1) have been found to cause minimal damage of human erythrocytes or vascular endothelial cells in vitro as compared with defensin hNP-1. In addition, PMPs exert potent microbicidal activity against bacterial and fungal pathogens, comparable to defensins which have been observed at concentrations as low as 0.5 µg/ml in vitro. These potencies compare favorably to potent conventional antimicrobial agents such as aminoglycosides or amphotericin B.

A large family of antimicrobial peptides from mammalian platelets has also been isolated, and amino acid compositions and primary structures of endogenous antimicrobial peptides originating from mammalian and non-mammalian tissues now constitute a database of over 300 antimicrobial peptides. Recent advances in peptide structural analyses have provided important new information regarding the relationship between structure and microbicidal activities among these peptides. For example, the fact that many antimicrobial peptides are small, cationic, and contain amphiphilic α-helical domains is well established.

It would be desirable to provide peptides that are active against organisms that exhibit resistance to antibiotics, for use either independently or in combination to potentiate conventional antimicrobial agents or other antimicrobial peptides and/or which potentiate the antimicrobial functions of leukocytes. It is also desirable to provide microbicidal peptides that are based upon natural antimicrobial peptides, to overcome problems of toxicity and immunogenicity. To overcome short half-life due to degradation, such peptides should be resistant to proteolytic degradation, and should be stable in temperatures as high as 80° C., and in extremes of alkalinity and acidity, ranging from about pH 2 to about pH 10, for example. It is further desirable that such peptides should be amenable to chemical synthesis or recombinant DNA-based expression, facilitating their production in quantities necessary for testing or therapeutic application. The present invention addresses, at least in part, these and other needs.

SUMMARY OF THE INVENTION

Briefly, and in general terms, the present invention provides for peptides and derivative metapeptides (peptides derived from primary peptide templates) that likely target the microbial cytoplasmic membrane, leading to perturbation of the membrane. These effects almost certainly lead to ensuing effects on intracellular targets. This, along with secondary effects on intracellular functions such as macromolecular synthesis or bioenergetics, leads to overall cellular disruption and rapid death of the targeted microbes.

The invention accordingly provides for antimicrobial peptides for potentiating antimicrobial agents active against pathogenic organisms such as bacteria and fungi. The present invention provides for 1) novel antimicrobial peptides that act directly on the pathogen to exert microbicidal or microbiostatic activity; 2) novel antimicrobial peptides that potentiate one or more antimicrobial activities of leukocytes; and 3) novel antimicrobial peptide mosaics that combine such direct and leukocyte potentiating activities. In one presently preferred embodiment, the antimicrobial peptide comprises a peptide having an amino acid sequence selected from the group of amino acid sequences consisting essentially of a first peptide template XZBZBXBXB and derivatives thereof selected from the group consisting of XZBBZBXBXB, BXZXB, BXZXZXB, XBBXZXBBX, and BBXZBBXZ, and a second peptide template XBBXX and derivatives thereof selected from the group consisting of XBBXBBX, XBBXXBBX, BXXBXXB, XBBZXX, XBBZXXBB, and XBBZXXBBXXZBBX, where B is at least one positively charged amino acid, X is at least one non-polar, hydrophobic amino acid, and Z is at least one aromatic amino acid. In a presently preferred aspect of the invention, B is selected from the group of amino acids consisting of lysine, arginine, histidine, and combinations thereof; X is selected from the group of amino acids consisting of leucine, isoleucine, alanine, valine, and combinations thereof; and Z is selected from the group of amino acids consisting of phenylalanine, tryptophan, tyrosine and combinations thereof. Other amino acids, including glutamine, asparagine, proline, cystine, aspartic acid, glutamic acid, glycine, methionine, serine and threonine, may be interplaced within these primary structural motifs in a given case. In another aspect, the peptide or derived metapeptide of the invention can further comprise D-isomeric amino acids. In another aspect, the peptide or derived metapeptide of the invention can further comprise a retromeric sequence of amino acids. In a further aspect, the peptide or derived metapeptide of the invention can further comprise a modified amino acid group selected from the group consisting of N-∈monomethyl-lysine, (β-branched, N-methyl, α,β-dehydro, α,α-dialkyl, fluorinated amino acids, and combinations thereof in direct or retromeric sequences. The antimicrobial peptides can also be truncations, extensions, combinations or fusions of the template peptides disclosed. Despite these variations, the disclosed peptides will adhere to the general structural motifs indicated, thereby preserving their uniqueness. In a preferred embodiment, the total length of the peptides of the invention will be less than about 150 residues, and the total length preferably will be approximately 5 to 150 residues.

In another aspect of the invention, antimicrobial peptides and derived metapeptides that potentiate antimicrobial activity of leukocytes and are active alone or in combination with other agents directly against organisms such as bacteria and fungi can comprise peptides having amino acid sequences selected from the group consisting essentially of combined amino acid sequences AL and LA, wherein A represents an antimicrobial domain consisting essentially of a first peptide template XZBZBXBXB and derivatives thereof selected from the group consisting of XZBBZBXBXB, BXZXB, BXZXZXB, XBBXZXBBX, and BBXZBBXZ, and a second peptide template XBBXX and derivatives thereof selected from the group consisting of XBBXBBX, XBBXXBBX, BXXBXXB, XBBZXX, XBBZXXBB, and XBBZXXBBXXZBBX and L represents a leukocyte potentiating domain consisting essentially of JJJCJCJJJJJJ, and J is selected from X, Z and B. Thus, an example of AL can be: XZBZBXBXBJJJCJCJJJJJ; and an example of LA can be: JJJCJCJJJJJXZBZBXBXB.

Within one aspect of the present invention antimicrobial peptides are provided comprising a peptide of from 7 to 74 amino acids containing a 7 amino acid core sequence: $aa_1$-$aa_2$-$aa_3$-$aa_4$-$aa_5$-$aa_6$-$aa_7$, wherein $aa_1$ is the amino-terminus of the core sequence; one of $aa_6$ and $aa_7$ is selected from the group consisting of phenylalanine, tryptophan and tyrosine, such that when $aa_6$ is phenylalanine $aa_7$ is selected from the group consisting of lysine, arginine and histidine, when $aa_6$ is tryptophan $aa_7$ is lysine, and when $aa_7$ is phenylalanine $aa_6$ is leucine; and retromers, truncations, extensions, combinations, fusions, and derivatives thereof, the peptide having antimicrobial activity. Within one embodiment, $aa_1$ is selected from the group consisting of alanine, lysine and glycine; $aa_2$ is selected from the group consisting of leucine and arginine; $aa_3$ is tyrosine; and $aa_4$ and $aa_5$ are selected from the group consisting of lysine, $aa_4$ and $aa_5$ are selected from the group consisting of lysine and arginine.

Within another aspect of the invention antimicrobial peptides are provided comprising a peptide of from 7 to 74 amino acids containing a 7 amino acid core sequence: $aa_1$-$aa_2$-$aa_3$-$aa_4$-$aa_5$-$aa_6$-$aa_7$, wherein $aa_1$ is the amino-terminus of the peptide; $aa_6$ is selected from the group consisting of phenylalanine and tryptophan and tyrosine; and $aa_7$ is selected from the group consisting of lysine and arginine; and retromers, truncations, extensions, combinations, fusions, and derivatives thereof, the peptide having antimicrobial activity. Within one embodiment of the above $aa_6$ is selected from the group consisting of phenylalanine and tryptophan, and $aa_7$ is selected from the group consisting of lysine and arginine. Within other embodiments, $aa_1$ is selected from the group consisting of alanine, lysine and glycine; $aa_2$ is selected from the group consisting of leucine and arginine; $aa_3$ is tyrosine; and $aa_4$ and $aa_5$ are selected from the group consisting of lysine, arginine, glutamine, proline, histidine and asparagine. Within further embodiments $aa_4$ and $aa_5$ are selected from the group consisting of lysine and arginine.

Within another aspect of the invention antimicrobial peptides are provided comprising a peptide of from 13 to 18 amino acids containing a 12 amino acid core sequence; $aa_1$-$aa_2$-$aa_3$-$aa_4$-$aa_5$-$aa_6$-$aa_7$-$aa_8$-$aa_9$-$aa_{10}$-$aa_{11}$-$aa_{12}$, wherein $aa_1$ is the amino-terminus of the peptide and is selected from the group consisting of leucine, isoleucine, alanine, valine, serine, lysine and glycine; $aa_2$ is selected from the group consisting of leucine, isoleucine, alanine, valine, serine and arginine; $aa_3$ is selected from the group consisting of phenylalanine, tryptophan and tyrosine; $aa_4$ and $aa_5$ are selected from the group consisting of lysine, arginine and histidine; one of $aa_6$ and $aa_7$ is selected from the group consisting of phenylalanine, tryptophan and tyrosine, such that when $aa_6$ is phenylalanine $aa_7$ is selected from the group consisting of lysine, arginine and histidine, when $aa_6$ is tryptophan $aa_7$ is lysine, and when $aa_7$ is phenylalanine $aa_6$ is leucine; $aa_8$ is selected from the group consisting of lysine, arginine, histidine and asparagine; $aa_9$ is selected from the group consisting of lysine, arginine and histidine; $aa_{10}$ is selected from the group consisting of leucine, isoleucine, alanine, valine and serine; $aa_{11}$ is selected from the group consisting of leucine, isoleucine, alanine, valine, serine and lysine; and $aa_{12}$ is selected from the group consisting of lysine, arginine and histidine; and retromers, truncations, extensions, combinations, fusions, and derivatives thereof, the peptide having antimicrobial activity. Within a further embodiment $aa_1$ is selected from the group consisting of alanine, lysine and glycine; $aa_2$ is selected from the group consisting of leucine and arginine; $aa_3$ is tyrosine; $aa_4$, and $aa_5$ are selected from the group consisting of lysine and arginine; $aa_8$ is selected from the group consisting of lysine and asparagine; $aa_9$ is lysine; $aa_{10}$ is selected from the group consisting of leucine and isoleucine; $aa_{11}$ is selected from the group consisting of leucine and lysine; and $aa_{12}$ is selected from the group consisting of lysine and arginine. Within yet further embodiments one of $aa_6$ and $aa_7$ is selected from the group consisting of phenylalanine and tryptophan, such that when $aa_6$ is phenylalanine $aa_7$ is selected from the group consisting of lysine and arginine, when $aa_6$ is tryptophan $aa_7$ is lysine, and when $aa_7$ is phenylalanine $aa_6$ is leucine. Within other embodiments $aa_1$ is selected from the group consisting of alanine, lysine and glycine; $aa_2$ is selected from the group consisting of leucine and arginine; $aa_3$ is tyrosine; $aa_6$ is selected from the group consisting of phenylalanine, tryptophan and tyrosine; $aa_7$ is selected from the group consisting of lysine and arginine; $aa_8$ is selected from the group consisting of lysine and asparagine; $aa_9$ is lysine; $aa_{10}$ is selected from the group consisting of leucine and isoleucine; $aa_{11}$ is selected from the group consisting of leucine and lysine; and $aa_{12}$ is selected from the group consisting of $aa_6$ is phenylalanine $aa_7$ is lysine or arginine, and when $aa_6$ is tryptophan $aa_7$ is lysine. Within other embodiments $aa_6$ is selected from the group consisting of phenylalanine, tryptophan and tyrosine; and $aa_7$ is selected from the group consisting of lysine and arginine. Within yet other embodiments $aa_6$ is phenylalanine $aa_7$ is selected from the group consisting of lysine and arginine, and when $aa_6$ is tryptophan $aa_7$ is lysine.

Within another aspect of the invention antimicrobial peptides are provided comprising a peptide of from 13 to 18 amino acids containing a 13 amino acid core sequence: $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$, wherein $aa_1$ is the amino-terminus of the peptide and is selected from the group consisting of leucine, isoleucine, alanine, valine, serine, lysine and glycine; $aa_2$ is selected from the group consisting of leucine, isoleucine, alanine, valine, serine and arginine; $aa_3$ is selected from the group consisting of phenylalanine, tryptophan, tyrosine; $aa_4$ and $aa_5$ are selected from the group consisting of lysine, arginine and histidine; one of $aa_6$ and $aa_7$ is selected from the group consisting of phenylalanine, tryptophan, tyrosine, and the other of $aa_6$ and $aa_7$ is selected from the group consisting of lysine, arginine and leucine, wherein when $aa_6$ is phenylalanine $aa_7$ is selected from the group consisting of lysine and arginine, when $aa_6$ is tryptophan $aa_7$ is lysine, and when $aa_7$ is phenylalanine $aa_6$ is leucine; $aa_8$ is selected from the group consisting of lysine, arginine, histidine and asparagine; $aa_9$ is selected from the group consisting of lysine, arginine and histidine; $aa_{10}$ is selected from the group consisting of leucine, isoleucine, alanine, valine and serine; $aa_{11}$ is selected from the group consisting of leucine, isoleucine, alanine, valine, serine and lysine; and $aa_{12}$ is selected from the group consisting of lysine, arginine and histidine; and $aa_{13}$ is selected from the group consisting of leucine, isoleucine, alanine, valine, serine, arginine and phenylalanine; and retromers, truncations, extensions, combinations, fusions, and D-isomeric amino acid, retromeric, N-monomethyl-lysine, and fluorinated amino acid derivatives thereof, the peptide having antimicrobial activity. Within one embodiment $aa_1$ is selected from the group consisting of alanine, lysine and glycine; $aa_2$ is selected from the group consisting of leucine and arginine; $aa_3$ is tyrosine; $aa_4$ and $aa_5$ are selected from the group consisting of lysine, arginine and histidine; $aa_8$ is selected from the group consisting of lysine and asparagine; $aa_9$ is lysine; $aa_{10}$ is selected from the group consisting of leucine and isoleucine; $aa_{11}$ is selected from the group consisting of leucine and lysine; and $aa_{12}$ is selected from the group consisting of lysine and arginine. Within another embodiment $aa_{13}$ is selected from the group consisting of serine, leucine, arginine and phenylalanine.

Within other aspects of the invention antimicrobial peptides are provided comprising a peptide of from 13 to 74 containing an amino acid core sequence selected from the group consisting of truncations of PMP-1 (Sequence No. 2), and retromers, extensions, combinations and fusions thereof; truncations of PMP-2 (Sequence No. 1), and retromers, extensions, combinations and fusions thereof. Within one embodiment the antimicrobial peptide further comprises a pharmaceutically acceptable carrier. Within other embodiments the peptide is a truncation of PMP-2 (Sequence No. 1) and comprises residues 28 to 74 of PMP-2 (Sequence No. 1). Within further embodiments the peptide is a truncation of PMP-2 (Sequence No. 1) and comprises residues 43 to 74 of PMP-2 (Sequence No. 1). Within yet other embodiments the peptide is a truncation of PMP-2 (Sequence No. 1) and comprises residues 59 to 74 of PMP-2 (Sequence No. 1). Within another embodiment the peptide is a truncation of PMP-2 (Sequence No. 1) and comprises residues 45 to 74 of PMP-2 (Sequence No. 1). Within a further embodiment the peptide comprises an extension of RP-1 (Sequence No. 3) by RP-1 residues 1-10. Within an alternative embodiment the peptide comprises a combination of RP-1 (Sequence No. 3) with RP-13 (Sequence No. 14).

Within another aspect of the invention antimicrobial peptides are provided comprising a peptide of from 8 to 20 amino acids containing an amino acid core sequence of a first amino acid sequence domain, a second amino acid sequence domain, and a third amino acid sequence domain, where the first amino acid sequence domain is a sequence of from one to six amino acids selected from the group consisting of leucine, isoleucine, alanine, valine, serine, glycine, and threonine; the second amino acid sequence domain is a sequence of from one to two amino acids selected from the group consisting of lysine, arginine, histidine, glutamine, proline, glutamic acid, aspartic acid and glycine; the third amino acid sequence domain is a sequence of from one to nine amino acids selected from the group consisting of leucine, isoleucine, alanine, valine, serine, glycine, and threonine; and where the amino acids within the first, second and third amino acid sequence domains may be separated, and the first, second and third amino acid domains may be separated from each other by up to three amino acids selected from the group consisting of asparagine, cystine, aspartic acid, glutamic acid and methionine; and retromers, truncations, extensions, combinations, fusions, and derivatives thereof, the peptide having antimicrobial activity. Within one embodiment the peptide contains an amino acid core sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$-$aa_{17}$, wherein $aa_1$ is the amino-terminus of the peptide and is selected from the group consisting of leucine, isoleucine, alanine, valine, serine, glycine, and threonine; $aa_2$ is selected from the group consisting of leucine, isoleucine, alanine, valine, serine, glycine, and threonine; $aa_3$ and $aa_4$ are selected from the group consisting of lysine, arginine, histidine, glutamine, and proline; $aa_5$ is selected from the group consisting of asparagine, cystine, aspartic acid, glutamic acid and methionine; $aa_6$ is selected from the group consisting of leucine, isoleucine, alanine, valine, serine, glycine, and threonine; $aa_7$ is selected from the group consisting of lysine, arginine, histidine, glutamine, proline, glutamic acid, aspartic acid and glycine; $aa_8$ is selected from the group consisting of lysine, arginine, histidine, glutamine, proline and glutamic acid; $aa_9$, $aa_{11}$, $aa_{13}$, $aa_{15}$, $aa_{16}$, and $aa_{17}$ are selected from the group consisting of leucine, isoleucine, alanine, valine, serine, glycine, and threonine; $aa_{10}$ and $aa_{12}$ are selected from the group consisting of asparagine, cystine, aspartic acid, glutamic acid and methionine; and $aa_{14}$ is selected from the group consisting of lysine, arginine, histidine, glutamine and proline. Within another embodiment the peptide contains an amino acid core sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$-$aa_{17}$, wherein $aa_1$ is the amino-terminus of the peptide core sequence and is alanine; $aa_2$ is threonine; $aa_3$ and $aa_4$ are lysine; $aa_5$ is asparagine; $aa_6$ is glycine; $aa_7$ is arginine; $aa_8$ is lysine; $aa_9$, $aa_{11}$, $aa_{13}$ and $aa_{17}$ are leucine; $aa_{10}$ is cystine; $aa_{12}$ is aspartic acid; $aa_{14}$ is glutamine, and $aa_{15}$ and $aa_{16}$ are alanine. Within other embodiments the peptide contains an amino acid core sequence $aa_1$-$aa_2$-$aa_3$-$aa_4$-$aa_5$-$aa_6$-$aa_7$-$aa_8$, wherein $aa_1$ is the amino-terminus of the peptide core sequence and is arginine; $aa_2$ is phenylalanine; $aa_3$ is glutamic acid; $aa_4$ is lysine; $aa_5$ is serine; $aa_6$ is lysine; $aa_7$ is isoleucine; and $aa_8$ is lysine. Within another embodiment the peptide contains an amino acid core sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$-$aa_{17}$-$aa_{18}$-$aa_{19}$-$aa_{20}$, wherein $aa_1$ is the amino-terminus of the peptide and is serine; $aa_2$ is alanine; $aa_3$ is isoleucine; $aa_4$ is histidine; $aa_5$ is proline; $aa_6$ and $aa_7$ are serine; $aa_8$ is isoleucine; $aa_9$ is leucine; $aa_{10}$ is lysine; $aa_{11}$ is leucine; $aa_{12}$ is glutamic acid; $aa_{13}$ is valine; $aa_{14}$ is isoleucine; $aa_{15}$ is cystine; $aa_{16}$ is isoleucine; $aa_{17}$ is glycine; $aa_{18}$ is valine; $aa_{19}$ is leucine; and $aa_{20}$ is glutamine. Within further embodiments the peptide contains an amino acid core sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$, wherein $aa_1$ is the amino-terminus of the peptide and is tyrosine; $aa_2$ is alanine; $aa_3$ is selected from the group consisting of aspartic acid and glutamic acid; $aa_4$ and $aa_5$ are selected from the group consisting of leucine, arginine and histidine; $aa_6$ is cystine; $aa_7$ is selected from the group consisting of threonine or valine; $aa_8$ is cystine; $aa_9$ is serine; $aa_{10}$ is isoleucine; $aa_{11}$ is lysine; $aa_{12}$ is alanine; $aa_{13}$ is glutamic acid; and $aa_{14}$ is valine.

Within another aspect of the invention antimicrobial peptides are provided comprising a peptide of from 5 to 150 amino acids containing an amino acid core sequence of a first amino acid sequence domain, a second amino acid sequence domain, a third amino acid sequence domain, and a fourth amino acid sequence domain, and wherein the first amino acid sequence domain is at the amino-terminus of the amino acid core sequence and is a sequence of from one to five amino acids selected from the group consisting of phenylalanine, tryptophan, tyrosine, where amino acids of the first amino acid sequence domain may be separated from each other by an amino acid selected from the group consisting of leucine, isoleucine, alanine, valine and serine; the second amino acid sequence domain is an amino acid selected from the group consisting of lysine, arginine, histidine, glutamine, and proline; the third amino acid sequence domain is a sequence of from one to five amino acids selected from the group consisting of phenylalanine, tryptophan, tyrosine; and the fourth amino acid sequence domain is an amino acid selected from the group consisting of lysine, arginine, histidine, glutamine, and proline; and retromers, truncations, extensions, combinations, fusions, and derivatives thereof, the peptide having antimicrobial activity. Within one embodiment the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$, wherein $aa_1$ is the amino-terminus of the peptide and is lysine; $aa_2$ is phenylalanine; $aa_3$ is lysine; $aa_4$ is histidine; $aa_5$ is tyrosine; $aa_6$ and $aa_7$ are phenylalanine; $aa_8$ is tryptophan; $aa_9$ is lysine; $aa_{10}$ is tyrosine; and $aa_{11}$ is lysine. Within another embodiment the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$, wherein $aa_1$ is the amino-terminus of the peptide and is lysine; $aa_2$ is glycine; $aa_3$ is tyrosine; $aa_4$ is phenylalanine; $aa_5$ is tyrosine; $aa_6$ is phenylalanine; $aa_7$ is leucine; $aa_8$ is phenylalanine; $aa_9$ is lysine; $aa_{10}$ is phenylalanine; and $aa_{11}$ is lysine. Within other embodiments the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$, wherein $aa_1$ is the amino-terminus of the peptide and is lysine; $aa_2$ is tryptophan; $aa_3$ is lysine; $aa_4$, $aa_5$, $aa_6$, $aa_7$ and $aa_8$ are tryptophan; $aa_9$ is lysine; $aa_{10}$ is tryptophan; and $aa_{11}$ is lysine.

Within another aspect of the invention antimicrobial peptides are provided comprising a peptide of from 11 to 20 amino acids containing from one to four units of an amino acid core sequence domain, wherein adjacent units of the amino acid core sequence domain may be separated from each other by from one to two amino acids selected from the group consisting of phenylalanine, tryptophan, tyrosine, asparagine, cystine, aspartic acid, glutamic acid and methionine; wherein the amino acid sequence domain consists of a first group of amino acids and a second group of amino acids, the first group of amino acids consisting of from one to six amino acids selected from the group of leucine, isoleucine, alanine, valine, serine, glycine, and threonine, and the second group of amino acids consisting of from one to three amino acids selected from the group of lysine, arginine, histidine, glutamine, and proline; wherein the amino acids in the first and second groups of amino acids may be separated by from one to two amino acids selected from the group consisting of phenylalanine, tryptophan, tyrosine, asparagine, cystine, aspartic acid, glutamic acid and methionine; and wherein the first and second groups of amino acids may be separated from each other by an amino acid selected from the group consisting of phenylalanine, tryptophan and tyrosine; and retromers, truncations, extensions, combinations, fusions, and derivatives thereof, the peptide having antimicrobial activity. Within one embodiment the peptide contains two of the units of the amino acid core sequence domain. Within a further embodiment two units of the amino acid core sequence domain are separated by an amino acid selected from the group consisting of asparagine, cystine, aspartic acid, glutamic acid and methionine, and an amino acid selected from the group consisting of phenylalanine, tryptophan and tyrosine. Within a further embodiment the two units of the amino acid core sequence domain are separated by an amino acid selected from the group consisting of phenylalanine, tryptophan and tyrosine. Within a related embodiment the peptide contains three of the units of the amino acid core sequence domain. Within another embodiment the first and second units of the amino acid core sequence domain are separated by an amino acid selected from the group consisting of phenylalanine, tryptophan and tyrosine. Within a related embodiment, the peptide contains four of the units of the amino acid core sequence domain. Within yet other embodiments, the first and second units of the amino acid core sequence domain are separated by an amino acid selected from the group consisting of phenylalanine, tryptophan and tyrosine.

Within another embodiment the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$, wherein $aa_1$ is the amino-terminus of the peptide and is proline, $aa_2$ is arginine, $aa_3$ is isoleucine, $aa_4$ and $aa_5$ are lysine, $aa_6$ is isoleucine, $aa_7$ is valine, $aa_8$ is glutamine, $aa_9$ and $aa_{10}$ are lysine, $aa_{11}$ is leucine, $aa_{12}$ is alanine, and $aa_{13}$ is glycine. Within a further embodiment, the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$-$aa_{17}$-$aa_{18}$-$aa_{19}$, wherein $aa_1$ is the amino-terminus of the peptide and is lysine, $aa_2$ is tryptophan, $aa_3$ is valine, $aa_4$ is arginine, $aa_5$ is glutamic acid, $aa_6$ is tryosine, $aa_7$ is isoleucine, $aa_8$ is asparagine, $aa_9$ is serine, $aa_{10}$ is leucine, $aa_{11}$ is glutamic acid, $aa_{12}$ is methionine, $aa_{13}$ is serine, $aa_{14}$ and $aa_{15}$ are lysine, $aa_{16}$ is glycine, $aa_{17}$ is leucine, $aa_{18}$ is alanine, and $aa_{19}$ is glycine. Within a further embodiment the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$-$aa_{17}$-$aa_{18}$-$aa_{19}$-$aa_{20}$, wherein $aa_1$ is the amino-terminus of the peptide and is glutamic acid, $aa_2$ is tryptophan, $aa_3$ is valine, $aa_4$ is glutamine, $aa_5$ is lysine, $aa_6$ is tryosine, $aa_7$ is valine, $aa_8$ is serine, $aa_9$ is asparagine, $aa_{10}$ is leucine, $aa_{11}$ is glutamic acid, $aa_{12}$ is leucine, $aa_{13}$ is serine, $aa_{14}$ is alanine, $aa_{15}$ is tryptophan, $aa_{16}$ and $aa_{17}$ are lysine, $aa_{18}$ is isoleucine, $aa_{19}$ is leucine, and $aa_{20}$ is lysine. Within yet another embodiment the peptide contains the amino acid sequence a $aa_1$-$aa_2$-$aa_3$-$aa_4$-$aa_5$-$aa_6$-$aa_7$-$aa_8$-$aa_9$-$aa_{10}$-$aa_{11}$-$aa_{12}$, wherein $aa_1$ is the amino-terminus of the peptide and is serine, $aa_2$ is tryptophan, $aa_3$ is valine, $aa_4$ is glutamine, $aa_5$ is glutamic acid, $aa_6$ is tryosine, $aa_7$ is valine, $aa_8$ is tryosine, $aa_9$ is asparagine, $aa_{10}$ is leucine, $aa_{11}$ is glutamic acid, and $aa_{12}$ is leucine. Within another embodiment the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$, wherein $aa_1$ is the amino-terminus of the peptide and is alanine, $aa_2$ is asparagine, $aa_3$ is serine, $aa_4$ is glycine, $aa_5$ is glutamic acid, $aa_6$ is glycine, $aa_7$ is asparagine, $aa_8$ is phenylalanine, $aa_9$ is leucine, $aa_{10}$ is alanine, $aa_{11}$ is glutamic acid, $aa_{12}$, $aa_{13}$ and $aa_{14}$ are glycine, $aa_{15}$ is valine, and $aa_{16}$ is arginine. Within yet another embodiment the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$-$aa_{17}$-$aa_{18}$-$aa_{19}$-$aa_{20}$, wherein $aa_1$ is the amino-terminus of the peptide and is alanine, $aa_2$ is asparagine, $aa_3$ is serine, $aa_4$ is glycine, $aa_5$ is glutamic acid, $aa_6$ is glycine, $aa_7$ is asparagine, $aa_8$ is phenylalanine, $aa_9$ is leucine, $aa_{10}$ is alanine, $aa_{11}$ is glutamic acid, $aa_{12}$, $aa_{13}$ and $aa_{14}$ are glycine, $aa_{15}$ is valine, $aa_{16}$ is arginine, $aa_{17}$ is lysine, $aa_{18}$ is leucine, $aa_{19}$ is isoleucine, and $aa_{20}$ is lysine.

Within further embodiments the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$, wherein $aa_1$ is the amino-terminus of the peptide and is glutamic acid, $aa_2$ is glycine, $aa_3$ is valine, $aa_4$ is asparagine, $aa_5$ is aspartic acid, $aa_6$ is asparagine, $aa_7$ and $aa_8$ are glutamic acid, $aa_9$ is glycine, $aa_{10}$ and $aa_{11}$ are phenylalanine, $aa_{12}$ is serine, and $aa_{13}$ is alanine. Within yet another embodiment the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$-$aa_{17}$-$aa_{18}$, wherein $aa_1$ is the amino-terminus of the peptide and is lysine, $aa_2$ is phenylalanine, $aa_3$ is asparagine, $aa_4$ is lysine, $aa_5$ is serine, $aa_6$ is lysine, $aa_7$ is leucine, $aa_8$ and $aa_9$ are lysine, $aa_{10}$ is threonine, $aa_{11}$ is glutamic acid, $aa_{12}$ is threonine, $aa_{13}$ is glutamine, $aa_{14}$ is glutamic acid, $aa_{15}$ is lysine, $aa_{16}$ is asparagine, $aa_{17}$ is proline, and $aa_{18}$ is leucine. Within further embodiments the peptide contains the amino acid sequence $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$, wherein $aa_1$ is the amino-terminus of the peptide and is alanine, $aa_2$ is asparagine, $aa_3$ is leucine, $aa_4$ is isoleucine, $aa_5$ is alanine, $aa6$ is threonine, $aa_7$ and $aa_8$ are lysine, $aa_9$ is asparagine, $aa_{10}$ is glycine, $aa_{11}$ is arginine, $aa_{12}$ is lysine, $aa_{13}$ is leucine, $aa_{14}$ is cystine, and $aa_{15}$ is leucine.

Within another aspect of the invention antimicrobial peptides are provided comprising a peptide of from 5 to 150 amino acids having a three amino acid core sequence of a first amino acid which is cystine, a second amino acid which is selected from the group consisting of leucine, isoleucine, alanine, valine, serine, glycine, threonine, phenylalanine, tryptophan, tyrosine, lysine, arginine, glutamine, proline, and histidine, and a third amino acid which is cystine.

Within another aspect of the invention antimicrobial peptides are provided comprising a peptide of from 5 to 150 amino acids having an amino acid core sequence of a first amino acid sequence domain, a second amino acid sequence domain, and a third amino acid sequence domain, wherein the first amino acid sequence domain is a sequence of three amino acids selected from the group consisting of leucine, isoleucine, alanine, valine, serine, glycine, threonine, phenylalanine, tryptophan, tyrosine, lysine, arginine, glutamine, proline, and histidine; the second amino acid sequence is a first amino acid which is cystine, a second amino acid which is selected from the group consisting of leucine, isoleucine, alanine, valine, serine, glycine, threonine, phenylalanine, tryptophan, tyrosine, lysine, arginine, glutamine, proline, and histidine, and a third amino acid which is cystine; and the third amino acid sequence is a sequence of six amino acids selected from the group consisting of leucine, isoleucine, alanine, valine, serine, glycine, threonine, phenylalanine, tryptophan, tyrosine, lysine, arginine, glutamine, proline, and histidine.

Within another aspect of the invention antimicrobial peptides are provided comprising a peptide of from 5 to 150 amino acids having an amino acid core sequence of a first amino acid sequence domain, a second amino acid sequence domain, a third amino acid sequence domain, and a fourth amino acid sequence domain, wherein the first amino acid sequence domain is a sequence of from 13 to 18 amino acids containing a 12 amino acid core sequence: $aa_1$-$aa_2$-$aa_3$-$aa_4$-$aa_5$-$aa_6$-$aa_7$-$aa_8$-$aa_9$-$aa_{10}$-$aa_{11}$-$aa_{12}$, wherein $aa_1$ is the amino-terminus of the peptide, one of $aa_6$ and $aa_7$ is selected from the group consisting of phenylalanine and tryptophan, such that when $aa_6$ is phenylalanine $aa_7$ is selected from the group consisting of lysine and arginine, when $aa_6$ is tryptophan $aa_7$ is lysine, and when $aa_7$ is phenylalanine $aa_6$ is leucine; the second amino acid sequence domain is a sequence of three amino acids selected from the group consisting of leucine, isoleucine, alanine, valine, serine, glycine, threonine, phenylalanine, tryptophan, tyrosine, lysine, arginine, glutamine, proline, and histidine; the third amino acid sequence domain is a first amino acid which is cystine, a second amino acid which is selected from the group consisting of leucine, isoleucine, alanine, valine, serine, glycine, threonine, phenylalanine, tryptophan, tyrosine, lysine, arginine, glutamine, proline, and histidine, and a third amino acid which is cystine; and the fourth amino acid sequence domain is a sequence of six amino acids selected from the group consisting of leucine, isoleucine, alanine, valine, serine, glycine, threonine, phenylalanine, tryptophan, tyrosine, lysine, arginine, glutamine, proline, and histidine.

Within another aspect of the invention antimicrobial peptides are provided comprising a peptide of from 5 to 150 amino acids having an amino acid core sequence of a first amino acid sequence domain, a second amino acid sequence domain, a third amino acid sequence domain, and a fourth amino acid sequence domain, wherein the first amino acid sequence domain is a sequence of three amino acids selected from the group consisting of leucine, isoleucine, alanine, valine, serine, glycine, threonine, phenylalanine, tryptophan, tyrosine, lysine, arginine, glutamine, proline, and histidine;

the second amino acid sequence is a first amino acid which is cystine, a second amino acid which is selected from the group consisting of leucine, isoleucine, alanine, valine, serine, glycine, threonine, phenylalanine, tryptophan, tyrosine, lysine, arginine, glutamine, proline, and histidine, and a third amino acid which is cystine; the third amino acid sequence is a sequence of six amino acids selected from the group consisting of leucine, isoleucine, alanine, valine, serine, glycine, threonine, phenylalanine, tryptophan, tyrosine, lysine, arginine, glutamine, proline, and histidine; and the fourth amino acid sequence domain is a sequence of from 13 to 18 amino acids containing a 12 amino acid core sequence: $aa_1$-$aa_2$-$aa_3$-$aa_4$-$aa_5$-$aa_6$-$aa_7$-$aa_8$-$aa_9$-$aa_{10}$-$aa_{11}$-$aa_{12}$, wherein $aa_1$, is the amino-terminus of the peptide, one of $aa_6$ and $aa_7$ is selected from the group consisting of phenylalanine and tryptophan, such that when $aa_6$ is phenylalanine $aa_7$ is selected from the group consisting of lysine and arginine, when $aa_6$ is tryptophan $aa_7$ is lysine, and when $aa_7$ is phenylalanine $aa_6$ is leucine, and retromers, truncations, extensions, combinations, fusions, and derivatives thereof, the peptide having antimicrobial activity.

Within another aspect of the invention antimicrobial peptides are provided comprising a peptide of from 11 to 22 amino acids containing an 10 amino acid core sequence: $aa_1$-$aa_2$-$aa_3$-$aa_4$-$aa_5$-$aa_6$-$aa_7$-$aa_8$-$aa_9$-$aa_{10}$, wherein $aa_1$ is the amino-terminus of the amino acid core sequence and is threonine; $aa_2$ and $aa_3$ are selected from the group consisting of lysine and arginine; $aa_1$ is asparagine; $aa_5$ is glycine; $aa_6$ is selected from the group consisting of lysine, arginine, glutamic acid and glycine; $aa_7$ is selected from the group consisting of lysine, arginine and glutamic acid; $aa_8$ is leucine; $aa_9$ is cystine; and $aa_{10}$ is leucine, and retromers, truncations, extensions, combinations, fusions, and derivatives thereof, the peptide having antimicrobial activity. Within one embodiment the amino acid core sequence further contains the amino acid sequence $aa_{11}$-$aa_{12}$-$aa_{13}$-$aa_{14}$-$aa_{15}$-$aa_{16}$, and wherein $aa_{11}$ is selected from the group consisting of aspartic acid, glutamic acid, lysine, and glycine; $aa_{12}$ is leucine; $aa_{13}$ is glutamine; $aa_{14}$ and $aa_{15}$ are alanine; and $aa_{16}$ is leucine. Within another embodiment the amino acid core sequence further contains the amino acid sequence $aa_{17}$-$aa_{18}$-$aa_{19}$, and wherein $aa_{17}$ is selected from the group consisting of tyrosine, phenylalanine and tryptophan; and $aa_{18}$ and $aa_{19}$ are selected from the group consisting of lysine, arginine, and glutamic acid. Within yet another embodiment the amino acid core sequence further contains the amino acid $aa_{20}$ selected from the group consisting of lysine, arginine, and glutamic acid.

Within another aspect of the invention antimicrobial peptides are provided comprising a peptide of from 11 to 22 amino acids containing an 11 amino acid core sequence: $aa_1$-$aa_2$-$aa_3$-$aa_4$-$aa_5$-$aa_6$-$aa_7$-$aa_8$-$aa_9$-$aa_{10}$-$aa_{11}$, wherein $aa_1$ is the amino-terminus of the amino acid core sequence and is alanine; $aa_2$ is threonine; $aa_3$ and $aa_4$ are selected from the group consisting of lysine and arginine; $aa_5$ is asparagine; $aa_6$ is glycine; $aa_7$ is selected from the group consisting of lysine, arginine, glutamic acid and glycine; $aa_8$ is selected from the group consisting of lysine, arginine and glutamic acid; $aa_9$ is leucine; $aa_{10}$ is cystine; and $aa_{11}$ is leucine, and retromers, truncations, extensions, combinations, fusions, and derivatives thereof, the peptide having antimicrobial activity. Within one embodiment the amino acid core sequence further contains the amino acid sequence $aa_{12}$-$aa_{13}$-$aa_{14}$-$aa_{15}$-$aa_{16}$-$aa_{17}$, and wherein $aa_{12}$ is selected from the group consisting of aspartic acid, glutamic acid, lysine, and glycine; $aa_{13}$ is leucine; $aa_{14}$ is glutamine; $aa_{15}$ and $aa_{16}$ are alanine; and $aa_{17}$ is leucine. Within a further embodiment the amino acid core sequence further contains the amino acid sequence $aa_{18}$-$aa_{19}$-$aa_{20}$, and wherein $aa_{18}$ is selected from the group consisting of tyrosine, phenylalanine and tryptophan; and $aa_{19}$ and $aa_{20}$ are selected from the group consisting of lysine, arginine, and glutamic acid. Within yet another embodiment the amino acid core sequence further contains the amino acid $aa_{21}$ selected from the group consisting of lysine, arginine, and glutamic acid.

Within another aspect of the invention antimicrobial peptides are provided comprising a peptide consisting of PMP-1 (Sequence No. 2), and truncations, retromers, extensions, combinations and fusions thereof, and D-isomeric amino acid, retromeric, N-monomethyl-lysine, and fluorinated amino acid derivatives thereof, the peptide having antimicrobial activity.

Within another aspect of the invention antimicrobial peptides are provided comprising a peptide consisting of PMP-2 (Sequence No. 1), and truncations, retromers, extensions, combinations and fusions thereof, and D-isomeric amino acid, retromeric, N-monomethyl-lysine, and fluorinated amino acid derivatives thereof, the peptide having antimicrobial activity.

The above described antimicrobial peptides can be utilized in a variety of methods, either alone or in combination with other ingredients excipients, against a variety of organisms such as bacteria and fungi. Within certain embodiments the peptide or peptide compositions of the present invention can have direct activity against, or, potentiate other microbial agents active against agents such as bacteria and fungi. Within related embodiments the peptides can potentiate antimicrobial activity of leukocytes against organisms such as bacteria and fungi.

Within certain embodiments of the invention, antimicrobial peptides CS-FBPa (ADSGEGDFLAEGGGVR) and CS-FBbb (EGVNDNEEGFFSA) are explicitly excluded from the formula or sequences provided herein.

The peptides and derivative metapeptides of the invention tested to date exert potent, broad spectrum antimicrobial activities in vitro, exhibit rapid microbicidal activities in vitro, can be used to potentiate conventional antimicrobial agents, to potentiate other antimicrobial peptides, are active against many organisms that exhibit resistance to multiple antibiotics, and enhance the antimicrobial functions of leukocytes. The peptides and derivative metapeptides of the invention can be designed to overcome problems of toxicity, immunogenicity, and shortness of duration of effectiveness due to biodegradation, retaining activity in plasma and serum, since they are based upon natural antimicrobial peptides that have lower inherent mammalian cell toxicities than conventional antimicrobial peptides. The peptides and derivative metapeptides of the invention also are linear, and have a low molecular mass, reducing the likelihood of producing immunogenic effects, since small linear peptides have a reduced likelihood of being immunogenic as compared with larger parent proteins. Many peptide designs are inherently resistant to proteolytic degradation, and exhibit stability in temperatures as high as 80° C., and in extremes of alkalinity and acidity, ranging from pH 2 to pH 10, for example. Substitutions of D- or other unusual amino acids into the peptide templates and derivative metapeptide design templates and their subsequent iterations may also increase their degradation time significantly, extending their half-life. Furthermore, these peptides are quite amenable to chemical synthesis and recombinant DNA expression techniques, facilitating their production in quantities necessary for use and evaluation in vitro, and eventual therapeutic applications.

These and other aspects and advantages of the invention will become apparent from the following detailed description, the accompanying drawings and sequence listing, which illustrate by way of example the features of the invention.

BRIEF DESCRIPTION OF THE DRAWINGS

FIG. 1 is a diagram of the design of RP-1, Sequence No. 3, from modeling of a microbicidal domain of PMP-2 (Sequence No. 1);

FIG. 12 is a chart of the primary structure of PMP-2, showing derivatives thereof;

FIG. 20 is a summary of the RP-1 in vitro spectrum of activity and potency;

FIG. 21 is a summary of the RP-8 in vitro spectrum of activity and potency;

FIG. 22 is a summary of the RP-11 in vitro spectrum of activity and potency;

FIG. 23 is a summary of the RP-13 in vitro spectrum of activity and potency;

FIG. 24 is a summary of the in vitro spectra of activity, potency and toxicity of the RP peptides at pH 7.2; and FIG. 25 is a summary of the in vitro spectra of activity, potency and toxicity of the RP peptides at pH 5.5.

DETAILED DESCRIPTION OF THE PREFERRED EMBODIMENTS

Figure 2A:
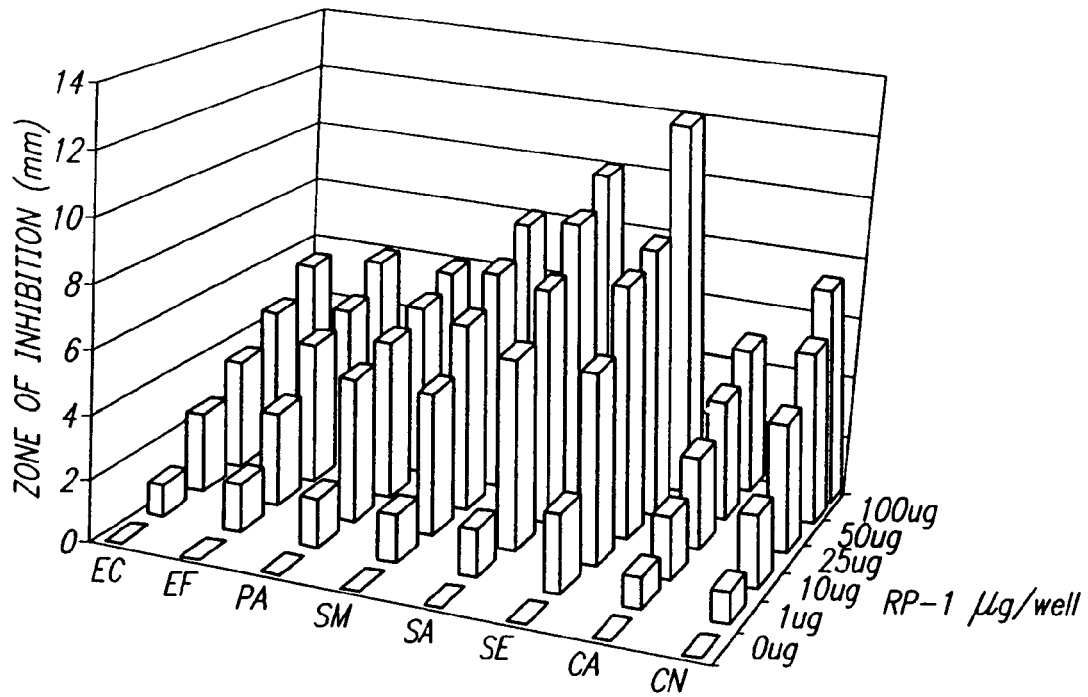
FIG. 2A is a three-dimensional graph of the antimicrobial spectra of RP-1, Sequence No. 3, in vitro (radial diffusion assay)

While natural antimicrobial peptides can be useful in combating pathogens exhibiting resistance to multiple antibiotics, either independently or in combination with antibiotic regimens or other antimicrobial peptides, conventional antimicrobial peptides have heretofore been viewed as being undesirably toxic, immunogenic, and/or short-lived.

Platelets contain potent antimicrobial peptides, termed platelet microbicidal proteins (PMPs). Our preliminary data support the concept that PMPs play a key role in platelet antimicrobial functions, and, therefore, in antimicrobial host defense. PMPs are locally released from platelets stimulated with microorganisms or agonists present at sites of endovascular infection. In vitro, PMPs exert rapid, potent microbicidal actions against a broad spectrum of relevant hematogenous pathogens, including *Staphylococcus aureus* and *Candida albicans*. Furthermore, organisms resistant to PMPs cause more severe infections in animal models than genetically-related counterparts. These facts demonstrate that PMPs are integral to antimicrobial host defense.

Our preliminary evidence indicates PMPs are released into the vascular compartment to act in antimicrobial host defense. Therefore, PMPs likely have structures which optimize antimicrobial activity, without concomitant mammalian cell toxicity. This distinguishes PMPs from neutrophil defensins, which are cytotoxic when released, and lose potent antimicrobial activity in this setting. Additionally, PMPs differ in mass and composition from cytotoxic defensins. PMPs exhibit potent antimicrobial activities against pathogens that are resistant to defensin hNP-1, and PMP mechanisms of action are distinct from that of hNP-1. Furthermore, PMPs exert significantly less cytotoxic effect on human vascular endothelial cells or erythrocytes as compared with hNP-1. These facts suggest PMPs have structure-function correlates that optimize antimicrobial activity relative to toxicity.

In addition to their direct microbicidal properties, it is highly likely that PMPs amplify multiple antimicrobial activities of neutrophils. Our preliminary data reveal that rabbit PMP-2 (Sequence No. 1) exhibits a C-X-C motif similar to those present in platelet factor-4 and interleukin-8 This determinant is a principal hallmark of α-chemokines that potentiate crucial neutrophil functions such as phagocytosis, chemotaxis, and oxidative burst. Our initial data suggest PMPs amplify in vitro phagocytosis and intracellular killing of *S. aureus* by rabbit neutrophils. Furthermore, PMP-2 (Sequence No. 1) exerts enhanced microbicidal activities under conditions of pH that exist in the neutrophil phagolysosome. These findings strongly suggest that certain PMPs may augment crucial neutrophil antimicrobial functions.

Our preliminary data provide a basis for our central discovery that PMPs have specific, independent determinants responsible for direct antimicrobial activities and potentiation of neutrophil antimicrobial functions. We have shown that these determinants can be isolated, optimized, and utilized to design novel mosaic peptides with selective antimicrobial properties. With a goal of designing novel therapeutics that have potent and selective antimicrobial functions and low toxicity, optimizing the activities of the distinct structural determinants in such peptides is essential. Our studies on PMP-2 (Sequence No. 1) are strategically based on our preliminary data: i) it or a precursor is released from platelets exposed to agonists present at local sites of endovascular infection; ii) it exerts potent microbicidal activity vs. relevant pathogens in vitro; iii) it exhibits a C-terminal domain analogous to known antimicrobial peptides; iv) it has an N-terminal C-X-C motif related to immunomodulatory α-chemokines; and v) it exerts significantly greater microbicidal activity at pH 5.5 vs. 7.2, suggesting it has enhanced and/or discriminative activity in neutrophil acidic phagolysosomes.

PMPs represent a unique opportunity to delineate structural determinants that likely govern discriminative antimicrobial host defense. Mosaic peptides discovered may also lead to development of novel anti-infective agents with selective or enhanced microbicidal and/or immunomodulatory activities against antibiotic-resistant pathogens. Thus, these peptides will additionally significantly advance our understanding of molecules that are likely central to host defense against infection, and may reveal important new strategies to potentiate antimicrobial host defense.

It is clear that platelets respond rapidly and are numerically significant at sites of endovascular infection, including infective endocarditis, suppurative thrombophlebitis, mycotic aneurysm, septic endarteritis, catheter and dialysis access site infections, and infections of vascular devices. We reason that platelet degranulation (e.g. PMP release) following sequestration of microorganisms likely produces potent and direct antimicrobial activities, and facilitates neutrophil antimicrobial functions.

The likelihood that platelets and PMPs play a crucial role in antimicrobial host defense in these and other settings has been demonstrated by the following facts: i) platelets are early and predominant cells at sites of microbial infection of vascular endothelium; ii) platelets target and internalize microbial pathogens; iii) platelets release microbicidal PMPs when stimulated with microorganisms or agonists integral to infection in vitro; iv) PMPs exert rapid and potent microbicidal activity against a broad spectrum of pathogens in vitro; v) PMPs exhibit structural motifs similar to α-chemokines that potentiate crucial neutrophil antimicrobial functions such as chemotaxis and oxidative burst; vi) a broad spectrum of microbial pathogens are damaged or killed by activated platelets; vii) thrombocytopenia increases susceptibility to and severity of diverse types of infections; and viii) mutant PMP-susceptible pathogens are less virulent in vivo as compared with PMP-resistant counterpart strains. Collectively, these facts suggest platelets are key to antimicrobial host defense, particularly through release of PMPs.

Interaction with neutrophils and monocytes provides an additional mechanism by which platelets and PMPs likely augment antimicrobial host defense. Platelets activated by microbes or other agonists release chemotactic stimuli for neutrophils and monocytes. Most important among these are the C-X-C chemokine platelet factor-4 (PF-4), platelet activating factor (PAF), or platelet derived growth factor (PDGF). A subcutaneous injection of PF-4 or PDGF rapidly promotes neutrophil infiltration in animal models. Intravenous injection of PAF into animals causes eosinophil infiltration into peribronchiolar tissues. Supportive of our discovery is the fact that PF-4 potentiates both neutrophil chemotaxis and microbicidal activity in vitro. The fact that PMP-2 (Sequence No. 1) is related to human platelet factor-4 strongly suggests PMP-2 (Sequence No. 1) shares these functions. Additionally, Jungi et al. found that monocytes and neutrophils avidly bind to activated platelets, but not to resting platelets. This interaction is mediated by P-selectin, GPIIb/IIIa, and/or thrombospondin expressed on activated platelets. Molecules generated from activated monocytes or neutrophils counter-activate platelets. For example, neutrophil superoxide, peroxides, halides, and myeloperoxidase promote platelet degranulation.

Important to our discovery, platelet factor-4 amplifies neutrophil fungicidal activity in vitro. Serotonin and $TXA_2$ released from platelet dense granules increase neutrophil adherence to vascular endothelial cells in vitro. Monocyte-derived IL-6 induces cytotoxicity of human platelets to *Schistosoma mansoni* larvae in vitro. Most recently, Christin et al. have demonstrated that platelets and neutrophils act synergistically in vitro to damage and kill *Aspergillus*. Collectively, these facts demonstrate that a relevant interplay exists linking platelet activation and degranulation with leukocyte activation in antimicrobial host defense. We reason that PMP-2 (Sequence No. 1) release from activated platelets is significantly involved in both the recruitment of neutrophils, and amplification of their antimicrobial functions.

Platelet antimicrobial functions are likely associated with release of potent antimicrobial peptides. In 1887, Fodor described the heat-stable bactericidal activity of serum, termed β-lysin, distinguished from heat-labile α-lysin complement proteins. Gengou showed that β-lysin bactericidal activity in serum was derived from cells involved in the clotting of blood. Hirsch later reported that platelets, not other leukocytes, reconstitute the bactericidal activity of platelet-free rabbit serum. Others have isolated cationic β-lysins from rabbit serum that are bactericidal against *S. aureus* or *B. subtilis*. Tew et. al. and Dankert et. al. showed that β-lysins and platelet associated bactericidal substances (PABS) were released from rabbit platelets stimulated with thrombin. Notably, Darveau et al. studied peptides related to human platelet factor-4 (PF-4) with antimicrobial capacity. The peptides disclosed herein differ both in origin and strategic modeling from these prior molecules, although some specific similarities exist. As detailed below, we have now isolated and characterized rabbit and human PMPs that likely significantly contribute to the antimicrobial effects of platelets.

Evidence is mounting in support of our discovery that platelets play an integral role in antimicrobial host defense. Thrombocytopenia (TCP) has been shown to be a significant, independent predictor of worsened morbidity and mortality in patients undergoing cytotoxic chemotherapy. In the absence of neutropenia, TCP correlates with increased incidence and severity of lobar pneumonia. Anti-platelet agents in the experimental endocarditis model significantly increase bacteremia and mortality. Moreover, Berney and others have demonstrated that neutropenia in the setting of normal platelet count does not diminish host defense against endovascular infection following antibiotic prophylaxis in vivo. These findings suggest platelets attenuate infection in vivo. Our studies in experimental animal models substantiate this concept.

Platelets have indisputable antimicrobial properties, and a compelling body of evidence strongly supports the concept that they are integral components in antimicrobial host defense. It is highly likely that the antimicrobial effects of platelets involve PMP release in response to relevant agonists present in the setting of infection. Thus, PMPs likely play a central role in host defense against infection through direct antimicrobial action, and potentiation of neutrophil antimicrobial functions.

Human PMPs have structural and functional congruence with rabbit PMPs. Much of our current knowledge about endovascular infections has been obtained using the experimental rabbit model. This model closely simulates vascular infections in humans. Thus, characterizing the structure-activity relationship in rabbit PMP-2 has enabled opportunities to elucidate the role of PMPs and platelets in host defense in rabbit or transgenic mouse models, as well as in humans. These long range goals may ultimately contribute to development of new therapeutic approaches in humans. Additionally, these investigations have uncovered new insights into host-pathogen relationships, and novel approaches to the prevention or treatment of infections, particularly those caused by pathogens which exhibit multiple drug-resistance phenotypes.

We have isolated PMPs from rabbit and human platelets subjected to acid extraction or thrombin stimulation. Thrombin is among the most potent platelet agonists elaborated in the setting of endovascular infection. Fractions of these preparations were screened for antimicrobial activity by acid-urea and sodium dodecyl sulfate polyacrylamide gel electrophoresis. All active fractions contained small, and cationic (PMPs). We then used reversed-phase high-performance liquid chromatography (RP-HPLC) to purify PMPs to homogeneity. We have since isolated a total of seven distinct PMPs from rabbit platelets. Five PMPs are recovered from acid-extracted rabbit platelets, and two distinct PMPs are predominant in thrombin-stimulated rabbit platelets. We have shown that microorganisms and microbial components are also capable of stimulating PMP release in vitro. These data indicate PMP release is linked to agonists generated by tissue damage and infection. We and others have demonstrated that human platelets contain microbicidal peptides analogous to rabbit PMPs. These results provide evidence for interspecies conservation of PMPs in mammalian platelets, underscoring their likely role(s) in antimicrobial host defense.

Recent evidence implicates platelets and PMPs in host defense against infection in vivo, using two complementary approaches. We have examined the role of platelets in defense against a PMP-susceptible (PMP$^S$) viridans streptococcal strain in experimental infective endocarditis in animals either with normal platelet counts, or those with selective immune TCP. Thrombocytopenic animals had significantly higher streptococcal densities in vegetations as compared with their counterparts with normal platelet counts. Dankert et al. have also implicated platelet-derived molecules as active in host defense against infective endocarditis. These data suggest that platelets and PMPs are important in limiting the induction and evolution of endovascular infection.

Complementary to the above approach, we recently demonstrated that, for *S. aureus* or *S. epidermidis*, a positive correlation exists between infective endocarditis source and in vitro resistance to tPMP-1. These findings indicate PMP$^S$ organisms are less able to propagate endovascular infection in humans as compared with PMP$^R$ isolates. Parallel findings suggest *Salmonella* resistance to defensins corresponds with increased virulence in vivo. Evidence also exists substantiating the likelihood that PMPs participate in the observed antimicrobial function of platelets in vivo. We have shown that susceptibility to tPMP-1 negatively influences the establishment and evolution of *S. aureus* of *C. albicans* infection. In the rabbit model, PMP$^S$ *C. albicans* exhibits significantly less proliferation in cardiac vegetations, and dramatically reduced incidence of splenic dissemination as compared with a related PMP$^R$ strain. Similarly, we have demonstrated that in vitro phenotypic resistance to tPMP-1 correlates with enhanced virulence in experimental endocarditis due to *S. aureus*. These results suggest that the host defense function of platelets involves PMP elaboration at sites of infection.

We have also shown that PMPs exert relevant and potent microbicidal activities against bloodborne pathogens in vitro. We have defined the microbicidal activities of purified PMPs and tPMPs. Nanomolar concentrations of these peptides exert rapid, potent in vitro microbicidal effects against *S. aureus, S. epidermidis*, viridans group streptococci, *Escherichia coli* (1-5 µg/ml), and a variety of other bacterial pathogens. We have also demonstrated that PMPs and tPMPs are fungicidal in vitro to *C. albicans* and *Cryptococcus neoformans*, suggesting their broad antimicrobial spectra. These peptides are microbicidal in physiological ranges of pH (5.5 to 8.0), and in the presence of plasma or serum. Thus, the antimicrobial activities of PMPs observed in vitro are relevant to conditions known to exist in vivo, as discussed below. Furthermore, we have demonstrated that PMPs are released from platelets stimulated with agonists present in the setting of endovascular infection, including *S. aureus* and *C. albicans*, staphylococcal α-toxin, or thrombin. These findings suggest certain PMPs are released from platelets in response to tissue trauma, soluble mediators of inflammation, or pathogens themselves. Therefore, PMPs are likely to be introduced into the vascular compartment in a localized manner to participate in antimicrobial host defense. We reason that PMPs have structural features that optimize their microbicidal activity and interaction with complementary antimicrobial host defense mechanisms (e.g., neutrophils), without concomitant host cell toxicity. Thus, our discovery is that structural determinants in PMPs significantly influence their microbicidal and/or neutrophil-modulatory activities and/or selectivity. The current application is based on derivation of novel peptide sequences based in part on those present in one or more PMPs or tPMPs.

PMPs differ in structure from other endogenous antimicrobial peptides. We have used mass spectroscopy to confirm that PMPs range from about 6.0 to 9.0 kDa. Compositional analyses reveal that PMPs and tPMPs contain high proportions of basic amino acids lysine, arginine, and histidine (total content about 25%); this composition is consistent with their cationic charge. Notably, mass, cystine array, and lysine content differentiate PMPs and tPMPs from neutrophil defensins. Additionally, PMPs and tPMPs are distinguished from platelet lysozyme by mass, composition, and antimicrobial activity. Performic acid-oxidization reveals that PMPs and tPMPs have two to four cystine residues. We have also found that two cystine residues in PMP-2 are aligned in a C-X-C motif, characteristic of α-chemokines that stimulate neutrophil response, as discussed below. Together, these findings suggest there are structural features in PMPs and tPMPs that are integral to their direct microbicidal activities and/or abilities to influence neutrophil antimicrobial functions, discussed below.

Our preliminary structural data suggest PMPs and tPMPs exhibit similarities to and differences from other endogenous antimicrobial peptides. Similarities of PMPs to other antimicrobial peptides include: i) composition rich in basic amino acids corresponding to cationic charge, ii) broad antimicrobial spectra in vitro; iii) potent microbicidal activity (nanomolar); and iv) disruption of microbial cytoplasmic membranes involved in their mechanisms of action, discussed below. In contrast, PMPs and tPMPs have structural characteristics that clearly distinguish them from other antimicrobial peptides. For example, defensins are 29 to 34 amino acid peptides of about 3 to 4 kDa mass. Similarly, amphibian magainins and insect cecropins range in mass from about 2.5 to 4.5 kDa. PMPs and tPMPs are considerably larger (6.0-9.0 kDa). Furthermore, neutrophil defensins have three invariate cystine residue pairs mediating disulfide bridges. These intramolecular bridges stabilize defensins, conferring their characteristic amphiphilic turn-sheet-helix conformations.

Magainins or cecropins lack such tertiary structure. However, the primary structures of these latter molecules induce amphiphilic α-helical motifs analogous to those of defensins. In comparison, PMPs 1-5 each contain 3-4 cystine residues, similar to defensins, while tPMPs 1 and 2 contain only 2 or 3 cystine residues, respectively. These findings indicate PMPs have unique structural features related to their selective and unique antimicrobial activities.

PMPs and tPMPs target and disrupt microbial cytoplasmic membranes. We have investigated morphologic consequences of rabbit PMP-2 and tPMP-1 exposure to bacterial cells, protoplasts, and lipid bilayers in vitro using transmission electron microscopy (TEM) and biophysical techniques. Rapid cytoplasmic membrane disruption, followed by cell wall swelling, occurs in S. aureus after exposure to 10 μg/ml PMP-2 or tPMP-1 for as little as 15-60 min. Ultrastructural damage precedes detectable bactericidal and bacteriolytic effects. Fungal pathogens are likewise damaged by these peptides in vitro, S. aureus protoplasts exhibit similar damage, indicating membrane injury is independent of the presence of cell wall. We have also demonstrated that PMPs produce these effects through a selective mechanism of voltage-dependent membrane permeabilization, as discussed below. These ultrastructural findings suggest that one primary target of PMP action is the microbial cytoplasmic membrane. It is important to reiterate that PMPs are likely released into the bloodstream in response to infection, such that they presumably accumulate locally at sites of infection to act directly and indirectly in antimicrobial host defense. This suggests PMP structural determinants optimize microbicidal activity, and minimize host cytotoxicity, underscoring the importance of understanding structure-activity relationships in PMPs.

PMPs exhibit structural features likely related to their antimicrobial functions. We have used complementary N-terminal sequencing and PCR technology to show that PMPs include novel peptides, and peptides not previously known to be microbicidal. Thus, our proposed characterization of the PMP structural determinants that mediate their antimicrobial functions has provided information not previously attainable. Several exciting findings have emanated from our studies of PMP structures. Amino acid sequences of rabbit PMPs 1 and 2 indicate that the initial 24 residues present in PMP-1 are identical to those previously known for rabbit rPF-4. Thus, we have tentatively identified PMP-1 as rPF-4, Furthermore, our preliminary sequencing of the majority of the 74 amino acid residues in native PMP-1 and PMP-2 reveal novel structural data regarding rPF-4. In addition, our preliminary data indicate that PMP-2 is a variant of PMP-1, differing in a glycine-to-arginine substitution at PMP-2 residue 25. This suggests PMP-2 is a novel microbicidal analogue of rPF-4. We have found that PMPs-1, -2, and -4 exhibit a cystine-variable-cystine (C-X-C) motif characteristic of the α-chemokines integral to neutrophil stimulation. We have given particular attention to the C-X-C motifs in PMPs. Clearly, C-X-C chemokines such as human PF-4 (hPF-4) potentiate neutrophil chemotaxis, phagocytosis, and microbicidal activities in vitro. The fact that PMP-2 has the C-X-C motif demonstrates that it potentiates neutrophil antimicrobial functions, in addition to its direct microbicidal action. This rationale underscores the approach we have taken to differentiate effects of PMP-2 structural determinants on neutrophil antimicrobial activities as discussed below. In addition to rabbit PMPs, we have isolated and characterized the structures of analogous human PMPs. Sequence analyses indicate that human PMPs include: hPF-4; connective tissue activating protein-III (hCTAP-III); thymosin β-4 (hT β-4); platelet basic peptide (hPBP); RANTES (hRANTES); fibrinopeptides A and B (hFP-A and hFP-B; 4.5), and truncations or fragments of these peptides. Like rabbit PMPs, human PMPs exert rapid and potent in vitro microbicidal activities against S. aureus, E. coli, and C. albicans. Furthermore, several of these peptides (e.g., hPF-4) possess a C-X-C motif analogous to rabbit PMP-2. Together, these structural and functional similarities indicate close homologies among rabbit and human PMPs. This evidence further substantiates our rationale to study rabbit PMP-2 as a means of developing novel antimicrobial peptides, and as a model for future investigation of role(s) of human PMPs in antimicrobial host defense.

Our recent studies have provided new evidence that PMPs differ in mechanisms of action from those of other antimicrobial peptides. We used flow cytometry to study the mechanisms of action of PMPs against S. aureus strain pair 6850 ($PMP^S$) and JB-1 ($PMP^R$) in vitro. Strain JB-1 is a menadione auxotroph of parent strain 6850, and has a decreased transcytoplasmic membrane potential ($\Delta\Psi$). We used the fluorescent probes dioxycarbocyanine ($DiOC_5$) and propidium iodide (PI) to quantify the effects of PMP-2 and human defensin NP-1 (hNP-1) on $\Delta\Psi$ and permeability, respectively. PMP-2 rapidly depolarized, permeabilized, and killed the $PMP^S$ strain; this activity was significantly greater at pH 5.5 vs. pH 7.2. Depolarization, permeabilization, and killing of the $PMP^R$ strain by PMP-2 was significantly less than the $PMP^S$ strain. Menadione reconstituted the $PMP^R$ strain $\Delta\Psi$ to a level equivalent to the $PMP^S$ strain. This was associated with increased depolarization, permeabilization, and killing of the $PMP^R$ strain due to PMP-2. Therefore, the mechanism of PMP-2 action involves rapid, pH-dependent membrane permeabilization with membrane depolarization. These effects were different from hNP-1, or the cationic antibacterial agents protamine or gentamicin. For example, membrane permeabilization due to hNP-I was equivalent in the $PMP^S$ and $PMP^R$ strains, and greater at pH 7.2 than at pH 5.5. Collectively, these data suggest PMPs exert mechanisms of action which differ from hNP-1. These findings imply that specific structural determinants significantly influence PMP microbicidal activities. Similarly, we have recently found that PMPs are active against Salmonella typhimurium strains resistant to hNP-1. For example, parental strain 14028, intrinsically resistant to hNP-1, was as susceptible to PMP-2 as hNP-1 hypersusceptible strains 4252s and 5996s. These data further support the discovery that PMP microbicidal mechanisms differ from hNP-1.

Preliminary data suggest PMP-2 amplifies neutrophil antimicrobial functions in vitro. We have initially studied the influence of PMP-2 on in vitro neutrophil phagocytosis and intracellular killing of S. aureus. In our preliminary experiments, a heterologous system was established employing human neutrophils, pooled normal human serum, or crude rabbit PMP-2. Organisms ($5 \times 10^7$/ml) were pre-exposed to sub-lethal concentrations of serum or PMP-2 for 30 minutes, washed, mixed with neutrophils (20:1), and incubated at 37° C. for 2 hours. We observed a significant increase in phagocytosis of S. aureus when pre-exposed to PMP-2 (mean organisms/neutrophil=11.2), as compared with serum (mean organisms/neutrophil=6.4) or buffer control (mean organisms/neutrophil=3.7; P<0.05 for PMP-2 vs. serum or buffer). To quantify intracellular killing, neutrophils were lysed, and aliquots quantitatively cultured to enumerate surviving S. aureus cells. Initial results suggest PMP-2 enhances intracellular killing of S. aureus at the 2 hour time point. For example, only 23.8% of PMP-2-exposed cells survived, while 64.1% of the serum exposed, and 78.6% of the buffer control cells survived at this time point (P<0.05 for PMP-2 vs. serum or buffer control). These data support our central discovery that PMP-2 augments antimicrobial functions of neutrophils. The fact that PMP-2 exhibits a C-X-C chemokine domain that likely promotes neutrophil chemotaxis further justifies our rationale that PMP-2 specific determinants amplify these neutrophil functions (see below).

PMP-2 exhibits sequences homologous to chemokine and microbicidal domains. Recent advances in structural analyses have revealed important new information regarding structure-activity correlates among antimicrobial peptides. For example, it is now known that many antimicrobial peptides are small, cationic, and have amphiphilic α-helical domains. We have compared PMP-2 and known microbicidal peptide sequences to predict structural features that are likely integral to PMP-2 microbicidal activity. These studies revealed that PMP-2 has many hallmarks of microbicidal peptides, including: 1) periodic amphiphilic domains; 2) relatively high hydrophobic moment ($M_H$); and 3) charge-clustering. Additionally, we found that PMP-2 possesses a C-X-C motif similar to that found in immunomodulatory chemokines. To test whether we could isolate and differentiate microbicidal domains from PMP-2, we employed solid-phase F-moc" chain assembly to synthesize a novel peptide derived from amino acids 46-63 of PMP-2 (PMP-$2_{46-63}$) (FX-PMP-2-46-63, Sequence No. 36) with the following sequence: $H_2N$-ATKKNGRKLCLDLQAAL-COOH. In preliminary structural analyses, we have found that PMP-$2_{46-63}$ (Sequence No. 36) reflects the conformation of the same domain in native PMP-2 (Sequence No. 1) as is explained further below. Moreover, PMP-$2_{46-63}$ (Sequence No. 36) exerts the selective microbicidal properties characteristic of PMP-2 (Sequence No. 1), that are significantly amplified at pH 5.5 as compared to pH 7.2. Thus, the structure-activity relationship in PMP-$2_{46-63}$ (Sequence No. 36) mirrors that of native PMP-2 (Sequence No. 1).

We have integrated conventional structural analysis with molecular modeling in our preliminary studies of PMP-$2_{46-63}$ (Sequence No. 36). Purification by RP-HPLC reveals that synthetic PMP-$2_{46-63}$ (Sequence No. 36) elution is consistent with an amphiphilic, cationic peptide. The fact that PMP-$2_{46-63}$ (Sequence No. 36) RP-HPLC elution time is about 8 min earlier than PMP-2 (53.5 minutes) under identical conditions corresponds with reduced hydrophobicity of PMP-$2_{46-63}$ (Sequence No. 36). We have confirmed that purified synthetic PMP-$2_{46-63}$ (Sequence No. 36) has the correct sequence and mass by Edman-degradation and MALDI-TOF mass spectroscopy, respectively (MW=1842.2 Da; predicted=1842.3 Da). These data confirm the feasibility of our proposed approaches: we have identified, synthesized, purified, and evaluated a microbicidal domain of PMP-2 (Sequence No. 1).

We have investigated PMP-$2_{46-63}$ (Sequence No. 36) secondary conformation by Fourier-transform infrared (FTER) spectroscopy. Multi-scan FTIR was performed on PMP-$2_{46-63}$ (Sequence No. 36) suspended in 0.01% acetic acid adjusted to pH 5.5 or 7.2, and with or without palmityl-oleoyl-phosphatidyl-glycerol (POPG in hexachloroisopropanol) as simulation of a prokaryotic lipid membrane. In aqueous solution at pH 5.5 or 7.2, these preliminary studies revealed a strong peak at 1629 $cm^{-1}$ indicating that PMP-$2_{46-63}$ (Sequence No. 36) exists in a β-sheet conformation. However, in POPG, PMP-$2_{46-63}$ (Sequence No. 36) undergoes dramatic conformation shift to a (β-turn/hairpin structure, exhibiting a peak at 1675 $cm^{-1}$. These results indicate PMP-$2_{46-63}$ (Sequence No. 36) likely undergoes a conformational shift when it interacts with the bacterial membrane.

Molecular modeling of PMP-$2_{46-63}$ (Sequence No. 36) corroborates conventional structural analyses. Our preliminary work to model the solution structure of PMP-$2_{46-63}$ (Sequence No. 36) followed a multistep algorithm designed to predict the conformation of this and other peptides. This algorithm uses a serial four-step approach. First, multiple methods (e.g., Chou-Fasman analyses) were employed to seek regions of consensus in the predicted secondary structure. Next, we searched the Brookhaven protein database for known sequences with homology to PMP-$2_{46-63}$ (Sequence No. 36) (e.g., PF-4). Resulting peptides were screened, and those lacking consensus secondary structure were excluded. The remaining peptides were used as templates for PMP-$2_{46-63}$ (Sequence No. 36) backbone trajectory. We then used molecular mechanics to allow each theoretical model PMP-$2_{46-63}$ (Sequence No. 36) to relax to corresponding energy minima. Molecular dynamics were then used to test conformer stability, and the average conformer was minimized using molecular mechanics. Three conformers of PMP-$2_{46-63}$ (Sequence No. 36) were initially identified. Two of these were similar sheet-turn-sheet motifs (forming a hairpin loop with C- and N-termini in close proximity); another was a helical rod. The loop structures were both stable in molecular dynamics. The helical rod rapidly collapsed (within 100 psec of simulation time) into a hairpin-like structure and thus was excluded as a model candidate. After minimization, all models were similar, with <1 Å rms difference between backbone atoms. Extended regions of PMP-$2_{46-63}$ (Sequence No. 36) were extensively H-bonded. To confirm the predictive accuracy of this approach, the first three steps of this algorithm have been used on selected peptides (15 residues) of known conformation. Selected test peptides (with known structures) were removed from the Brookhaven database so they would not self-recognize in the search. Predicted conformers achieved through the above approach closely resembled experimentally determined structures (rms deviations of ≤3.5 Å). Thus, our knowledge-based algorithm is reliable, and corroborates the predictive value of our proposed modeling strategies.

In addition to the knowledge-based algorithm described above, we have also used energy-based methods, We used systematic and Monte Carlo searches of the Ramachandran angles (φ and ψ) of PMP-$2_{46-63}$ (Sequence No. 36). We found multiple minima on its energy surface, indicating that several conformers were possible. However, the molecular dynamics simulations demonstrated that the only stable conformer was that of the hairpin loop. In more extended simulations (10 nsec), the peptide oscillated about the hairpin structure as judged by radius of gyration and Ramachandran angles. The result suggests that the energy barrier between conformers is high, and that one conformer predominates or is exclusive. This conformer was the same as that identified by the knowledge-based algorithm described above. In addition, these modeling studies predicted that the – and C-terminal regions are extended structures, with a short helical span central to the peptide. These findings corroborate the β-sheet-turn-β-sheet structure suggested by our FTIR analyses. Preliminary modeling of PMP-$2_{46-63}$ (Sequence No. 36) also predicts structural features likely integral to antimicrobial activity. For example, the electrostatic distribution analysis of PMP-$2_{46-63}$ (Sequence No. 36) indicates that its charge is longitudinally polarized (e.g., strongly cationic C-terminus with a relatively non-charged N-terminus). Furthermore, PMP-$2_{46-63}$ (Sequence No. 36) exhibits substantial periodic amphiphilic and hydrophobic clustering. Segregation of charge and hydrophobicity are peptide motifs associated with microbicidal activity. Therefore, our preliminary molecular modeling data reveal a likely structure-activity relationship in the microbicidal domains of PMP-2 (Sequence No. 1).

It is important to note convergence of the predicted and determined PMP-2$_{46-63}$ (Sequence No. 36) conformations from multiple starting points. These findings correspond with FTIR data, indicating that PMP-2$_{46-63}$ (Sequence No. 36) has an anti-parallel strand structure with a short helix forming the connecting region. This agreement among two modeling algorithms and experimental and FTIR data indicate the conformer identified is the likely solution structure for PMP-2$_{46-63}$ (Sequence No. 36). The next logical step would be to model PMP-2$_{46-63}$ (Sequence No. 36) at the surface of a lipid bilayer.

Overall, these data indicate several important features substantiating the utility of our proposed molecular modeling strategies. First, we have gained important insights into the fundamental structure-activity relationship in PMP-2$_{46-63}$ (Sequence No. 36); these consistently translate to PMP-2. Thus, we are poised to define the precise structural determinants in PMP-2 using these methods. Importantly, the predicted PMP-2$_{46-63}$ (Sequence No. 36) conformer is not obvious from the primary structure. Nonetheless, our experimental data corroborate our modeling data. In addition, the consistency in prediction of the same motifs by both energy- and knowledge-based strategies suggests this conformational preference is genuine. These relationships underscore a major advantage achieved through our integration of conventional structural analysis and molecular modeling: crucial structure-activity relationships may go undetected if either strategy were to be used exclusively.

A basic peptide is expected to have especially strong interactions with bilayers of acidic phospholipids (e.g., those bearing phosphatidylglycerol and phosphatidylserine head groups). The strong matrix of net negative charge will act as a cation exchanger for basic peptides to be investigated in this work. Thus, only the interaction between the polar phospholipid head groups and PMP-2 determinants can be simulated to focus computational resources. Lipid environments (bilayers) simulating prokaryotic or eukaryotic membranes can be tested for interaction with peptides. Two-dimensional grids of diacetylphosphatidylglycerol or diacetylphosphatidylserine molecules can be generated. In the primary simulation, PMP-2 conformers corresponding to local minima (as described above) can be manually docked to the polar surface of this grid using the SYBYL algorithm DOCK. Molecular mechanics and molecular dynamics can then be used to estimate the influences of the phospholipid charge array on peptide conformation. This will also estimate the attraction of a peptide for the phospholipid head group, revealing insights into peptide/target-cell selectivity. Solvent can be assigned as a distance-dependent dielectric function. Initially, phospholipids can be fixed as an immovable aggregate; conformational transitions of PMP-2 determinants can then be simulated using molecular mechanics and molecular dynamics as above. In complex secondary models, a phospholipid array can form one wall of a cube comprised of a PMP-2 determinant TIP water, and counter ions (e.g., NaCl) when appropriate, and phospholipids initially fixed as before. In other simulations, with and without explicit solvent, flexibility of the polar head groups can be allowed. In this case, the phospholipids can be anchored by the methyl groups on the acyl chains. We recognize there are limitations to these simulations, and potential pitfalls can be minimized as pointed out by Jakobsson. These methods have been successfully used to characterize peptide-lipid interactions by numerous investigators.

Analytical ultracentrifugation can be used to study hydrodynamic shape, predicted radius of gyration, and therefore, overall fold of the peptide. As important, centrifugation can ascertain the degree of self-association of the peptide under the conditions used to assay its activity. Self-association may occur through either open association (aggregation increases continually with peptide concentration), or closed association (the peptide reaches a definite, multimeric state). Knowledge of the aggregation state is essential for complete interpretation of both the physical and biological data. Experimental results can be compared to models; accuracy of the comparisons can be well within the range to make qualitative differentiations (e.g., helical rod, folded helix, hairpin, antiparallel β-sheets, random coil). The advantage of analytical ultracentrifugation is that all measurements come directly from first principles; thus, they do not rely on standards (as do most common analytical techniques). Additionally, only small quantities of peptide are required, and the technique is non-destructive.

The following relationship can be employed in these investigations:

$$s=M(1-vp)/Nf$$

where s is the sedimentation coefficient, v is the partial specific volume, p is the density of the solution, N is Avogadro's number, and f is the frictional coefficient. The frictional coefficient (f) is given by $$f=6p\eta R_s$$

where η is the viscosity and $R_s$ is the Stokes radius. The diffusion coefficient (D) is given by $$D=RT/f$$

where R is the gas constant and T is the temperature in degrees Kelvin. Therefore, Stokes radii can be obtained by measurement of either sedimentation coefficient or diffusion coefficient. Both can be determined in the centrifuge, and in favorable cases, in a single experiment. Self-association can be determined from sedimentation equilibrium experiments, with the general relationship determined by the equation: $M=[2RT1/w^2(1-vp)][d\ln(c)/dr^2]$. In the absence of self-association, a plot of ln(c) vs. $r^2$ is linear. In the presence of self-association, the line can be concave upward. The slope of the line is analyzed and can be used to determine the propensity of the peptide to self-associate using the computer program ORIGIN. Because of the large diffusion coefficients of small peptides, synthetic boundary centerpieces can be used to obtain an initial sharp boundary between peptide and solvent. Band forming centerpieces can be used depending on preliminary results. The initial concentrations of peptide may vary between 0.01 and 100 μlg/ml. Diffusion coefficients can be obtained from boundary spreading experiments. While these can be obtained from the high-speed synthetic boundary experiments, generally the determinations can be made at low speed where sedimentation will be small. Initially, the rotor speed can be set low, and adjusted upward during the experiment depending on the determined concentration gradient. In this way a range of concentrations can be generated in a single experiment, and any pressure dependencies can then be identified. Due to the high diffusion coefficient of the peptides, equilibrium can be attained rapidly. Equilibrium can be defined as lack of a detectable difference in measurements of the concentration gradient taken 1 hour apart.

In cases where self-association of peptide is observed in the analytical ultracentrifuge, chromatography can be used to extend analysis to lower concentrations which may be more relevant to those used for measurement of biological activity. The total volume of a column $V_T=V_0+V_i+V_g$, where $V_0$ is the void volume, $V_i$ is the interior volume, and $V_g$ is the volume of the chromatographic matrix. The elution volume $V_e = V_0 + KV_1$, where K, the distribution function, vanes between 0 and 1. The advantage of gel permeation chromatography is the ease of use, less interference from buffers, and the lower concentrations of peptide that can be analyzed. The disadvantage is that the column must be calibrated with standards of known Stokes radii. Guided by our initial experiments, Sephadex GI0, G15 or G25 (or corresponding Sepharcyl matrices) can be used as the chromatographic matrix. Chromatography can be conducted at constant temperature using an automated fraction collector, and peptide detected by optical absorbance. When peptide concentrations are low or the buffers strongly absorbing, peptide can be detected by reaction with fluorescamine or other reagents, which we can detect in the femtomolar range. The combination of analytical ultracentrifugation and gel permeation chromatography will allow experimental verification of predicted peptide conformations, and detection of any anomalies, such as self-association, that influence interpretation of the spectroscopic and biological findings.

The conformational status of PMP-2 determinants and other peptides can be determined using circular dichroism (CD) and/or Fourier-transform infrared (FTIR) spectroscopy as previously described. CD can be principally used to assess helicity, and FTIR has advantages in determining β-sheet structures. Purified peptides can be solubilized to a concentration of 50 µg/ml in 50 mM $NH_4HCO_3$. Buffer-subtracted CD spectra (190-250 nm) can be obtained from an average of three 25° scans, using a mean residue ellipticity based on a mean residue mass of 110 daltons. Attenuated total reflectance (ATR) crystals of selected peptides can be produced by adsorption of 500 picomoles onto aluminized mylar, coated with nitrocellulose. FTIR spectra can be recorded at an accelerating voltage of 16 kV at 16000 nanosecond intervals, and analyzed using peak search software.

We have developed novel tools for studies to examine PMP antimicrobial activities. As described above, we have recently utilized the rabbit model of infective endocarditis to explore the host defense properties of platelets and PMPs in vivo. Additionally, we have recently developed pathogen strain pairs that differ in susceptibility to PMPs. These organisms have facilitated our investigations into the mechanisms of PMP action, and studies to evaluate the role of PMPs and platelets in host defense against infection. The panel of organisms we have developed include both isogenic S. aureus and C. albicans strain pairs which differ in PMP susceptibility. We generated these strain pairs in two ways. First, we developed PMP-resistant ($PMP^R$) strains from susceptible ($PMP^S$) parental strains by serial passage through high concentrations of PMPs in vitro. We then compared these strains (S. aureus $19^S/19^R$; C. albicans $36082^S/36082^R$) by restriction mapping, immunoblotting, and phenotypic characterization in vitro and ex vivo. Strains were indistinguishable by these techniques other than in PMP susceptibility. We have also developed a panel of $PMP^R$ S. aureus strains by transposon mutagenesis of $PMP^S$ strain ISP479 engineered to possess the transposon Tn 551 in a pI258 vector. We identified a clone (ISP479R) with a stable tPMP-$1^R$ phenotype after serial passage in broth media and rabbit serum (>85% survival after 2 hour exposure to 10 µg/ml tPMP-1, vs. <10% survival of the parental strain). The $PMP^R$ phenotype in this strain was also stable after in vivo passage in the rabbit. EcoRI and NcoI restriction analyses and Southern hybridization were used to confirm that ISP479R contained a single Tn 551 insert, localized within the same restriction fragment pre- and post-in vitro and in vivo passage. The related strain iSP479C, cured of the plasmid containing the pI258 vector, completes the control organisms in this S. aureus strain panel. We have studied this panel extensively in the rabbit model of infective endocarditis. In doing so, we have now demonstrated that artificially-induced resistance to PMPs confers a survival advantage to organisms in the context of endovascular infection in vivo. Thus, susceptibility to PMPs is undoubtedly a significant parameter in overall antimicrobial host defense. Studies beyond the scope of the current application are under way to define the precise influence of PMP resistance in various animal models. Strain pain such as these are also crucial to future studies to define mechanisms of PMP action, and the genetic elements in pathogens that may be responsible for resistance to PMPs and/or other antimicrobial peptides. In addition, relevant and well characterized strains available from the American Type Culture Collection (ATCC) will be important tools with which we can evaluate the potencies of our novel peptides against drug-resistant pathogens.

Designs of Novel Antimicrobial Peptides

Our preliminary data strongly support our central hypotheses: i) PMP-2 (Sequence No. 1) exerts direct antimicrobial activities linked to its specific structural determinants; ii) PMP-2 (Sequence No. 1) potentiates crucial antimicrobial functions of neutrophils likely due to structures such as C-X-C; iii) structure-activity relationships in PMP-2 (Sequence No. 1) antimicrobial determinants can be isolated and modeled, enabling design of novel peptides and mosaic peptides that achieve highly potent and/or selective antimicrobial activities.

In this regard, a defined set of analogues can be synthesized, characterized, and assessed by the above screens for antimicrobial activity. These approaches have been used to identify specific structural determinants in PMP-2 responsible for direct antimicrobial activities. First, truncated versions of PMP-2 domains have been synthesized. Next, compositions of these domains can be strategically varied to define the specific determinants responsible for their antimicrobial activities as described above. Criteria for selection can include exceptional antimicrobial activity and/or selectivity. Furthermore, combinatorial peptides can be synthesized at the 0.01 nmol scale by simultaneous peptide synthesis methods.

Systematic peptide truncation can be used to define domain size essential for antimicrobial activity. In addition, peptides of reduced chain length may be advantageous as therapeutic agents as compared with larger proteins: 1) smaller peptides typically have greater distribution via more efficient diffusion; 2) they are generally less immunogenic than larger peptides; and 3) shorter peptides tend to be less susceptible to proteolytic degradation than comparable larger proteins. Thus truncated analogues of PMP-2 functional domains have been synthesized, including N-terminal, C-terminal, or dual-terminal truncations using combinatorial synthesis (e.g., see Sequence Nos. 30, 31, 32 and 33).

We have noted that charged, hydrophobic, and aromatic amino acid residues dramatically influence peptide antimicrobial activities. Due to this relationship, peptide libraries can be derived from selected templates to vary peptide parameters believed integral to antimicrobial activity individually or in combination: 1) conformation; 2) charge density and periodicity; 3) amphiphilic density and periodicity; 4) hydrophobic moment ($M_H$); 5) mass-to-charge ratio; and 6) terminal orientation, 1. Charge-Conservation, Neutralization, or -Reversal: Antimicrobial peptide potencies may vary relative to steric properties of charged amino acids. Alternatively, net charge may dramatically influence peptide activity. Therefore, charged amino acids can be substituted such that overall charge can be conserved, but varied sterically (e.g., lysine-to-arginine), neutralized (e.g., lysine-to-glycine), reversed (e.g., lysine-to-glutamic acid), or a combination of these approaches.

2. Non-Polar Substitution: Hydrophobic amino acids leucine, alanine, isoleucine, and valine are common residues among antimicrobial peptide sequences. These residues likely have a significant impact on hydrophobic density and mean hydrophobic moment ($M_H$) as they relate to peptide antimicrobial activity. Thus, peptides can be designed with non-polar substitution (e.g., leucine-to-isoleucine) and/or conversion (e.g., valine-to-glycine) to assess the influence of polarity in amino acids on antimicrobial activities of PMP-2 structural domains.

3. Aromatic Substitution: Aromatic amino acids such as tyrosine, phenylalanine, and tryptophan directly influence mean hydrophobic moment and hydrophobic density. In addition, their molecular radii significantly influence the steric properties of peptides. These parameters are believed crucial to peptide microbicidal activity. Therefore peptides derived from PMP-2 structural domains can be assessed with aromatic substitutions for their antimicrobial activities, such as tryptophan-for-tyrosine, and phenylalanine-for-tyrosine scanning.

4. Retromer Peptides: Stereo-specificity likely plays an important role in peptide-target cell interaction. However, previous studies have shown that L- and D-isomer peptides are indistinguishable in their antimicrobial activities. Therefore, selected PMP-2 domains exhibiting potent or selective antimicrobial activities can be synthesized as retromers, and tested as above to assess the influence of terminal orientation on such activities.

The relative rates of modification of amino acid side chains can provide information about accessibility and dynamics of many of the study peptides. Thus, synthetic analogues of selected peptides found to have exceptional or unique antimicrobial activities can be studied to further define their structure-activity relationships, as outlined below, and used to design subsequent peptide iterations.

1. Conformer-Restriction Amino Acid Substitution. An excellent method of conformational control is to replace selected amino acids in the original peptide with amino acids that will restrict the motion of the peptide chain. In selected peptides, proline, β-branched, N-methyl, α,β-dehydro (unsaturated bond between the α and β carbons), α,α-dialkyl, and/or D-amino acids can be placed at positions allowed or preferred, where Ramachandran $\phi$ and/or $\psi$ torsional angles are compatible with the predicted peptide backbone trajectories. Both protein and non-protein amino acids can be introduced in combinatorial synthesis of the peptides. In this way, use of amino acids with restricted $\phi$ and $\psi$ angles will create more active analogs, since these modifications will favor the conformer with the desired antimicrobial activity.

2. Disulfide-Bridge Conformer Stabilization. We have used the cystine cross-linking method to verify the predicted conformation of an insect neuropeptide. Precise and restricted geometries of disulfide bonds make engineering of these crosslinks rigorous tests of peptide conformation. Measurement of the rates of disulfide formation in the reduced peptide, along with comparison of biological activity in oxidized and reduced states provide additional tests of the predicted conformation and activity relationship. Therefore, selected peptides can be synthesized to contain cystine residues in strategic locations to facilitate disulfide bridge-mediated stabilization of test conformations. Biological activities of the reduced (—SH) or oxidized (cystine cross-linked) peptide can then be measured and compared. The reduced peptide provides a control on possible perturbations introduced by replacement of the original amino acid residue by cysteine. If the predicted tertiary structure is correct, the disulfide cross-linked peptide should have an efficacy equal to, or greater than, the original peptide. The possibility of greater efficacy arises because the disulfide link restricts the number of possible conformations of the peptide, thus increasing the effective concentration of the biologically active conformer.

The quantifiable antimicrobial activities of peptides have been determined as described above. Through molecular modeling, qualitative correlation among structure and activity can be identified. However, it is also important to ascertain quantitative structure-activity relationships (QSAR) with robust predictive ability in designed peptides. Comparative Molecular Field Analysis (CoMFA) is a particularly useful tool in this regard. For example, CoMFA techniques have been applied to model and design novel HIV protease inhibitors, antibacterial agents, antidepressants, ACE inhibitors, and several other molecules now recognized as important therapeutic agents. Highly flexible molecules have also been successfully analyzed by CoMFA. Furthermore, data from these analyses can be integrated with other physical data (e.g., octanol/water partitioning to measure hydrophobicity and solvation energy), to augment predictive power.

Initially, two structure-activity analyses can be performed integrating all measures of antimicrobial activity, Holographic-QSAR (HQSAR) analyses can be used, since this method does not require conformational information. Therefore, rational mosaic peptide design can also be achieved, based on quantitative correlations of peptide primary structure and antimicrobial activity, as soon as the data set of biological properties becomes large enough to rise above background.

As is illustrated in the drawings, the invention is accordingly embodied in novel, improved antimicrobial peptides designed from unique templates to act to inhibit or kill microorganisms that are otherwise resistant to existing antibiotics. Two principal peptides, designated RP-1, Sequence No. 3, and RP-13, Sequence No. 14, were designed based in part upon microbicidal domains from platelet microbial proteins 1 and 2 (PMP-1, Sequence No. 2, and PMP-2, Sequence No. 1) as discussed in Yeaman, M. R., et al., "Purification and in vitro activities of rabbit platelet microbicidal proteins," Infect. Immun. 65:1023-1031, 1997. In turn, these or other microbicidal peptides can also be used as structural templates from which iterative peptides can be modeled and synthesized. These peptides, and derived analogues, may eventually be developed as therapeutic agents to significantly improve treatment of life threatening infections in humans due to organisms resistant to conventional antibiotics.

In addition to parameters known to be associated with antimicrobial activity, specific features have been identified which appear to be integral to maximal peptide microbicidal activity. These include: 1) conformation; 2) charge density and periodicity; 3) amphiphilic density and periodicity; 4) hydrophobic moment (MH); 5) mass-to-charge ratio; and 6) terminal orientation.

The present invention applies a model which predicts relative antimicrobial activity for a given amino acid sequence. This model takes into account the following published equation for determination of the mean hydrophobic moment ($M_H$):

$$M_H = \frac{\left[\left[\sum_{n=1}^{N} H_n \sin(\delta n)^2 + H_n \cos(\delta n)^2\right]\right]^{1/2}}{N}$$

where N is the number of residues, $H_n$ is the hydrophobicity of the nth residue, $\delta$ is the repeat angle, 100°, and $M_H$ is the mean hydrophobic moment. We have modified this equation to integrate $\alpha$ and $\beta$ parameters, where $\alpha$ is the alpha helicity index (helical fraction), $\beta$ is the beta-sheet index (sheet fraction). Use of the variables $\alpha$ and $\beta$ are described below.

Many cationic microbicidal peptides are known to exhibit amphiphilic α-helical or β-sheet conformation. It is also known that many antimicrobial peptides possess domains rich in hydrophobic amino acids. The mean hydrophobic moment $M_H$ dually assesses these parameters; $M_H$ is essentially the amphiphilicity of a peptide in an α-helica conformation. In previous models, $M_H$ and amphiphilicity are among the most predictive parameters of actual antimicrobial activity. The inventors have additionally recognized that potent microbicidal peptides contain distinct hydrophobic, amphiphilic and hydrophobic domains. The above model has been refined to integrate $M_H$ and α-helical or β-sheet conformations in the context of such domains. In this model, peptide microbicidal activity (predicted MIC, also $P_{MIC}$) is inversely related to $M_H$ and α-helicity such that: $P_{MIC}=1/\alpha=[(M_H)\cdot(\alpha_{peptide})]$ where α is equal to the sum of the α helical fractions of the peptide. Similarly, β-sheet peptides will be assessed for $P_{MIC}$ as follows: $P_{MIC}=1/\alpha[(M_H)\cdot(\beta_{peptide})]$, where $\beta_{peptide}$ is equal to the sum of the β sheet fractions of the peptide. $P_{MIC}$ can be inferred from the respective outcome of these models as they apply to a helical, β-sheet, or other peptide conformations. In either case, the lower the $P_{MIC}$, the greater the predicted microbicidal activity. This model has proven successful in guiding selection of templates used in designing templates RP-1, Sequence No. 3, and RP-13, Sequence No. 14, and derived metapeptides, discussed further below.

Figure 2B:
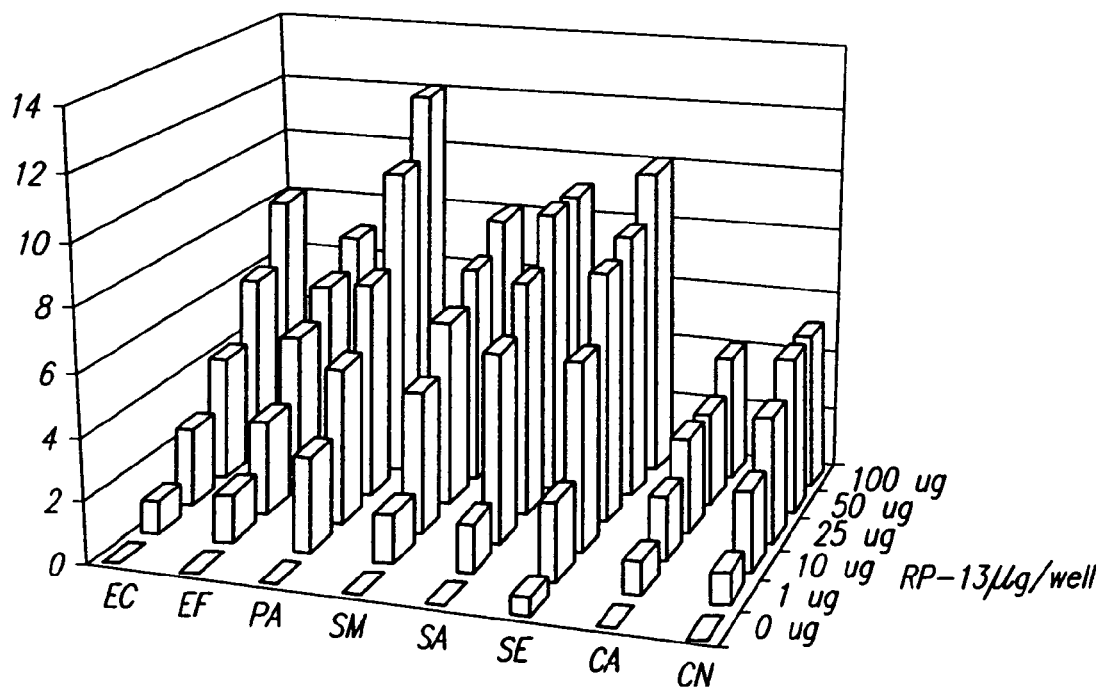
FIG. 2B is a three-dimensional graph of the antimicrobial spectra of RP-13, Sequence No. 14, in vitro (radial diffusion assay)

The peptide model has been used according to the principles of the invention to design RP-1, Sequence No. 3, and RP-13, Sequence No. 14, template peptides from microbicidal domains of PMPs 1 and 2, as illustrated in FIG. 1. These peptides exert rapid (less than 2 hours) and potent (nanomolar concentration) microbicidal activities against a spectrum of pathogens in vitro, many of which are resistant to conventional antibiotics, as is shown in FIGS. 2a and 2b, reflecting in three-dimensional graphs the antimicrobial spectra of RP-1, Sequence No. 3, and RP-13, Sequence No. 14, in vitro (radial diffusion assay). Inocula were $1\times10^6$ CFU/ml, and incubation conditions were pH 7.2 (RP-1, Sequence No. 3) or pH 5.5 (RP-13, Sequence No. 14), for 24 hours at 37° C. (Key: EC, *E. coli*; EF, *Ent. faecalis*; PA, *Ps. aeruginosa*; SM, *St. mutans*; SA, *S. aureus* (MRSA); SE, *S, epidermidis* (MRSE); CA, *C. albicans*; CN, *Crypto, neoformans*) Moreover, these templates differ in secondary structure (α-helix vs. β-sheet, respectively) as determined by FTIR spectroscopy and molecular modeling, and have differential pH optima for microbicidal activity (pH 7.2 vs. 5.5, respectively). Thus, the use of peptides derived from PMPs 1 or 2, RP-1 or RP-13, or other templates will provide complementary opportunities to examine the relationship among peptide structure, microbicidal activity, pathogen specificity, mechanism of action, conditions for activity, and mammalian cell toxicity. These data will be incorporated into subsequent iterations of peptide design.

With reference to FIGS. 2A. and 2B, designs for novel microbicidal metapeptides should maximize peptide parameters believed to be integral to microbicidal activity, as discussed above. Specific design strategies can include charge substitution, non-polar substitution, aromatic substitution, peptide extension or truncation, and use of D-enantiomers, retromer, retroenantiomer, N-∈monomethyl-lysine, or other amino acids not normally found in native peptides, or any combination of these approaches. In addition, conformer restriction and/or disulfide bridge conformer stabilization can be used to create designs with specific conformational parameters found to be relevant to derived antimicrobial properties.

In charge substitution, charged amino acids can be substituted with alternate amino acids such that the overall charge is essentially conserved. Examples of interchangeable residues where charge conservation substitution can be used to create novel peptides are lysine and arginine, or aspartic acid and glutamic acid.

Peptides can also be designed with substituted non-polar residues to study this effect on peptide microbicidal activity. Leucine and isoleucine are common examples of hydrophobic amino acids in antimicrobial peptides. Such residues have a significant impact on hydrophobic density and mean hydrophobic moment ($M_H$) as they relate to peptide microbicidal activity.

Peptides with enhanced microbicidal activity and reduced mammalian cell toxicity can also be generated with aromatic substitutions. Aromatic amino acids such as tyrosine, phenylalanine, and tryptophan are believed to influence mean hydrophobic moment as well as hydrophobic density.

Peptide extension or truncation can also be used to model peptide designs with strategic modifications. Peptides of reduced chain length generally exhibit features which may be advantageous as potential therapeutic agents as compared with larger proteins: 1) smaller peptides typically have greater distribution via more efficient diffusion; 2) they are generally less immunogenic than larger peptides; and 3) shorter peptides tend to be less susceptible to proteolytic degradation than comparable larger peptides. Selected peptides which exhibit potent microbicidal activity can also be synthesized as N-∈monomethyl-lysine and/or D-amino acid analogues. These strategies can be useful to increase specificity, reduce toxicity, and extend half-life of these peptides.

Peptides derived from RP-1, Sequence No. 3, and RP-13, Sequence No. 14, or other natural or novel templates will be suitable in mass to model by energy based methods. This approach can be used to identify stable conformers, and thus the most likely to retain structures believed to confer microbicidal function. Phi (φ) and psi (ψ) angles can be assigned systematically; those incompatible with Ramachandran indices for particular amino acids can be rejected to speed the search process. Conformer side chains can be rotated to relieve unstable steric configurations, and promising conformers can be partially minimized using AMBER force-field strategies. Lowest energy conformers can be further analyzed by molecular dynamics to determine stability. The Brookhaven data base can also be searched for peptides homologous to these peptides, which can be used as comparative templates. Side chain contacts can be relieved and minimized by molecular mechanics, and lowest energy conformations analyzed by molecular dynamics. Data from these manipulations can be used to remodel first generation peptides, such as RP-1, Sequence No. 3, RP-13, Sequence No. 14, or other template peptides to further enhance their antimicrobial properties, and reduce their toxicity.

Conformation of peptides can also be significantly influenced by solvation. Promising peptides identified can be solvated in TIP3 water. Solvent effects on molecular dynamic trajectories can be analyzed, and free energy perturbations used to assess solvent energies. Selected solvents can be seeded with counter ions at various concentrations to investigate possible conformational changes in peptides induced by ionic interactions. Furthermore, antimicrobial peptides likely interact with lipid bilayers. At the junction between the aqueous phase and the lipid bilayer, lipid polar head groups create a unique environment; this environment can produce alterations in peptide conformation. Lipid environments (bilayers) simulating bacterial or fungal cytoplasmic membranes (e.g. phosphotidyl glycerol or ergesterol) can be tested for interaction with peptides. Two dimensional arrays of polar head groups will be made and immobilized. A uniform solvation field will be used on either side to simulate the aqueous and hydrocarbon environments. This will permit examination of the effect of charge array on peptide conformation in relationship to lipid interaction. The environment of the lipid bilayer can then be simulated by minimizing the dielectric constant, and removing distance-dependent terms in dielectric function. Analysis of molecular dynamics can also be conducted to examine influence of lipid environments on peptide trajectory.

Comparative molecular field analysis (CoMFA) seeks predictions of biological activity from amino acid sequences. CoMFA can be conducted in two ways. First, all peptides can be equilibrated in a common extended conformation, and their side chains relaxed. A conventional CoMFA can then be constructed. This approach takes advantage of the fact that CoMFA does not appeal to any one mechanism of action, and seeks correlations between changes in structure and changes in biological activity. Induced folding should be implicit in the CoMFA analysis. In a second method, each peptide can be modeled in the lowest energy conformer, and conformers can be used to construct potential fields to be analyzed by CoMFA.

Novel antimicrobial peptides suitable for use within the present invention can be synthesized directly, or, developed using combinatorial chemistry libraries (Silen, J, L, A. T. Lu, D. W. Solas, et al., *Antimicrob. Agents and Chemother* 42:1447-1453 (1998)). Briefly, combinatorial libraries can be made by using split-and-pool synthesis, as described by Furka et al. (Furka, A., F. Sebestyen, M, Asgedom, et al., *J. Pept. Protein Res.* 37:487-93 (1991)). For example, beads are distributed into three reaction vessels, and an amino acid (A, B, or C) is coupled to the beads. The beads are pooled and redistributed to the same three reaction vessels, where the another amino acid is coupled, resulting in a dipeptide. This creates a set of 2×3 peptides: AA, AB, AC, etc. The process is repeated once more for example, to create a set of 27 tripeptides. A fundamental consequence of this approach is that there can be millions of beads used in the synthesis, with each bead carrying one unique compound that must be screened and identified.

Several approaches can be used to identify the structure of the compound carried on an individual bead. The compounds are tethered to the beads via UV photo-labile linkers to allow release of the compound for assay (Holmes, C. P., and D. G. Jones, *J. Org. Chem.* 60:2318-2319 (1995)). Chemical identifier tags that can be detected more efficiently than the library compound that they represent, are added to the beads after each synthetic step. Thus each bead carries a record of the synthesis of the compound also carried on that bead. By "reading" this tag, one can deduce the identity of the compound carried on the bead. Numerous lags and analytical methods for reading these tags have been developed (Kerr, J. M., S. C. Banville, and R. N. Zuckermann, *J. Am, Chem. Soc.* 115:2529-2531 (1993); Krchnak, V., A. S. Weichsel, D. Cabel, et al., *Pept. Res.* 8:198-205 (1995); Needels, M. C., D. G. Jones, E. H. Tate, G. L. et al., *Proc. Natl. Acad. Sci. USA* (1993)).

Jayawickreme et al. (Jayawickreme, C. K., G. F. Graminski, J. M. Quillan, et al., *Proc. Natl. Acad. Sci. USA* 91:1614-1618 (1994)) presented the first evidence that single-bead activity from antimicrobial peptides could be detected on acid-cleavable beads in a bacterial cell lawn format assay. For sensitive screening the library of beads can be manually spread on 105-µm-pore-size polyester mesh (Spectrum) that is subsequently placed on a nitrocellulose membrane (Bio-Rad) resting on 0.4% PBS agarose. Following 30 min of photolysis, the mesh is covered with a layer 0.4% LB agarose containing ~$10^7$ CFU of *B. subtilis* and incubated overnight. Compounds with antimicrobial activity are identified by zones of inhibited growth. Beads located in the center of the zones are selected for decoding, by manually isolating them from the assay plates. The encoded peptide is re-synthesized and antimicrobial activity is confirmed by testing in a standard broth microdilution assay against *B. subtilis* or other target microorganism of interest. Antimicrobial peptides desirably have minimum inhibitory concentrations against target microorganisms of <32 µg/ml.

Promising metapeptides and their iterations designed from microbicidal templates such as those described (e.g., RP-1, Sequence No. 3, and RP-13, Sequence No. 14) above can be synthesized by solid-phase Fmoc (9-fluorenyl-methyloxy-carbonyl) chemistry. The method is established, and has been extensively used in production of antimicrobial peptides. Preliminary amino acid analysis can be performed on samples of material to estimate overall coupling efficiency and to confirm peptide composition. Peptides can be cleaved and deprotected, and purified by gel filtration (BioGel P-10) and reverse phase-HPLC (RP-HPLC). This latter instrument can be equipped with a variety of columns including C-4, C-8, and C-18 silica-based reversed phases (Vydac), and synthetic phases such as PRP-300 (Hamilton) used to purify crude peptides on a preparative scale. Following purification, peptides can be quantitated by amino acid analysis utilizing the Pico Tag system. Molecular mass of each peptide can then be confirmed by fast atom bombardment or electrospray mass spectrometry. Fourier-Transform infrared spectroscopy (FTIR) and molecular modeling can then be used to verify the predicted secondary structure of synthetic peptides. In some cases, conformational studies can be performed using analytical ultra-centrifugation using established Stokes radius (radius of gyration) predictions to detect possible peptide-peptide interactions. This approach to peptide production and structural confirmation is highly efficient: a peptide can be synthesized, purified, and verified for sequence and conformation over a ten-day period.

Peptides are tested for antimicrobial potency and spectra against a panel of bacterial and fungal pathogens representing multiple antibiotic-resistance. This panel will include both clinical isolates as well as genetically-defined laboratory strains which exhibit MIC values considered resistant to respective antibiotics. Comparative control organisms to those assembled are summarized in Table 1 below.

TABLE 1

Antibiotic Resistance Phenotype

| Organism | Control Strain | Bla | Van | Amg | Amb | Flu |
|---|---|---|---|---|---|---|
| Staphylococus Aureus | ATCC 27217 | R | S | R | N/A | N/A |
| Streptococcus pneumonia | ATCC 35088 | R | S | R | N/A | N/A |
| Enterococcus Faecalis | ATCC 47707 | R | R | R | N/A | N/A |
| Escherichia coli | ATCC 43827 | R | S | R | N/A | N/A |
| Pseudomonas aeruginosa | ATCC 17468 | R | R | R | N/A | N/A |
| Candida Albicans | ATCC 36082 | N/A | N/A | N/A | S | S |
| Candida Krusei | ATCC 32672 | N/A | N/A | N/A | S | R |
| Candida Lusitaniae | ATCC 42720 | N/A | N/A | N/A | R | R |

(Key: R, resistant;
S, sensitive;
Bla, β-lactams;
Van vancomycin;
Amg, aminoglycoside;
Amb, amphotericin B;
Flu, fluconazole.)

A central goal is to correlate peptide structure with function to identify peptides with potent activity and reduced toxicity. Criteria for success are two- to ten-fold increases in potency as compared with templates RP-1, Sequence No. 3, or RP-13, Sequence No. 14. In this regard, it is advantageous to assess the microbiostatic and the microbicidal activities of peptides, and to correlate these activities with mammalian cell toxicity. For all assays, organisms are cultured to logarithmic-phase per NCCLS guidelines.

We have used the agar radial diffusion assay to determine antimicrobial activities of proteins against microbial pathogens in vitro. One million colony forming units are mixed into 10 ml (i.e., $1 \times 10^5$ CFU/ml) of melted 1% agarose (in 10 mM $NaHPO_4$ and cooled to 42° C.) containing minimal nutrient and adjusted to either pH 5.5 or pH 7.2. The agar is solidified in culture dishes, and sample wells are formed. Peptides at various concentrations are dissolved in 10 µl of 0.01% acetic acid buffer (pH 5.5 or 7.2), loaded into individual wells, and incubated at 37° C. for three hours. The plate is then overlayed with 1% agarose containing nutrients and incubated (37° C., for at least 24 hours). Peptides purified by RP-HPLC lacking antimicrobial activity are tested in parallel as controls. Zones of inhibition are measured to quantify antimicrobial activity. This assay will not distinguish between microbicidal and microbiostatic actions, but is highly sensitive to peptides with one or both functions.

Minimum inhibitory (MIC) and microbicidal concentration (MMC) assays can also be performed, and may include a microvolume assay which is used to quantitatively screen peptides for antimicrobial activities. In this assay, suspensions of bacteria or fungi in appropriate media are placed in 100-200 µl final volumes in microtiter plates. Standard (uncoated), poly-L-lysine coated, or otherwise positively charged plates may be used for these assays, since cationic peptides may bind to strongly anionic surfaces. Purified peptides are then serially diluted, descending from 100 µl/ml. Organisms are inoculated into wells to a concentration of $1 \times 10^5$ CFU/ml, and plates incubated (37° C., for at least 24 hours). Well turbidities are then assessed visually and by spectrophotometry to quantify growth inhibition versus wells containing no peptide. MMCs are then determined by quantitative culture of MIC wells exhibiting no visible growth.

Microbicidal kinetics of purified peptides are assessed by resuspending the peptides in 0.01% acetic acid buffer (pH 5.5 or 7.2), and organisms are resuspended to a concentration of $1 \times 10^5$ CFU/ml in 50-250 µl of sterile buffer containing peptide concentrations from 0 to 40 µl/ml. Controls contain buffer alone or non-antimicrobial proteins and organism as above. Mixtures are incubated at 37° C. for up to 48 hours, after which aliquots are quantitatively cultured and incubated for 24 to 48 hours. Killing is expressed as decrease in $logarithm_{10}$ surviving CFU/ml. The limit of sensitivity in microbicidal assays is considered to be a 1 log reduction in viable cells.

Flow cytometry can also be used to examine kinetics and mechanisms of the action of the peptides on bacterial membrane integrity and energetics. Peptides which differ in activity or specificity for their ability to depolarize and/or permeabilize microbial membranes can also be compared by analysis of membrane depolarization, and permeabilization. $DiOC_5$ is a charged lipophilic dye which partitions into the cytoplasm, and is dependent on intact $\Delta\psi$ for intracellular retention. Organisms prepared as above are labeled in darkness for 30 minutes at about 20° C. in PBS containing 0.05 µM $DiOC_5$. Organisms are resuspended to a concentration of $5 \times 10^8$ CFU/ml in $K^+$MEM containing an individual peptide, and incubated at 37° C. For flow cytometry, organisms are washed, sonicated, counted, and resuspended in $K^+$MEM buffer. Reductions in mean $DiOC_5$ fluorescence relative to controls are interpreted to represent loss of $DiOC_s$, indicating membrane depolarization. Positive control cells exposed to valinomycin, as well as control cells not exposed to any peptides, are analyzed for $DiOC_5$ fluorescence in parallel.

Propidium iodide is excluded from cells with normal membrane integrity, but enters cells permealized to molecules ≥2 nm in diameter, and can be stimulated to emit fluorescence at >620 nm. Organisms prepared as above are resuspended to a concentration of $5 \times 10^8$ CFU/ml in $K^+$ MEM containing a selected peptide, and incubated for pre-selected times (ranging from zero up to about 120 minutes) at 37° C. Cells are washed in fresh $K^+$MEM, sonicated, counted, and resuspended in KIMEM buffer containing 20 µM propidium iodide. Control cells exposed to ethanol (positive control for permeabilization) are assessed for propidium iodide uptake in parallel. Increases in mean propidium iodide fluorescence relative to control cells are interpreted to indicate increases in permeability.

Erythrocyte permeabilizing and hemolytic activities of peptides exhibiting potent microbicidal activity are also studied as indicators of potential in vivo toxicity. Four-percent (vol/vol) of washed human erythrocytes (in PBS alone, or in PBS plus 10% heat-inactivated PNHS are incubated with selected peptides ranging in concentration up to 100 times greater than geometric mean MICs. After 24 hours of incubation at 37° C., erythrocyte permeabilization and hemolysis are determined spectrophotometrically. Permeabilization and hemolysis will be compared to buffers alone, and with a triton X-100 control (100% hemolysis).

Endothelial cell injury due to peptides is measured using a standard chromium ($^{51}Cr$) release assay, described in Filler, S. G., et al., "*Candida* stimulates endothelial cell eicosanoid production" J Infect Dis. 1991, 164:928-935; Filler, S. G., et al., "Mechanisms by which *Candida albicans* stimulates endothelial cell prostaglandin synthesis" Infect Immun. 1994, 62:1064-1069; Filler, S. G., et al., "Penetration and damage of endothelial cells by *Candida albicans*" Infect Immun. 1995, 63:976-983. Briefly, endothelial cells in 96 well tissue culture plates are incubated with Na$^{51}$CrO$_4$ overnight. The following day, the unincorporated isotope tracer is removed by rinsing, and peptides in 0.01% acetic acid buffer are added to the endothelial cells. Control wells are exposed to buffer alone. After a predetermined incubation period, the medium is aspirated and the amount of $^{51}$Cr released into the medium is measured by scintillation. This approach facilitates toxicity screening of multiple peptides simultaneously, and minimizes the amount of peptide necessary for assessment.

Each antimicrobial and toxicity assay described above is performed independently a minimum of two times, and means±standard error is calculated for each peptide under varying exposure conditions (concentration or pH) as compared with control samples. Statistical analyses of microbicidal data are performed using Student t test or Kruskall-Wallis rank sum analysis for non-parametric data, and corrected for multiple comparisons as appropriate.

Leukocyte Potentiating Antimicrobial Peptides

PMP-2 structural determinants also have effects on neutrophil antimicrobial functions. The antimicrobial roles of neutrophils are critically linked to their capacity to respond to stimuli generated at sites of infection, undergo directed migration toward these sites, and execute antimicrobial functions once there. Chemokines exhibiting the cystine-variable-cystine motif (C-X-C) are potent stimulants of these responses. Peptides that selectively amplify this activity are not only integral to antimicrobial host defense, but they are also reasonable targets for study as novel anti-infective agents. PMP-2 exhibits an N-terminal C-X-C motif. Furthermore, our preliminary structural data indicate that PMP-2 is an analogue of PF-4, a C-X-C chemokine known to amplify neutrophil chemotaxis and oxidative burst. Moreover, our preliminary studies suggest that PMP-2 amplifies in vitro neutrophil phagocytosis and intracellular killing of S. aureus. Additionally, PMP-2 exerts significantly greater microbicidal activity under conditions of pH consistent with those known to exist in the neutrophil acidic phagolysosome (e.g., pH 5.5). Based on these rationale, we hypothesize that PMP-2 has structural determinants that potentiate neutrophil functions crucial to antimicrobial host defense.

Alpha-chemokines such as PF-4 and IL-8 are critical in amplifying the host inflammatory responses to infection. For instance, the concentration of macrophage-derived IL-8 is directly correlated with neutrophil number in human pleural effusions. Furthermore, inhibition of IL-8 by monoclonal Abs prevents neutrophil influx in lipopolysaccharide-induced pleuritis in rabbit models. These C-X-C chemokines also potentiate the microbicidal function of neutrophils. Nibbering et. al. have noted that IL-8 potentiates non-oxidative intracellular killing of *Mycobacterium fortuitum* by human granulocytes. Additionally, IL-8 enhances in vitro neutrophil microbicidal activity against *Candida albicans*. Petersen et, al. have recently shown human PF-4 acts along with other chemokines to potentiate neutrophil antimicrobial response. We have determined that rabbit PMP-2 possesses a C-X-C motif homologous to that found in α-chemokines We have also determined that at least two microbicidal peptides from human platelets, hPF-4 and hCTAP-III, also contain this motif hPF-4 is chemotactic for neutrophils, and enhances neutrophil phagocytosis of microorganisms in vitro. An additional mechanism through which PMP-2 may augment neutrophil microbicidal function lies in its enhanced microbicidal activities acidic pH, such as exist in the neutrophil phagolysosome. Thus, PMP-2 on the microorganism surface may have greater microbicidal activity once ingested by the neutrophil. Results from our preliminary. studies are consistent with this discovery. From these perspectives, PMP-2 likely potentiates critical antimicrobial functions of neutrophils in addition to exerting direct antimicrobial activities.

PMP-2 contains a C-X-C motif, and exerts significantly greater microbicidal activity under conditions of pH that exist in the acidic phagolysosome of the neutrophil (e.g. pH 5.5). The dominant thrombin-induced PMP (tPMP-1) tacks the C-X-C motif, and exhibits diminished microbicidal activity at pH 5.5. Therefore, evaluation of PMP-2 domain influences on neutrophil function can permit assessment of the importance of both the C-X-C motif (±the E-L-R motif; discussed below) in the context of overall primary structure, as well as the relationship of pH and microbicidal activity in enhancing neutrophil antimicrobial functions. Of interest is the influence of PMP-2 domains on neutrophil antimicrobial function in vitro and the quantification of their effects on neutrophil chemotaxis, phagocytosis intracellular killing of microorganisms. PMP-2 domains found to amplify phagocytosis or intracellular killing by neutrophils can be assessed for their influence on oxidative burst in neutrophils. PMP-2 domain-mediated oxidative potentiation can be differentiated from non-oxidative neutrophil potentiation in this manner. Results from these studies can be used to guide subsequent experiments to define the specificity of PMP-2 determinants in augmenting neutrophil antimicrobial functions.

A central goal of the differentiation of the effects of PMP-2 structural determinants on neutrophil antimicrobial functions is the comparison of PMP-2 domains that influence neutrophil microbicidal action with those that confer direct antimicrobial functions. The fact that C-X-C chemokines potentiate neutrophil antimicrobial functions has been well established. Yet, how this occurs has been complicated by the recent discovery of two distinct C-X-C receptors, CXCRI and CXCR2, co-expressed on mammalian neutrophils. Each of these receptors is a 7-transmembrane domain protein functionally coupled to G protein activation. Although both receptors bind IL-8 avidly, they differ in selectivity for other C-X-C chemokines, such as PF-4. The principal difference in structure between IL-8 and PF-4 is a N-terminal glutamic acid-leucine-arginine (E-L-R) motif that immediately precedes the initial cystine residue in the C-X-C motif of IL-8. Interestingly, IL-8 is considered the only relevant ligand for CXCRI. Activation of neutrophils via the CXCRI receptor also requires presence of a basic amino acid determinant in the sixth position after the second C-X-C motif cysteine residue. IL-8 exhibits this determinant, but PF-4 does not. This fact has been suggested as a principal mediator of CXCRI specificity. Based on the fact that PMP-2 exhibits an N-terminal C-X-C motif homologous with that of IL-8, and that it is an analogue of rPF-4 known to induce neutrophil chemotactic response, we hypothesize that PMP-2 stimulates neutrophil chemotaxis. However, PMP-2 lacks the E-L-R and the basic sixth-position motifs (PMP-2 has leucine in residue position 21) linked to CXCRI specificity. Thus, we further hypothesize that PMP-2 stimulation of neutrophil chemotaxis specifically occurs through the CXCR2 receptor. Thus, synthetic domains of PMP-2 can be constructed that do or do not have the E-L-R and/or basic sixth residue motifs believed to interact specifically with the CXCRI receptor. This approach can define whether PMP-2 domains or other peptides influence neutrophil antimicrobial function via the CXCR1 or CXCR2 receptor. Rabbit and human neutrophil responses to PMP-2 structural domains ±E-L-R and/or basic residue motifs can be compared to define species specificity of these peptides. In addition to defining the specificity with which PMP-2 determinants influence crucial neutrophil antimicrobial functions, such in vitro studies can facilitate future investigations to define the role of PMPs in host defense in vivo. Since such in vivo studies cannot initially be performed in humans, PMP-2 can yield information applicable to these future studies using rabbit models of infection.

In investigation of the influence and specificity of PMP-2 domain peptides on neutrophil chemotaxis in vitro, rabbit neutrophils can be isolated from fresh whole blood and labeled with $^{51}$Cr. To conserve peptide, a micro-well assay can be used that is modified from those described by Boyden and Schroder. In these assays, $2.5 \times 10^6$ neutrophils are placed in the upper compartment of a chemotaxis microchamber (Neuroprobe), separated from a lower chamber by a membrane having a 3 μm pore size. Purified peptide (1-5 μg) in 2 mM acetate buffer is then placed in the lower compartments. Appropriate positive controls assessed in parallel can be N-f-met-leu-phe, IL-8, rabbit or human PF-4, or PMP-2 in the same buffer, or buffer alone. Chambers are then incubated for 1 hr at 37° C. in 5% $CO_2$. Upper chambers are removed, rinsed extensively, and counted by scintillation relative to respective controls: lower-compartment fluid; rinses of the upper or lower compartment; and a control for neutrophil specific activity. The number of neutrophils present in the upper and lower compartments can be interpreted in the context of these controls. Mean standard error of the mean (SEM) numbers of cells in each compartment can be determined and compared for each stimulus. Each condition is tested in triplicate, including both experimental and control peptides.

If a peptide increases migration of neutrophils, chemokinesis can be differentiated from chemotaxis using a modification of the checkerboard assay described by Cutler. For these studies, chemotactic gradients can be eliminated by placing purified peptide in the upper compartments along with neutrophils. These assays are performed under incubation conditions (<2 hr) to prevent peptide diffusion beyond specified compartments. This could cause neutrophils responding chemotacticajly to cease or reverse direction, artificially reducing peptide-mediated neutrophil chemotaxis. Neutrophil migration is assessed as above. A decrease in the magnitude of neutrophil migration is interpreted to indicate that the peptide is chemotactic for neutrophils. Alternatively, no change in mean neutrophil migration indicates that the peptide upregulates neutrophil chemokinesis.

Results from chemotaxis studies above can be used to guide subsequent experiments to define the specificity of PMP-2 determinants in neutrophil modulation, as outlined below:

1. PMP-2 domains stimulating neutrophil chemotactic response can be for tested for activity in the presence and absence of monoclonal Ab directed against the CXCR1 receptor, or CXCR2 receptor, or both Inhibition or reduction of PMP-2 domain stimulation of neutrophil chemotaxis under these conditions will define the specificity of this effect to the CXCR1 or CXCR2 receptors, or to a mechanism that is independent of these receptors (e.g. peptide activity in the presence of both monoclonal Abs). Additionally, analogues of selected, antimicrobial peptides can be synthesized with either the E-L-R or basic sixth residue motifs, or both. Resulting alterations of CXCR1 vs. CXCR2 peptide specificity in neutrophil chemotaxis provide further evidence for engineered selectivity of PMP-2 determinants for specific neutrophil chemotactic receptors.
2. Likewise, selected PMP-2 domains or other peptides that fail to prompt neutrophil chemotaxis can be synthesized as analogues that contain the E-L-R and/or basic sixth residue motifs. The conversion of an inactive peptide to one that stimulates neutrophil chemotaxis is interpreted as evidence that it lacks these specific structural motifs corresponding to its inherent selectivity in neutrophil stimulation.
3. The influence of peptides and/or their analogues described above on human neutrophils can be assessed. These studies will lend insights into the specificity of peptide determinants or analogues on human neutrophils that co-express the CXCR1 and CXCR2 receptors. Results from these studies can be used to guide future efforts to create novel therapeutics that exert selective modulatory effects on human neutrophils.

Additionally, peptide analogues can be achieved using a combinatorial method, and therefore highly efficient with regard to both time and expense. It is important to note that it is also possible that peptides will act via mechanisms not previously described. This possibility underscores a major advantage of the proposed approach, which is intentionally not biased to identify any single specificity. Thus, the proposed approaches may also reveal novel interactions between peptides and neutrophils.

Flow cytometric Analysis of neutrophil antimicrobial functions in vitro can be evaluated using contemporary flow cytometry techniques. Use of flow cytometry has the advantages of analyzing the characteristics of individual cells, as well as the interactions between a large number of neutrophils and microorganisms. This methodology facilitates the rapid differentiation of subpopulations of neutrophils that have distinct antimicrobial responses. In addition, flow cytometry provides high specificity and quantitative precision. Flow cytometric experiments can be performed using a FACScan (Becton Dickinson) device when a single laser stimulation is sufficient. When multiple excitation wavelengths are required, the dual laser FACStar IV (Becton Dickinson) can be used.

Influence of synthetic peptides on microorganism phagocytosis by neutrophils in vitro can be evaluated by multicolor flow cytometry. This can be done from two perspectives: i) effect of microorganism exposure to peptide on subsequent neutrophil phagocytosis; and ii) effect of peptide priming of neutrophils on subsequent microorganism phagocytosis. Target organisms in these studies are control strains, and neutrophils treated with cytochalasin D serve as phagocytosis-negative controls. Microbial cells are fluorescence-labeled by incubation in appropriate medium containing 20 μM bis-carboxyethyl-carboxyfluorescein pentaacetoxymethylester (BCECF-AM, Calbiochem). BCECF-AM diffuses into microorganisms, where it is cleaved by cytoplasmic esterases to yield the membrane-impermeable fluorescent marker bis-carboxyethyl-carboxyfluorescein (BCECF). BCECF is retained by viable organisms, thus serving as a microorganism-specific label. Alternatively, neutrophils can be labeled in RPMI medium containing 5 μg/ml phycoerythrin (PE)-conjugated monoclonal antibody My-7 (Coulter Instruments; 45 min, 20° C.). My-7 is directed against the neutrophil CD-13 surface antigen. Therefore, PE-labeled neutrophils are readily distinguishable from BCECF-labeled microorganisms. Neither BCECF nor My-7 labeling methods significantly alter microorganism or neutrophil physiology, respectively, as determined in previous studies. Labeled microorganisms are then washed and suspended in 2 mM acetate buffer (pH 5.5 or 7.2). Peptide is added to labeled microorganism suspensions to achieve the following conditions: i) final inocula of $10^6$ CFU/ml; and ii) final sub-lethal peptide concentrations ranging from 0.5 to 5 μg/ml. To conserve peptides, volumes are 500 μl. Incubation is initiated by the addition of peptide to the microbial inoculum, and continued at 37° C. At predetermined timepoints (0, 15, 30, 60, and 120 minutes), 100 µl aliquots are washed in RPMI to remove excess peptide Organisms are then assessed to ensure they have retained the BCECF label following peptide exposure.

For phagocytosis assays, labeled, peptide-exposed microorganisms are mixed with neutrophils in RPMI±10% pooled normal serum (PNRS) to achieve a neutrophil-to-target cell ratio of 1:100. Three samples of cells prepared as above are included in each phagocytosis assay: 1) labeled microorganisms in flow buffer alone (control for BCECF label specificity and intensity); 2) labeled neutrophils in flow buffer alone (control for My-7 label specificity and intensity); and 3) labeled microorganisms mixed with labeled neutrophils. Mixtures will be incubated for 0, 15, 30, 60, or 120 min at 37° C. with agitation. To differentiate microorganism binding from phagocytosis, mixtures are cooled on ice to prevent further phagocytosis, and texas red conjugated monoclonal antibody directed against respective organisms (e.g., anti-S. Aureus protein A; ImmunoSys) is added to samples containing neutrophil-organism mixtures. Therefore, fluorescein emission (520 nm) corresponds to phagocytized organisms, while texas red emission (620 nm) specifies extracellular organisms when stimulated at 460 and 580 nm, respectively. Furthermore, fluorescein and texas red emissions are distinguishable from that of phycoerythrin-labeled neutrophils (575 nm). Organisms which do not retain the BCECF label are gated out of data in all phagocytosis studies. We appropriately monitor forward and 90° light scatter to minimize the collection of artifactual data due to cell clumping. In parallel, 100 µl aliquots are removed and analyzed by flow cytometry to determine microorganism viability (see below). Additionally, phagocytic assays are performed microscopically to confirm flow cytometric data. These controls allow us to adjust for underestimates in phagocytosis that may occur via microorganism loss of BCECF due to killing that may occur at later time points.

As an alternative approach to differentiating ingested vs. neutrophil-bound organisms, the fluorescence of extracellular microorganisms labeled with BCECF can be quenched by crystal violet, while fluorescence of those within neutrophils is unchanged. Additionally, fluorochrome-quenching reagents (Molecular Probes) that will de-fluoresce extracellular organisms, or use of fluorochromes with differential emission spectra within the neutrophil acidic phagolysosome (e.g., SNARF; Molecular Probes) can also distinguish pathogen binding vs. phagocytosis.

In order to determine the influence of peptides on intracellular killing of microorganisms by neutrophils, coincident with phagocytosis assays above (0, 15, 30, 60, and 120 minutes), 100 µl aliquots from each phagocytic assay sample can be processed to quantify intracellular killing. Neutrophils are lysed in cold distilled water and sonication, and microorganism survival assessed by flow cytometry. As above, viable microorganisms retain the BCECF label, while killed organisms lose the fluorescent label. Thus, microorganisms released by neutrophil lysis can be gated into one of two populations based on fluorescence to quantify: i) viable, fluorescent cells, or ii) non-viable, non-fluorescent cells. Interpretation of results in the context of control neutrophil killing of organisms permits comparison of the influence of peptide exposure (either microorganism, or neutrophil, or both) on additivity vs. potentiation of intracellular killing within neutrophils. In parallel, aliquots from each sample will be diluted into sodium polyanethol sulfonate buffer to discontinue peptide-mediated killing, and quantitatively cultured to corroborate flow cytometry analyses of intracellular killing. Note that peptides, analogues thereof (see above), and PMP-2 are compared for relative influences on rabbit and human neutrophil intracellular killing of pathogens. Thus, specific determinants integral to or selective for potentiation of neutrophil intracellular killing can be identified for further characterization as outlined below.

If a peptides is found to potentiate neutrophil phagocytosis or intracellular killing of microorganisms, it can be determined whether oxidative burst is linked to this effect. The generation of reactive oxygen intermediates such as superoxide anion is considered essential to neutrophil microbicidal potency. Hydroethidine (HE; Molecular Probes) can be used to quantify the influence of peptide on generation of superoxide anion by neutrophils. Neutrophils accumulate HE in the cytoplasm; it is oxidized to ethidium bromide by superoxide anion. Thus, ethidium bromide excitation at 488 nm yields 590 nm emission correlating with superoxide anion production, and can be used as detailed below.

Neutrophils isolated as above can be labeled by incubation in RPMI containing 1 µM HE for 15 minutes at 37° C. Residual HE is washed away, and neutrophils are exposed to 1-5 µg of selected PMP-2 domains for predetermined times (0, 15, 30, 60, or 120 mins) at 37° C. in RPME±10% homologous pooled normal serum. The principal variables in these experiments are: i) peptides with different structures (e.g., ±C-X-C motif); ii) varying durations and concentrations of neutrophil exposure to peptides; and iii) neutrophil priming by peptide followed by exposure to microorganisms. For these experiments, peptides can be selected that enhance microorganism phagocytosis and/or intracellular killing by neutrophils identified above. Each experiment includes labeled neutrophils in buffer alone (to control for background superoxide anion levels) in comparison to neutrophils exposed to selected peptides, with or without organisms. Calibration curves based on flow cytometric data from known superoxide concentrations using xanthine oxidase assays are used to estimate the absolute superoxide anion levels within neutrophils. Additionally, selected peptide analogues above are used to ascertain the specificity with which they stimulate neutrophil oxidative burst.

Examples of Novel Antimicrobial Peptides that Act Directly on Pathogens to Exert Microbicidal or Tvhcrobiostatic Activity Three basic groups can be categorized based on a source and/or design approach:

A. Rational Peptides (RP)

B. Fragment Peptides (FX)

C. Consensus Peptides (CS)

These groups are described in the present application; they are not recognized categorizations. The majority of peptide sequences listed herein fall into one of these groups.

Examples of Novel Antimicrobial Peptides that Potentiate One or More Antimicrobial Acnvmes of Leukocytes These peptides are derived from domains found in PMPs or other molecules that are either known to or predicted to stimulate one or more of the inherent antimicrobial functions of leukocytes such as neutrophils, monocytes, macrophages, and/or lymphocytes. Example sequences in this category are:

PMP-2$_{1-22}$:
(SEQ ID NO: 96)
Ser Asp Asp Pro Lys Glu Ser Glu Gly Asp Leu

His Cys Val Cys Val Lys Thr Thr Ser Leu Val;

PMP-2$_{1-37}$:
(SEQ ID NO: 97)
Ser Asp Asp Pro Lys Glu Ser Glu Gly Asp Leu

His Cys Val Cys Val Lys Thr Thr Ser Leu Val

Arg Pro Arg His Ile Thr Asn Leu Glu Leu Ile

Lys Ala Gly Gly;
and

SEQUENCE No. 17
(e.g. RP-15).

Variants of the above sequences or those present in FIG. 12, which have the described modifications in their Glu-Leu-Arg (ELR) and/or sixth basic residue components may also be suitable. Examples include:

21-K-PMP-2$_{1-22}$:
(SEQ ID NO: 98)
Ser Asp Asp Pro Lys Glu Ser Gly Gly Asp Leu His Cys Val Cys Val

Lys Thr Thr Ser Lys Val;

ELR-PMP-2$_{1-22}$:
(SEQ ID NO: 99)
Ser Asp Pro Lys Glu Ser Glu Gly Glu Leu Arg Cys Val Cys Val

Lys Thr Thr Ser Leu Val;

21-K, ELR-PMP-2$_{1-22}$:
(SEQ ID NO: 100)
Ser Asp Asp Pro Lys Glu Ser Glu Gly Glu Leu Arg Cys Val Cys

Val Lys Thr Thr Ser Lys Val;

21-K, CC-PMP-2$_{1-22}$:
(SEQ ID NO: 101)
Ser Asp Asp Pro Lys Glu Ser Glu Gly Asp Leu His Cys Cys Val

Lys Thr Thr Ser Lys Val;

ELR, CC-PMP-2$_{1-22}$:
(SEQ ID NO: 102)
Ser Asp Asp Pro Lys Glu Ser Glu Gly Glu Leu Arg Cys Cys Val

Lys Thr Thr Ser Leu Val;
and

21-K, ELR, CC-PMP-2$_{1-22}$:
(SEQ ID NO: 103)
Ser Asp Asp Pro Lys Glu Ser Glu Gly Glu Leu Arg Cys Cys

Val Lys Thr Thr Ser Lys Val.

Figure 13:
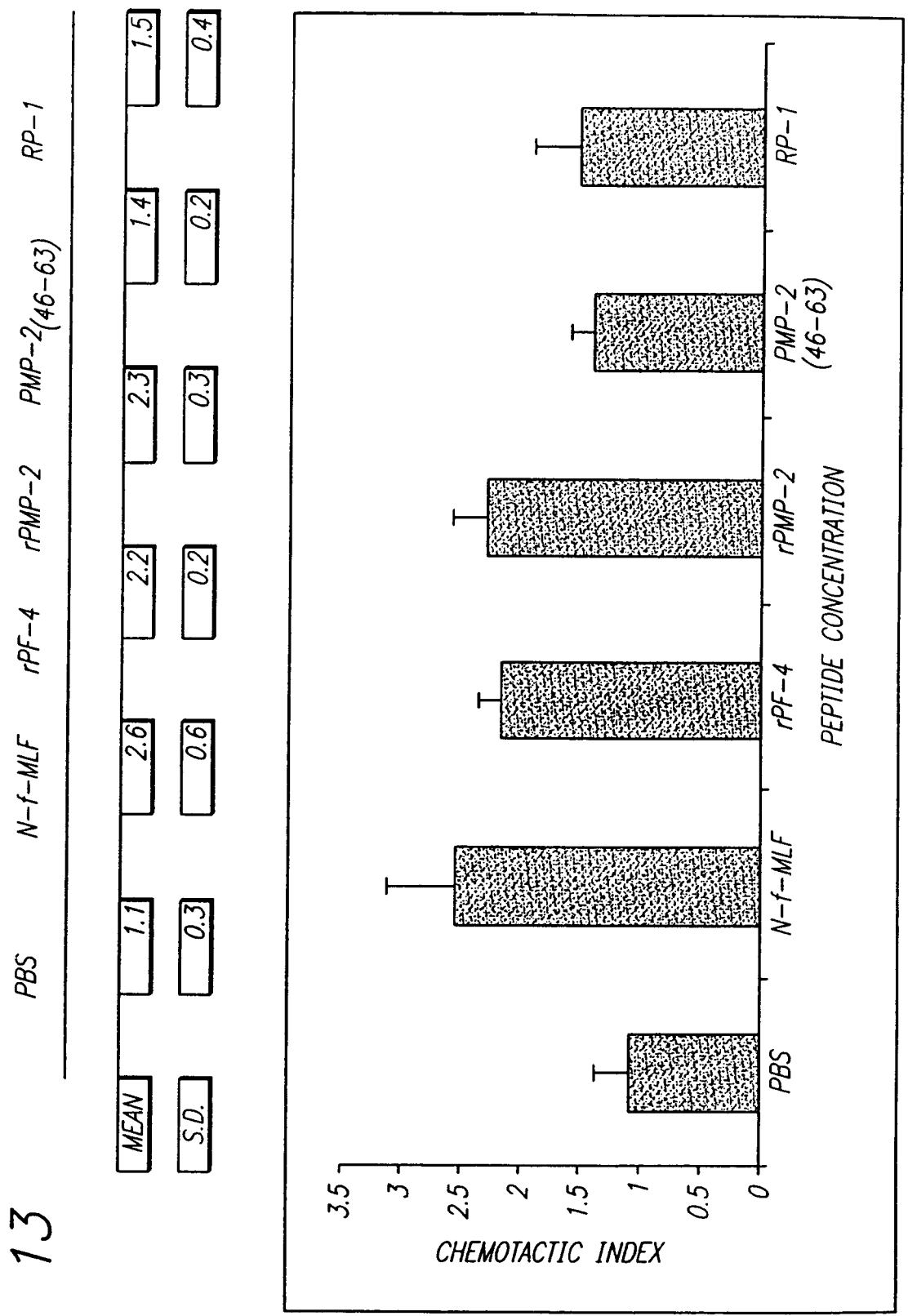
FIG. 13 is a chart of the chemotactic index for rabbit PMP-2 (rPMP-2), for various organisms.
Figure 14:
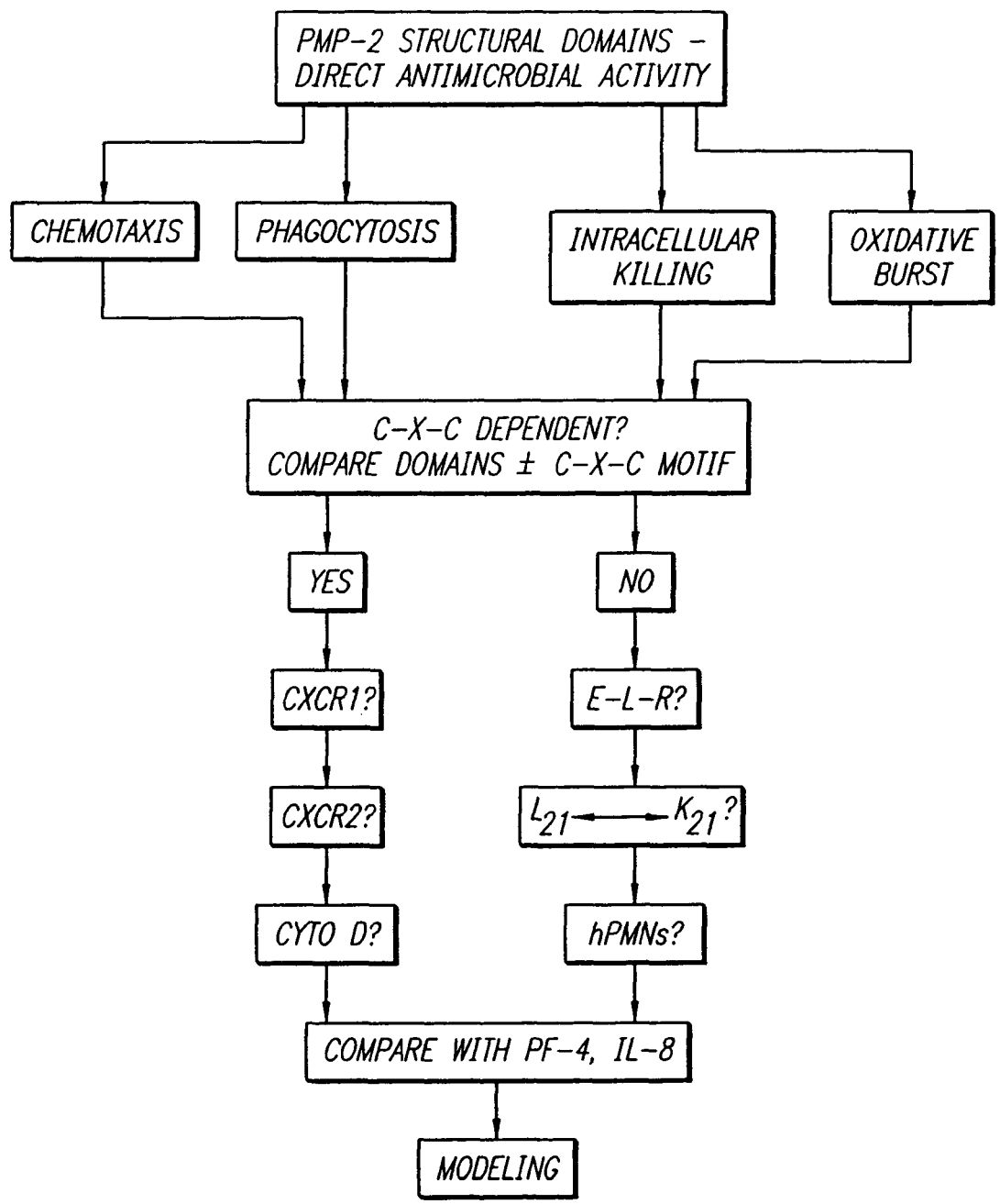
FIG. 14 is a flow chart for identifying and evaluating active antimicrobial domains for modeling of peptides according to the invention.
Figure 15:
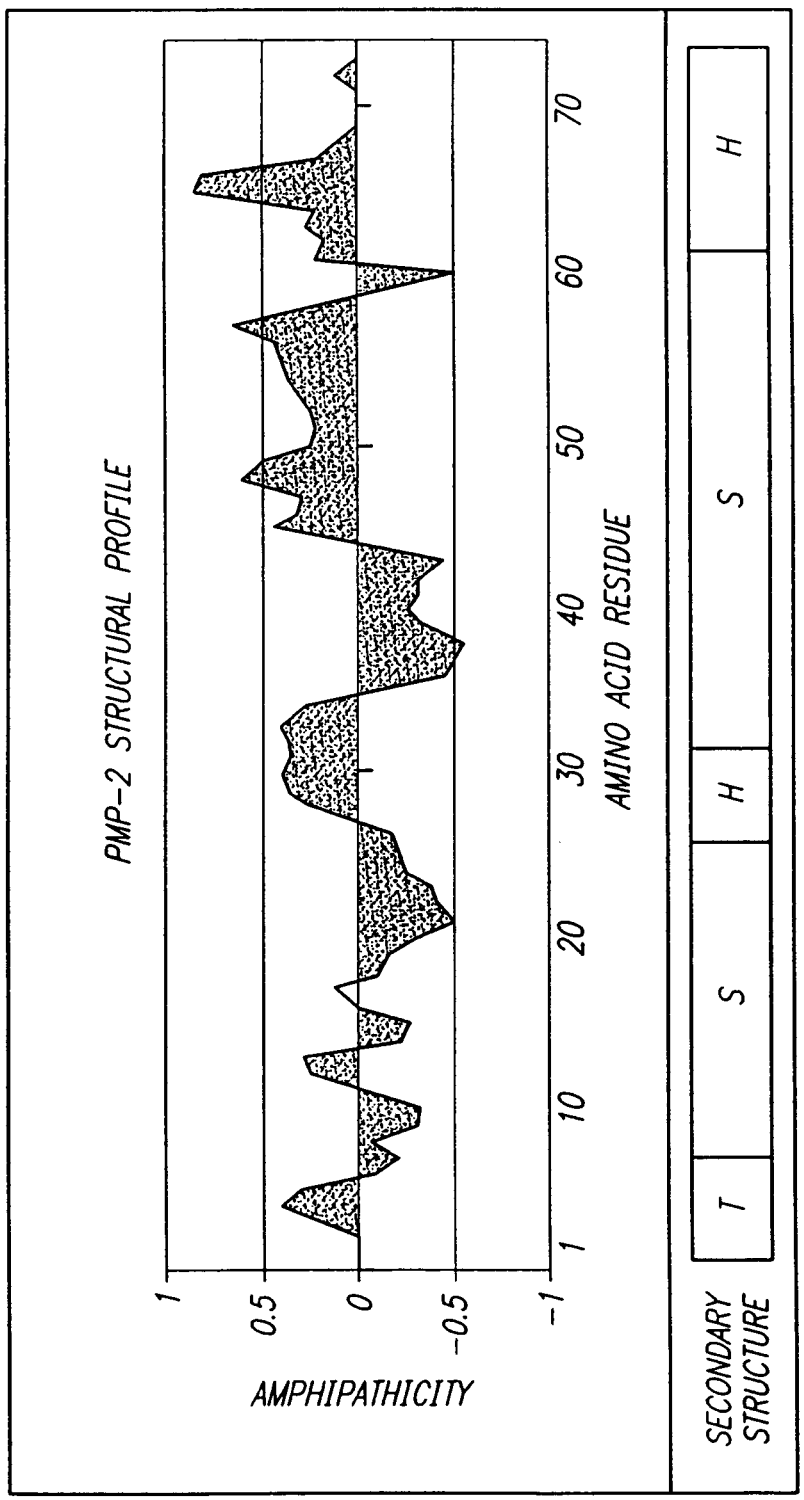
FIG. 15 is a chart of structural motifs in PMP-2, in which "S" indicates "sheet", "T" indicates "turn", and "H" indicates "helix"
Figure 16:
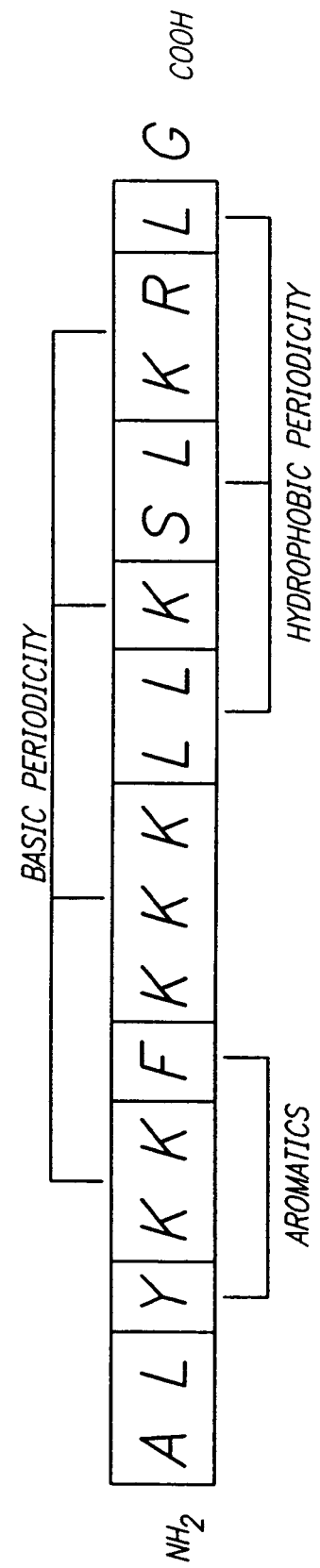
FIG. 16 is a diagram of the structure of RP-1.
Figure 17:
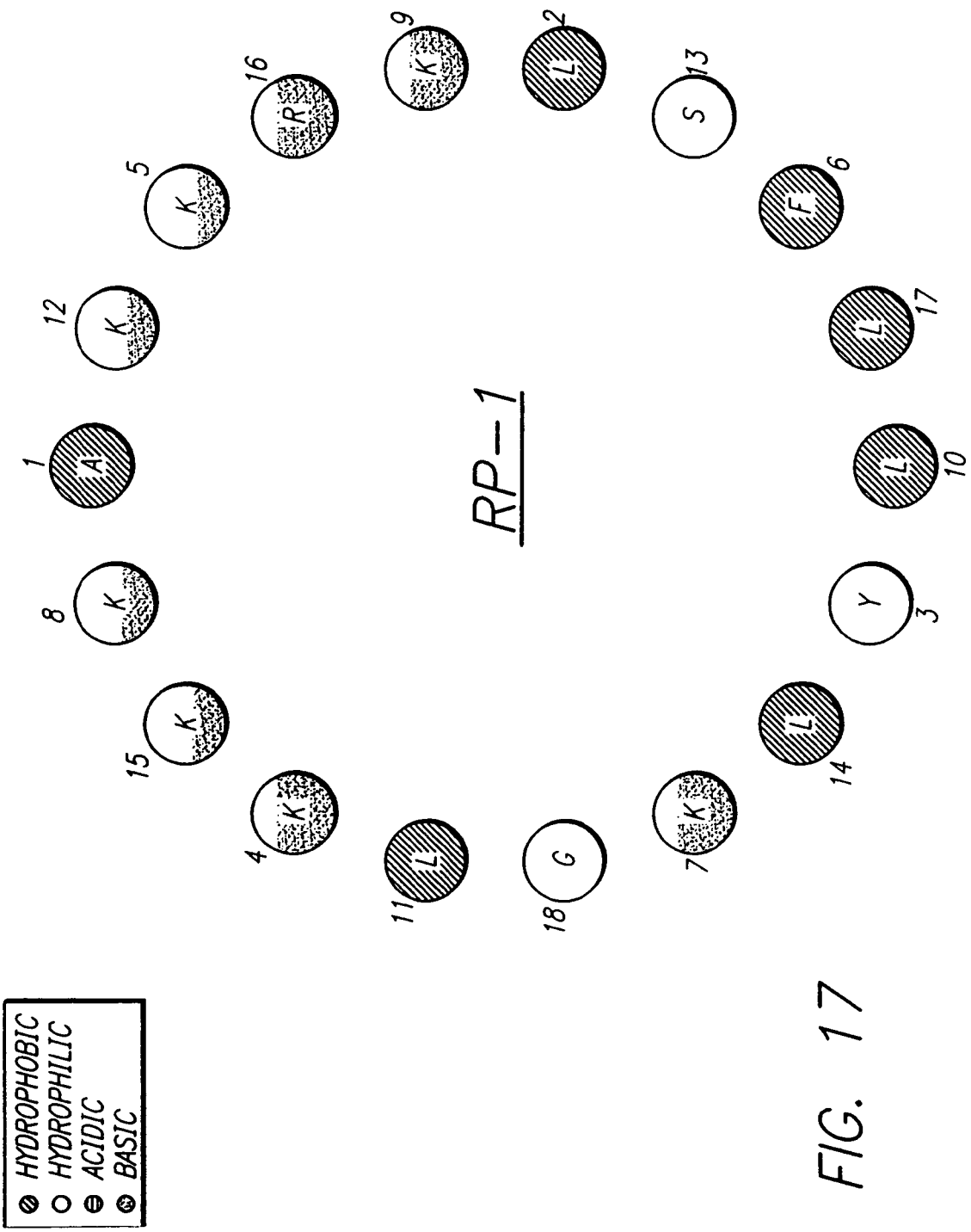
FIG. 17 is a helical wheel diagram of RP-1.
Figure 18:
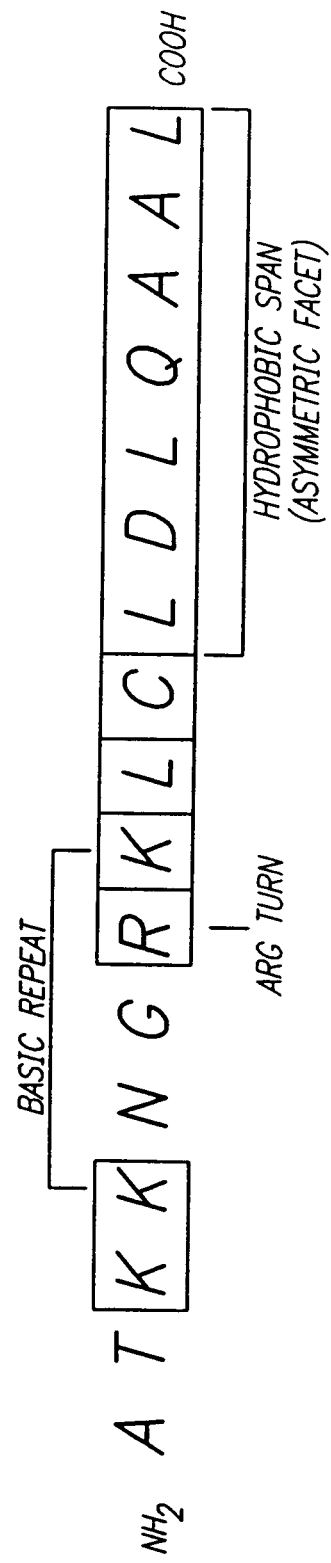
FIG. 18 is a diagram of the structure of RP-13.
Figure 19:
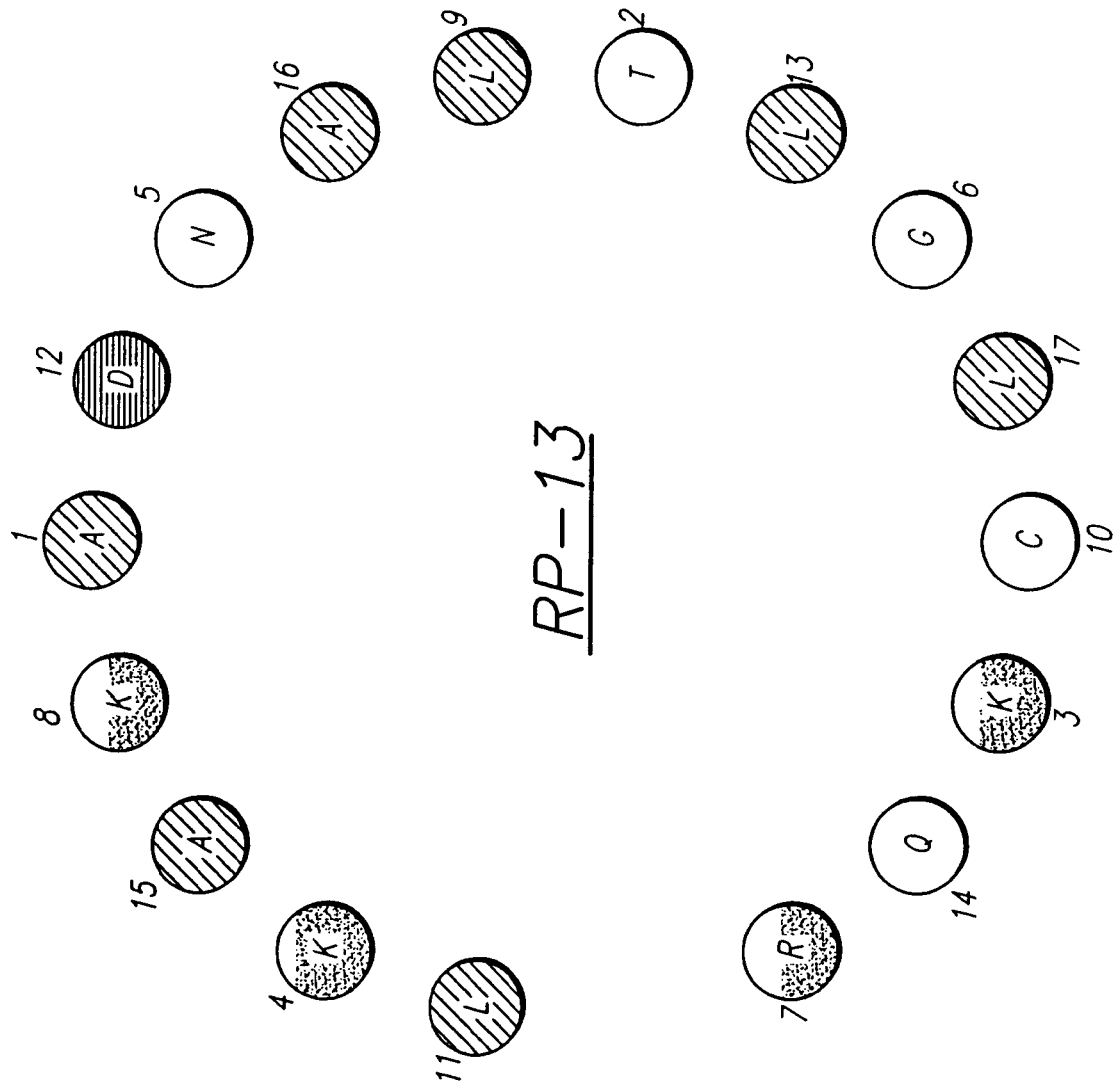
FIG. 19 is a helical wheel diagram of RP-13.

Further examples include any extension, truncation, substitution, retromerization, fusion, or conformer restriction of these peptides, related templates, or their iterations derived as discussed above. Note that the full-length PMP-2 is also included in this category by definition of its demonstrated inherent leukocyte potentiating properties as is illustrated in FIG. 13, showing the chemotactic index for rabbit PMP-2 [rPMP-2].

Examples of Novel Antimicrobial Peptide Mosaics that Combine the Above Activities These include logical and/or strategic mosaic constructs of the above peptides in the categories above. Conceptually, these mosaic peptides will consist of one or more domains exerting direct microbicidal and/or microbiostatic activity linked or otherwise combined with one or more domains exerting leukocyte potentiating activities. Examples (only a few of the logical constructs achievable from combining the above peptides) are listed below:

RP-1/PMP2$_{1-22}$:
(SEQ ID NO: 104)
Ala Leu Tyr Lys Lys Phe Lys Lys Lys Leu Leu

Lys Ser Leu Lys Arg Leu Gly Ser Asp Asp Pro

Lys Glu Ser Glu Gly Asp Leu His Cys Val Cys

Val Lys Thr Thr Ser Leu Val;

-continued

RP-11/PMP2$_{1-22}$:
(SEQ ID NO: 105)
Ala Leu Tyr Lys Arg Leu Phe Lys Lys Leu Lys

Lys Phe Ser Asp Asp Pro Lys Glu Ser Glu Gly

Asp Leu His Cys Val Cys Val Lys Thr Thr Ser

Leu Val;

-continued and

RP-1/21-K, ELR-PMP2₁₋₂₂:

(SEQ ID NO: 106)
Ala Leu Try Lys Lys Phe Lys Lys Lys Leu Leu

Lys Ser Leu Lys Arg Leu Gly Ser Asp Asp Pro

Lys Glu Ser Glu Gly <u>Glu</u> Leu <u>Arg</u> Cys Val Cys

Val Lys Thr Thr Ser <u>Lys</u> Val.

Other examples of mosaic constructs include any extension, truncation, substitution, retromerization, fusion, or conformer restriction of these peptides, related templates, or their iterations derived as outlined herein.

The antimicrobial peptides and derived metapeptides active alone or in combination with other agents against organisms such as bacteria and fungi can thus comprise peptides having amino acid sequences selected from the group consisting essentially of a first peptide template XZBZBXBXB and derivatives thereof selected from the group consisting of XZBBZBXBXB, BXZXB, BXZXZXB, XBBXZXBBX, and BBXZBBXZ, and a second peptide template XBBXX and derivatives thereof selected from the group consisting of XBBXBBX, XBBXXBBX, BXXBXXB, XBBZXX, XBBZXXBB, and XBBZXXBBXXZBBX. B can be, for example, at least one positively charged amino acid; X can be, for example, at least one non-polar, hydrophobic amino acid; and Z can be, for example, at least one aromatic amino acid. For example, B can be selected from the group of amino acids consisting of lysine, arginine, histidine, and combinations thereof; X can be selected from the group of amino acids consisting of leucine, isoleucine, alanine, valine, and combinations thereof and Z can be selected from the group of amino acids consisting of phenylalanine, tryptophan, tyrosine and combinations thereof. Other amino acids, including glutamine, asparagine, proline, cystine, aspartic acid, glutamic acid, glycine, methionine, serine and threonine, may be interplaced within these primary structural motifs in a given case. Despite these variations, the disclosed peptides will adhere to the general structural motifs indicated, thereby preserving their uniqueness.

The first peptide template XZBZBXBXB corresponds to the peptide template RP-1, Sequence No. 3; and the second peptide template XBBXX corresponds to the peptide template RP-13, Sequence No. 14.

The antimicrobial peptides and derived metapeptides that potentiate antimicrobial activity of leukocytes and are active alone or in combination with other agents directly against organisms such as bacteria and fungi can thus comprise peptides having amino acid sequences selected from the group consisting essentially of combined amino acid sequences AL and LA, wherein A represents an antimicrobial domain consisting essentially of a first peptide template XZBZBXBXB and derivatives thereof selected from the group consisting of XZBBZBXBXB, BXZXB, BXZXZXB, XBBXZXBBX, and BBXZBBXZ, and a second peptide template XBBXX and derivatives thereof selected from the group consisting of XBBXBBX, XBBXXBBX, BXXBXXB, XBBZXX, XBBZXXBB, and XBBZXXBBXXZBBX and L represents a leukocyte potentiating domain consisting essentially of JJJCJCJJJJJ, and J is selected from X, Z and B. Thus, an example of AL can be: XZBZBXBXBJJJCJCJJJJJ; and an example of LA can be: JJJCJCJJJJJXZBZBXBXB.

Figure 3:
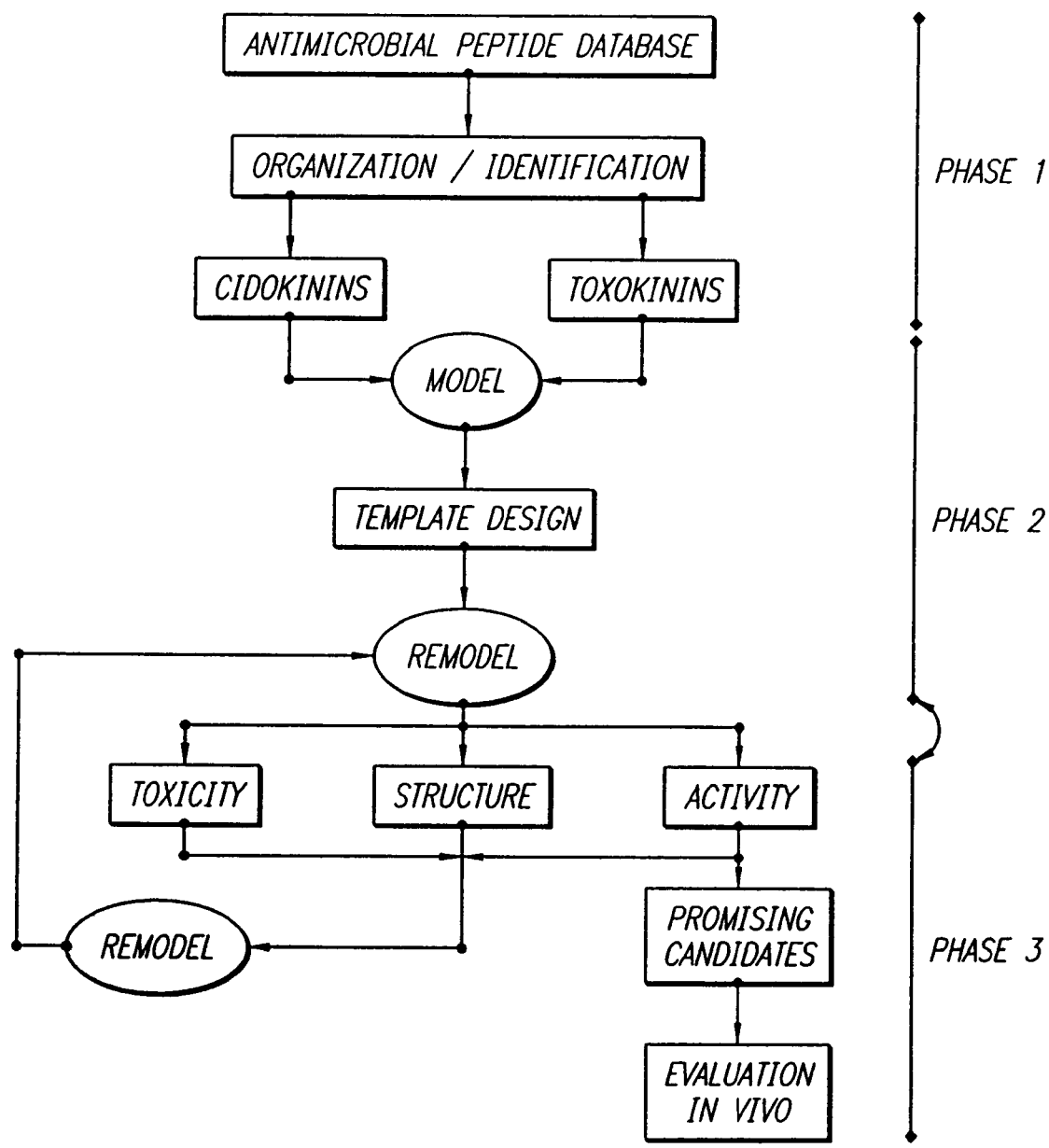
FIG. 3 is a flow chart illustrating the method for developing the novel antimicrobial peptides according to the principles of the invention.
Figure 4:
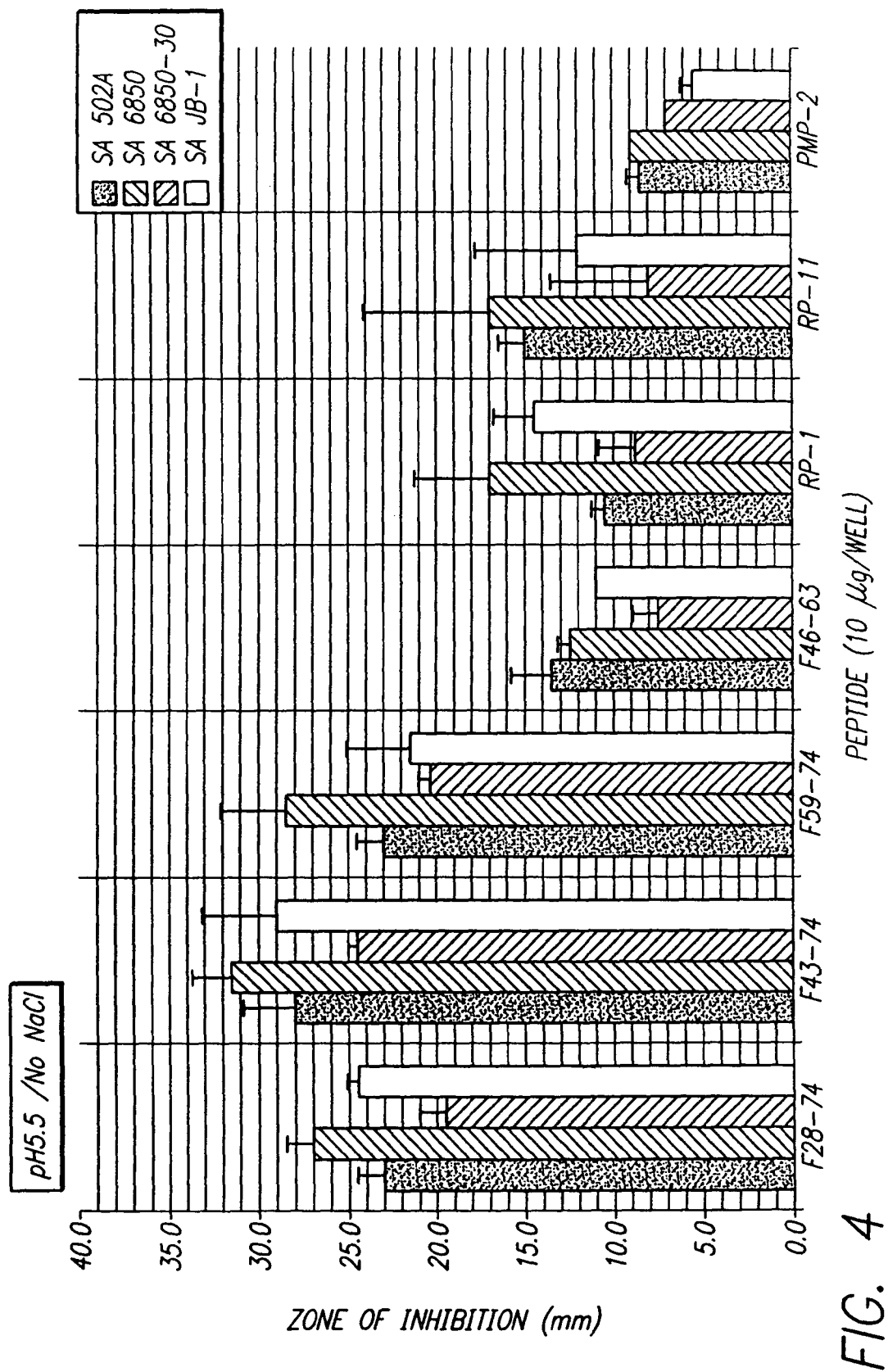
FIG. 4 is a two-dimensional graph of the antimicrobial spectra of the mean activity of peptides according to the invention against *Staphylococcus aureus* in a pharmaceutically acceptable carrier.
Figure 5:
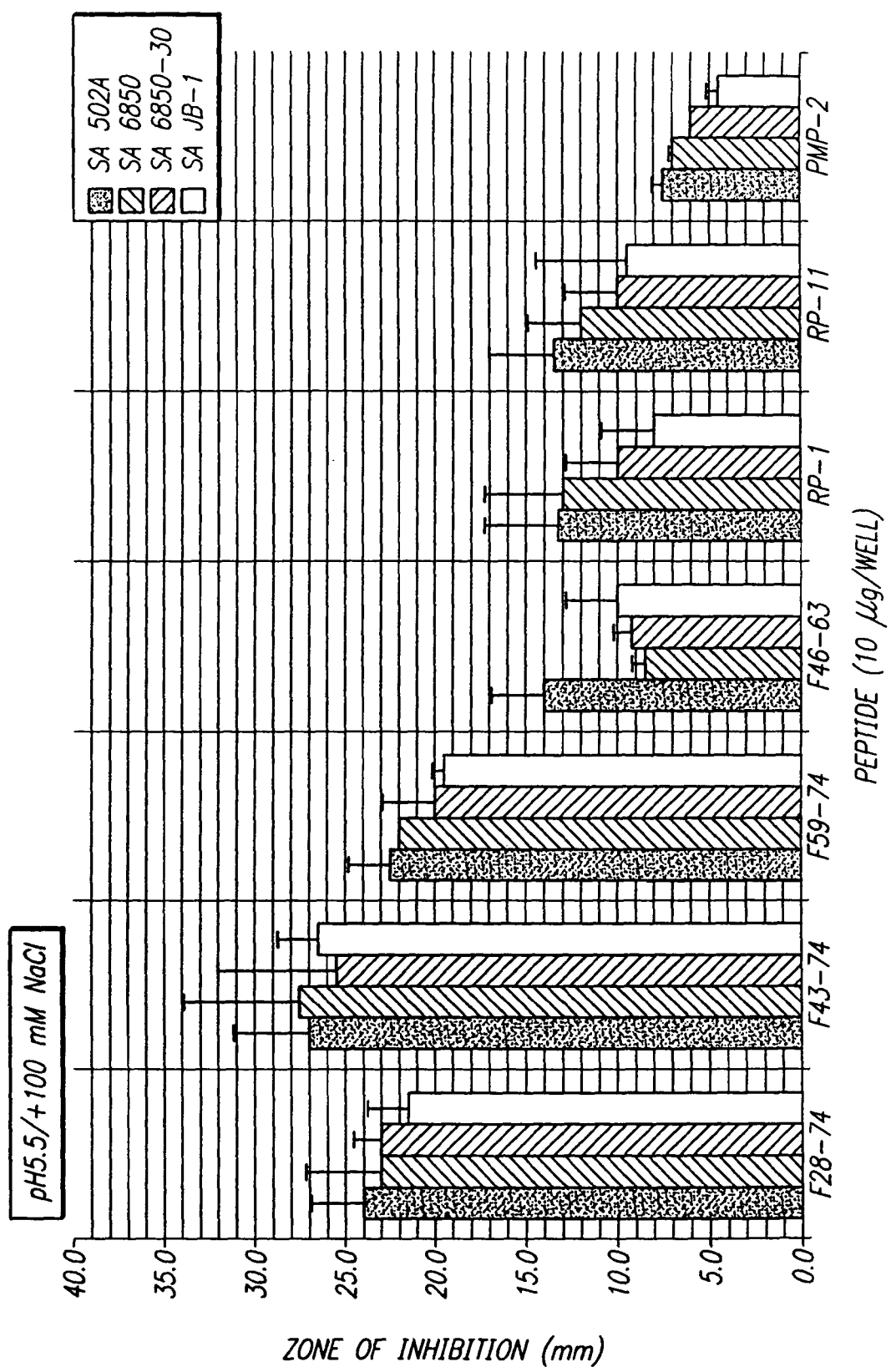
FIG. 5 is a two-dimensional graph of the antimicrobial spectra of the mean activity of peptides according to the invention against *Staphylococcus aureus* in another pharmaceutically acceptable carrier.
Figure 6:
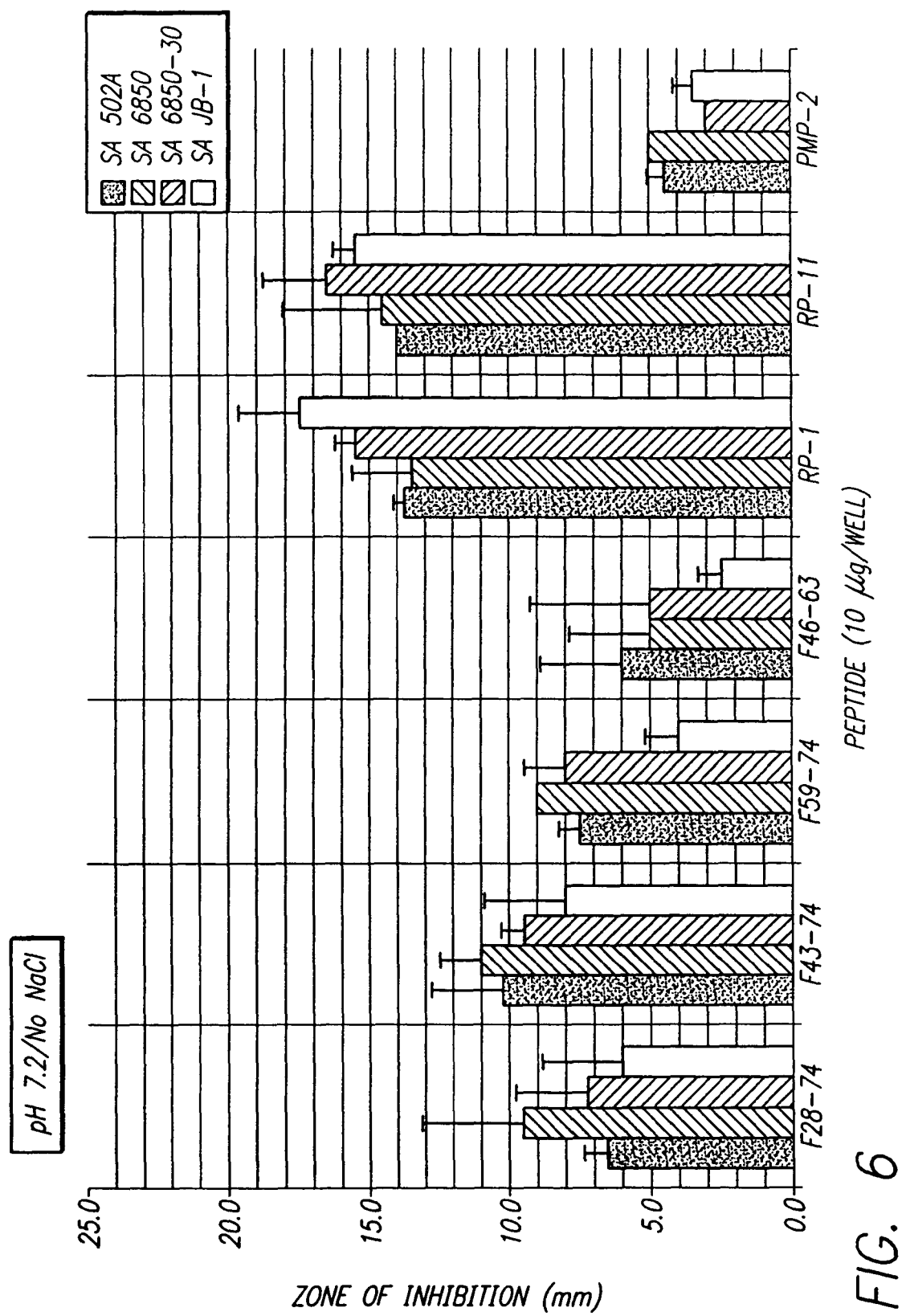
FIG. 6 is a two-dimensional graph of the antimicrobial spectra of the mean activity of peptides according to the invention against *Staphylococcus aureus* in another pharmaceutically acceptable carrier.
Figure 7:
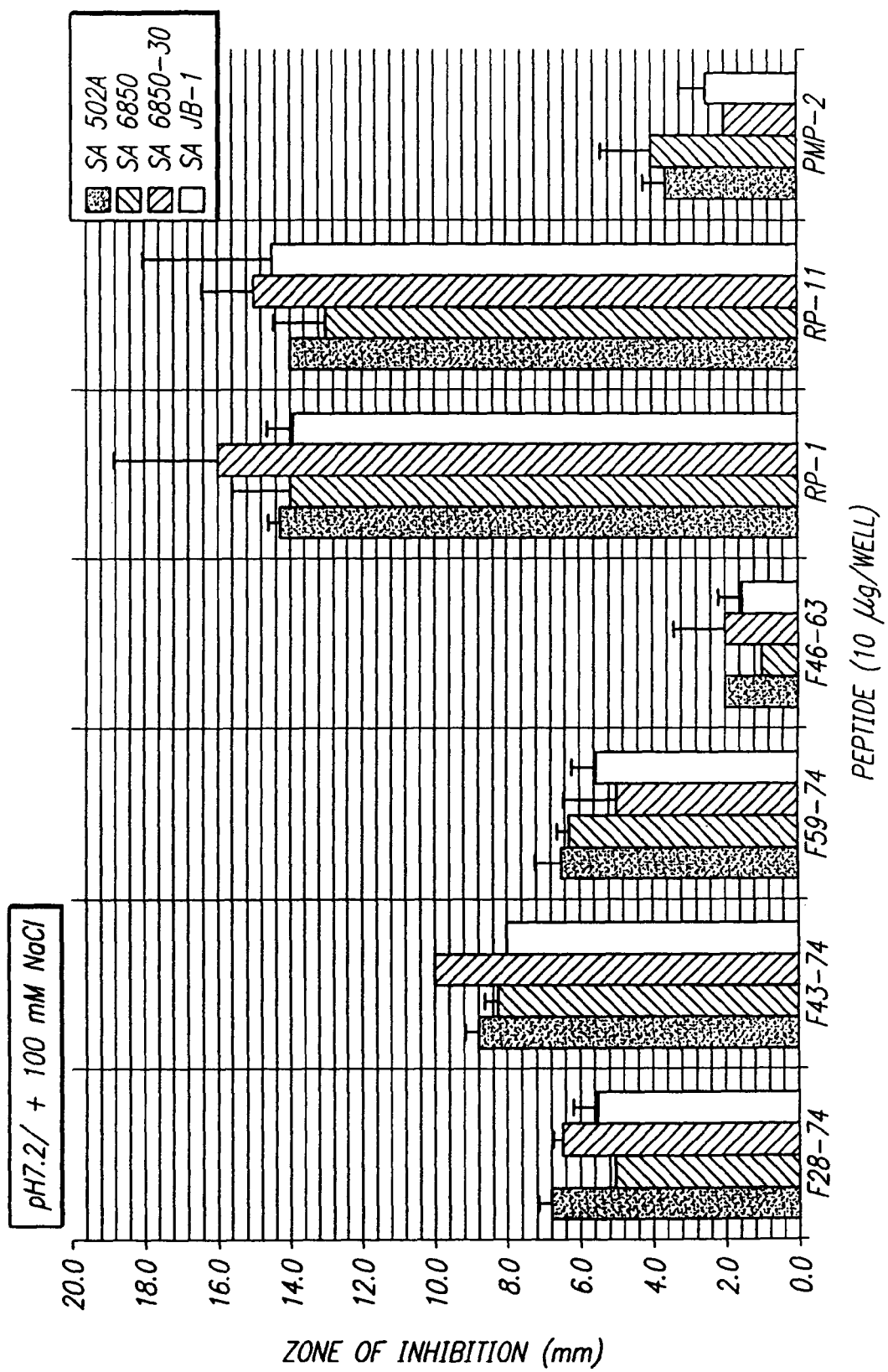
FIG. 7 is a two-dimensional graph of the antimicrobial spectra of the mean activity of peptides according to the invention against *Staphylococcus aureus* in another pharmaceutically acceptable carrier.
Figure 8:
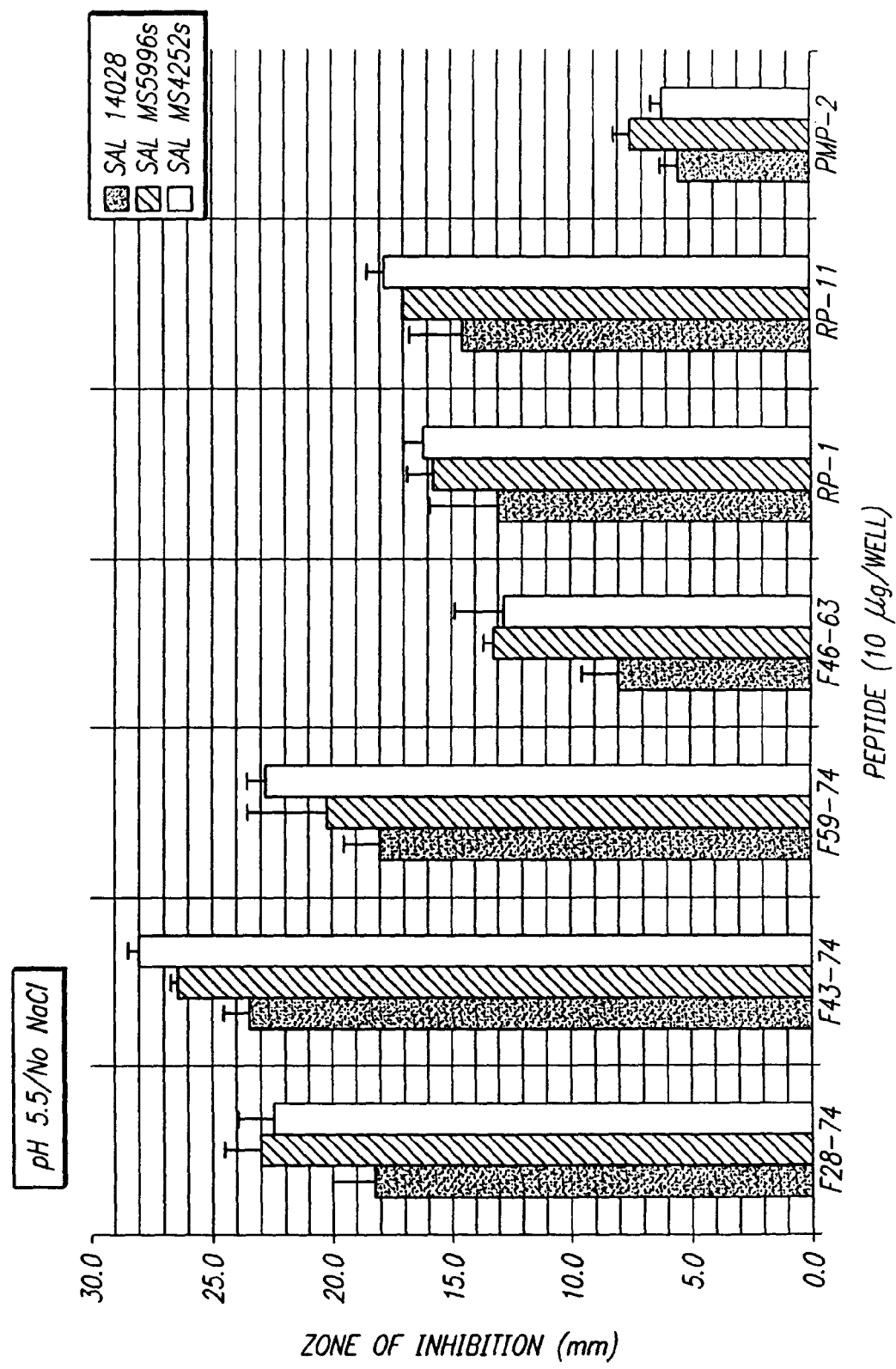
FIG. 8 is a two-dimensional graph of the antimicrobial spectra of the mean activity of peptides according to the invention against *Salmonella typhimurium* in a pharmaceutically acceptable carrier.
Figure 9:
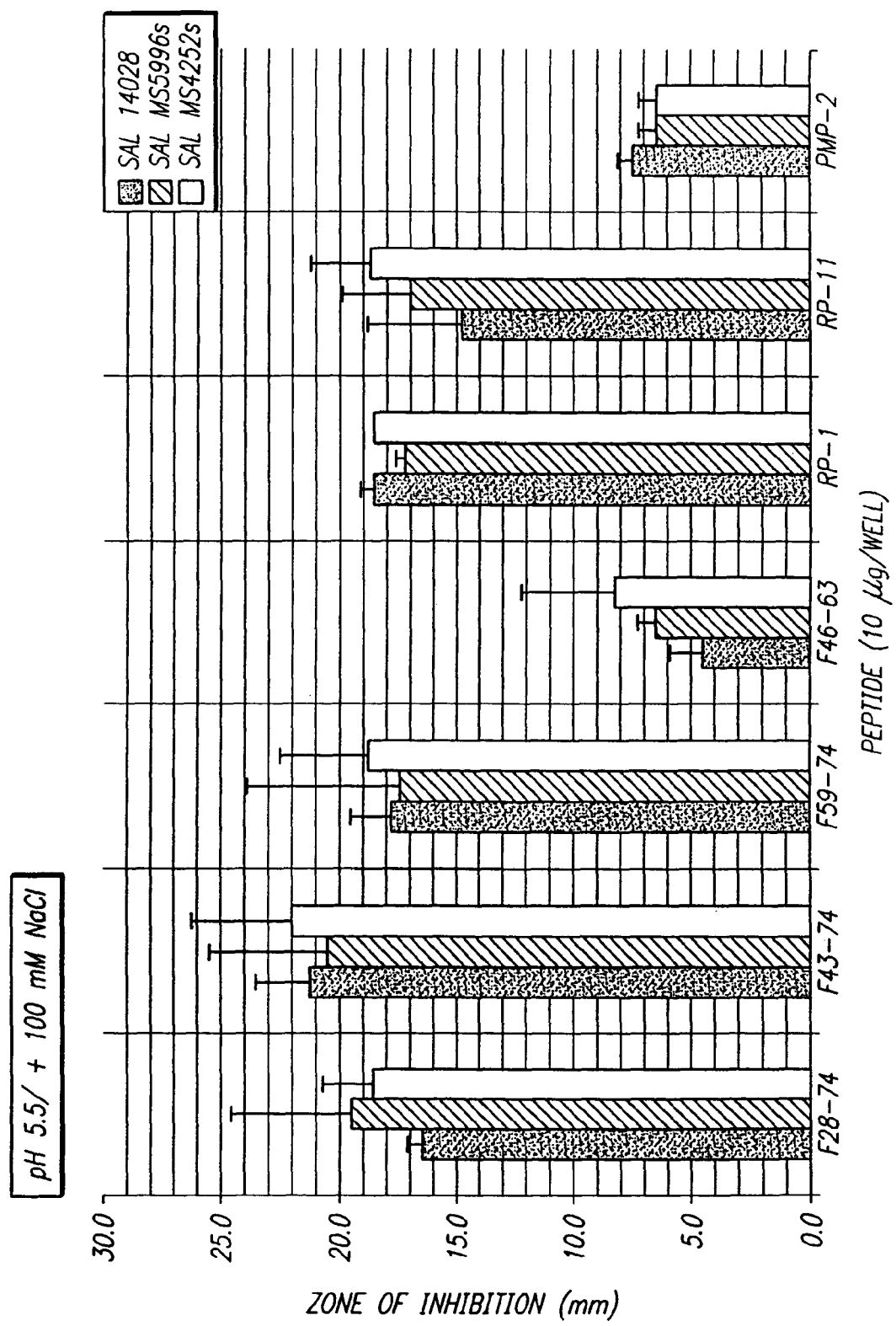
FIG. 9 is a two-dimensional graph of the antimicrobial spectra of the mean activity of peptides according to the invention against *Salmonella typhimurium* in another pharmaceutically acceptable carrier.
Figure 10:
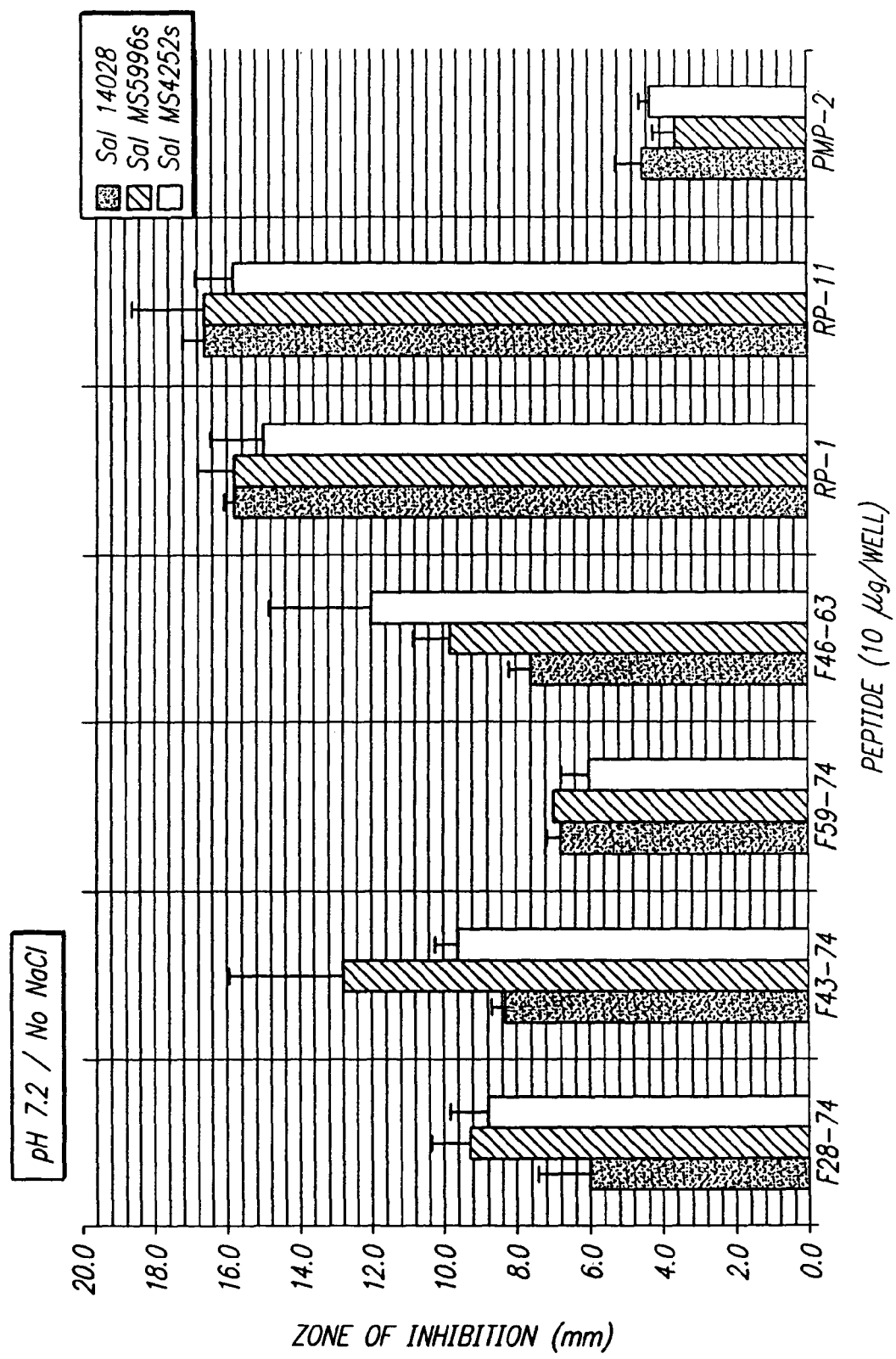
FIG. 10 is a two-dimensional graph of the antimicrobial spectra of the mean activity of peptides according to the invention against *Salmonella typhimurium* in another pharmaceutically acceptable carrier.
Figure 11:
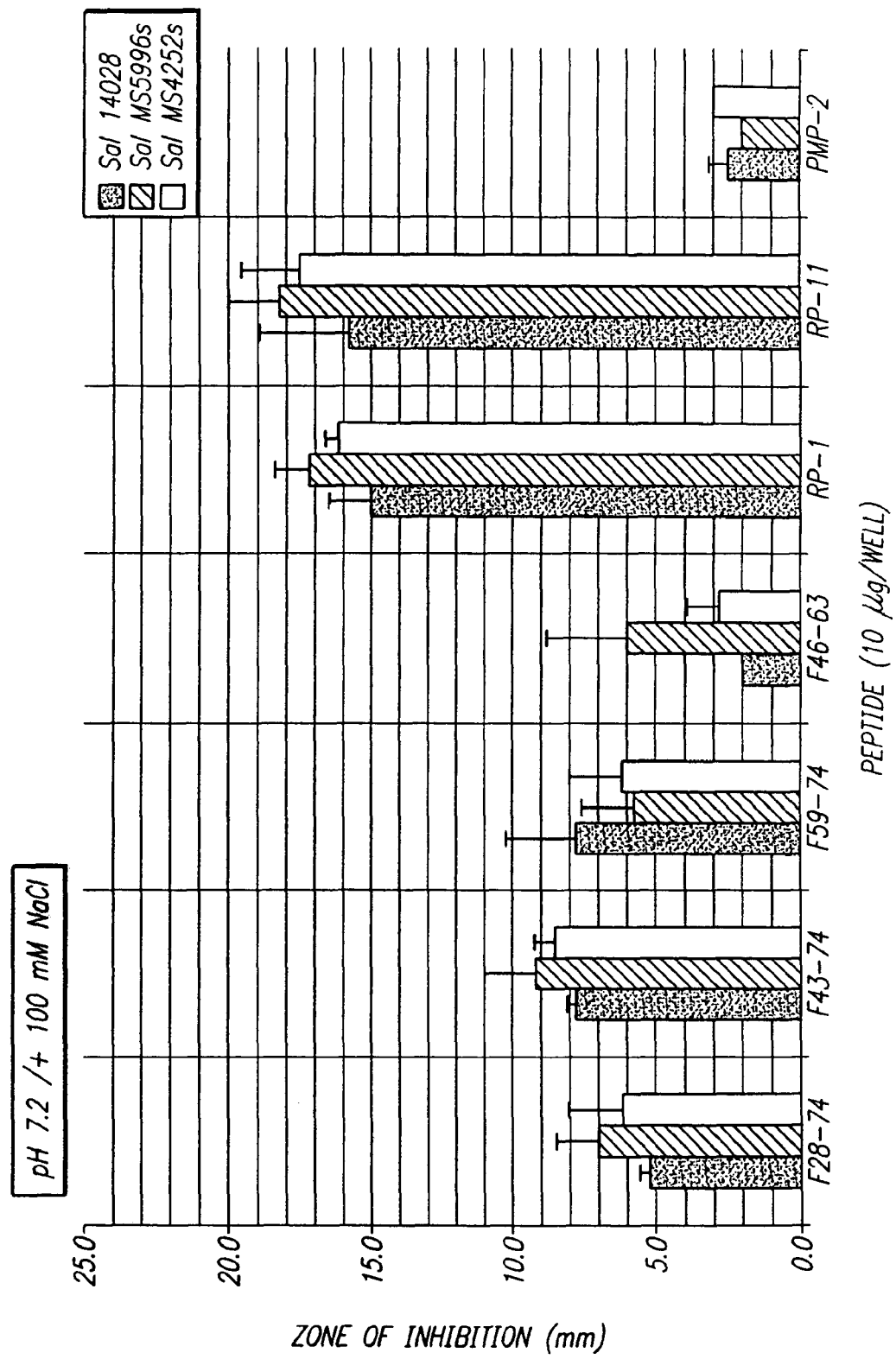
FIG. 11 is a two-dimensional graph of the antimicrobial spectra of the mean activity of peptides according to the invention against *Salmonella typhimurium* in another pharmaceutically acceptable carrier.

The method for developing the novel antimicrobial peptides according to the principles of the invention is summarized in the flow chart shown in FIG. 3. Initially, the antimicrobial peptide database is inspected visually, and the literature is reviewed, utilizing comparative sequence techniques, in order to identify likely antimicrobial peptide domains. Cidokinins (peptide domains associated with antimicrobial activity) and toxokinins (peptide domains associated with mammalian cell toxicity) are organized and domains and structural motifs are identified, and modeled to maximize the cidokinins and minimize the toxokinins. Similarly, immunopotentiating and directly microbicidal peptides may be derived in this manner. From this modeling, template designs such as RP-1 (Sequence No. 3), RP-13 (Sequence No. 14), or others are devised, and in turn are used for remodeling, by testing for toxicity, structure and antimicrobial activity, to identify promising candidates for further evaluation in vivo.

The antimicrobial peptides of the invention can include truncations, extensions, combinations, mosaics, or fusions of any of the above template peptides (e.g., PMP-2, Sequence No. 1), analogues derived from the approaches contained herein (e.g., RP-1 or Sequence No. 3), or modified analogues thereof as described above. Examples of such truncation, extension, combination, mosaic, and/or fusion sequences are described below:

A. Truncation Example:

PMP-2 (Sequence No. 1) is a 74 residue (amino acids 1-74) antimicrobial peptide. Novel antimicrobial peptides may be derived from truncation of PMP-2 (Sequence No. 1), or any of the peptides or their derivatives described herein. For example, the novel effective antimicrobial peptide FX, Sequence No. 30, is a truncation of PMP-2, Sequence No. 1, utilizing residues 45-74:

Ile Ala Thr Lys Lys Asn Gly Arg Lys Leu Cys Leu Asp Leu Gln

10

Ala Ala Leu Tyr Lys Lys Lys Ile Ile Lys Lys Leu Leu Glu Ser

20

Another novel effective antimicrobial peptide resulting from truncation of PMP-2, Sequence No. 1, is PMP-2 residues 28-74 (F28-74, Sequence No. 31, with 47 residues; linear/fold; internal fragment) having the following sequence:

```
Thr Asn Leu Glu Leu Ile Lys Ala Gly Gly His Cys Pro Thr Ala Asn
                               10

Leu Ile Ala Thr Lys Lys Asn Gly Arg Lys Leu Cys Leu Asp Leu Gln
                20                              30

Ala Ala Leu Tyr Lys Lys Lys Ile Ile Lys Lys Leu Leu Glu Ser
                        40
```

Another novel effective antimicrobial peptide that is a truncation fragment of PMP-2, Sequence No. 1, is PMP-2 residues 43-74 (F43-74, Sequence No. 32, with 32 residues; linear; internal fragment) having the following sequence:

```
Asn Leu Ile Ala Thr Lys Lys Asn Gly Arg Lys Leu Cys Leu Asp Leu
                            10

Gln Ala Ala Leu Tyr Lys Lys Lys Ile Ile Lys Lys Leu Leu Glu Ser
                20                              30
```

Another novel effective antimicrobial peptide derived by truncation of PMP-2, Sequence No. 1, is PMP-2 residues 59-74 (F59-74, Sequence No. 33, with 16 residues; linear; internal fragment):

```
Gln Ala Ala Leu Tyr Lys Lys Lys Ile Ile Lys Lys Leu Leu Glu Ser
                            10
```

B. Extension Example:

RP-1 (Sequence No. 3) is an 18 residue antimicrobial peptide. Novel antimicrobial peptides may be derived from extension of RP-1 or any of the other peptides, fragments, or derivatives described herein.

For example, the novel antimicrobial peptide RP-1 extension by RP-1 residues 1-10 (RP-1+RP-1-10, Sequence No. 34, having 28 residues; linear; internal fragment) has the following sequence:

```
Ala Leu Tyr Lys Lys Phe Lys Lys Lys Leu Leu Lys Ser Leu Lys Arg
                            10

Leu Gly Ala Leu Tyr Lys Lys Phe Lys Lys Lys Leu
                20
```

C. Combination/Fusion Example:

RP-1 (Sequence. No. 3) is an 18 residue antimicrobial peptide. RP-13 (Sequence No. 14) is a 17 residue antimicrobial peptide. Novel antimicrobial peptides may be derived from combination of RP-1 with RP-13 or any of the other peptides, fragments, or derivatives described herein.

For example, the novel antimicrobial peptide RP-1 combination with RP-13 (RP-1:RP-13, Sequence No. 35, with 35 residues; linear; internal fragment) has the following sequence:

```
Ala Leu Tyr Lys Lys Phe Lys Lys Lys Leu Leu Lys Ser Leu Lys Arg
                                        10

Leu Gly Ala Thr Lys Lys Asn Gly Arg Lys Leu Cys Leu Asp Leu Gln
                    20                              30

Ala Ala Leu
```

Any of the truncations, extensions, or combinations of any of the above peptides may occur in any orientation. For example, an N-terminal portion of RP-1 (Sequence No. 3) may be combined with a C-terminal portion of RP-13. Alternatively, a C-terminal portion of RP-1 may be combined with an N-terminal portion of RP-13. Likewise, other internal fragments may be oriented either N- or C-terminally in any of the above modifications.

Further examples of the modifications that can be made to promising peptides are set forth below, beginning with various peptides as the parent template to which modifications are made:

```
RP-1 (parent template, Sequence No. 3):
Ala Leu Tyr Lys Lys Phe Lys Lys Lys Leu Leu Lys Ser Leu Lys Arg Leu Gly OC-RP-1 (insert Cys at 0, Sequence No. 37):
Cys Ala Leu Tyr Lys Lys Phe Lys Lys Lys Leu Leu Lys Ser Leu Lys Arg Leu Gly 13C-RP-1 (insert Cys at 13, Sequence No. 38):
Ala Leu Tyr Lys Lys Phe Lys Lys Lys Leu Leu Lys Cys Leu Lys Arg Leu Gly 19C-RP-1 (insert Cys at 19, Sequence No. 39):
Ala Leu Tyr Lys Lys Phe Lys Lys Lys Leu Leu Lys Ser Leu Lys Arg Leu Gly Cys OC, 19C-RP-1 (insert Cys at 0, 19, Sequence No. 40):
Cys Ala Leu Tyr Lys Lys Phe Lys Lys Lys Leu Leu Lys Ser Leu Lys Arg Leu Gly Cys RP-1-2R (increased + charge, Sequence No. 41):
Ala Arg Tyr Lys Lys Phe Lys Lys Lys Leu Leu Lys Ser Leu Lys Arg Leu Gly RP-1-10F (increased steric bulk, Sequence No. 42):
Ala Leu Tyr Lys Lys Phe Lys Lys Lys Phe Leu Lys Ser Leu Lys Arg Leu Gly RP-1-2R10F (increased charge, bulk, Sequence No. 43):
Ala Arg Tyr Lys Lys Phe Lys Lys Lys Phe Leu Lys Ser Leu Lys Arg Leu Gly RP-1-retro (retromer, Sequence No. 44):
Gly Leu Arg Lys Leu Ser Lys Leu Leu Lys Lys Lys Phe Lys Lys Tyr Leu Ala RP-13-retro (retromer, Sequence No. 45):
Leu Ala Ala Gln Leu Asp Leu Cys Leu Lys Arg Gly Asn Lys Lys Thr Ala nRP-1:cRP-13 (fusion: nRP-1, cRP-13, Sequence No. 46):
Ala Leu Tyr Lys Lys Phe Lys Lys Lys Leu Cys Leu Asp Leu Gln Ala Ala Leu nRP-13:cRP-1 (fusion: nRP-13, cRP-I, Sequence No. 47):
Aia Thr Lys Lys Asn Gly Arg Lys Leu Cys Leu Lys Ser Leu Lys Arg Leu Gly
```

Parent Sequence (1):

```
PMP-2₄₆₋₆₆ (RP-13-TET, Sequence No. 48):
Ala Thr Lys Lys Asn Gly Arg Lys Leu Cys Leu Asp Leu Gln Ala Ala Leu Tyr Lys Lys Lys Charge Conservation Substitution:
Lys to Arg (2) (2,3R-RP-13-TET, Sequence No. 49):
Ala Thr Arg Arg Asn Gly Arg Arg Leu Cys Leu Asp Leu Gln Ala Ala Leu Tyr Arg Arg Arg Charge Conservation Substitution:
Arg to Lys (3) (7K-RP-13-TET, Sequence No. 50):
Ala Thr Lys Lys Asn Gly Lys Lys Leu Cys Leu Asp Leu Gln Ala Ala Leu Tyr Lys Lys Lys Charge Conservation Substitution:
Asp to Glu (4) (12E-RP-13-TET, Sequence No. 51):
Ala Thr Lys Lys Asn Gly Arg Lys Leu Cys Leu Glu Leu Gln Ala Ala Leu Tyr Lys Lys
```

-continued

Lys

Charge Reversion Substitution:
Lys to Glu (5) (3,4,8,19,20,21E-RP-13-TET, Sequence No. 52):
Ala Thr Glu Glu Asn Gly Arg Glu Leu Cys Leu Asp Leu Gln Ala Ala Leu Tyr Glu Glu Glu Charge Reversion Substitution:
Asp to Lys 6) (12K-RP-13-TET, Sequence No. 53):
Ala Thr Lys Lys Asn Gly Arg Lys Leu Cys Leu Lys Leu Gln Ala Ala Leu Tyr Lys Lys Lys Charge Reversion Substitution:
Arg to Glu (7) (7E-RP-13-TET, Sequence No. 54):
Ala Thr Lys Lys Asn Gly Glu Lys Leu Cys Leu Asp Leu Gln Ala Ala Leu Tyr Lys Lys Lys Charge Neutralization Substitution:
Arg to Gly (8) (7G-RP-13-TET, Sequence No. 55):
Ala Thr Lys Lys Asn Gly Gly Lys Leu Cys Leu Asp Leu Gln Ala Ala Leu Tyr Lys Lys Lys Charge Neutralization Substitution:
Asp to Gly (9) (12G-RP-13-TET, Sequence No. 56):
Ala Thr Lys Lys Asn Gly Arg Lys Leu Cys Leu Gly Leu Gln Ala Ala Leu Tyr Lys Lys Lys Aromatic Substitution:
Tyr to Phe (10) (18F-RP-I3-TET, Sequence No. 57):
Ala Thr Lys Lys Asn Gly Arg Lys Leu Cys Leu Asp Leu Gln Ala Ala Leu Phe Lys Lys Lys Aromatic Substitution:
Tyr to Trp (11) (18W-RP-13-TET, Sequence No. 58):
Ala Thr Lys Lys Asn Gly Arg Lys Leu Cys Leu Asp Leu Gln Ala Ala Leu Trp Lys Lys Lys Retromer peptide (12) (RP-13-TET-retro, Sequence No. 59):
Lys Lys Lys Tyr Leu Ala Ala Gln Leu Asp Leu Cys Leu Lys Arg Gly Asn Lys Lys Thr Ala C-Terminus Truncation:

Parent Seq. (1) (RP-13-TRI, Sequence No. 60):
Ala Thr Lys Lys Asn Gly Arg Lys Leu Cys Leu Asp Leu Gln Ala Ala Leu Tyr Lys Lys Charge Conservation Substitution:
Lys to Arg (2) (3,4,8,19,20R-RP-13-TRI, Sequence No. 61):
Ala Thr Arg Arg Asn Gly Arg Arg Leu Cys Leu Asp Leu Gln Ala Ala Leu Tyr Arg Arg Charge Conservation Substitution:
Arg to Lys (3) (7K-RP-13-TRI, Sequence No. 62):
Ala Thr Lys Lys Asn Gly Lys Lys Leu Cys Leu Asp Leu Gln Ala Ala Leu Tyr Lys Lys Charge Conservation Substitution:
Asp to Glu (4) (12E-RP-13-TRI, Sequence No. 63):
Ala Thr Lys Lys Asn Gly Arg Lys Leu Cys Leu Glu Leu Gln Ala Ala Leu Tyr Lys Lys Charge Reversion Substitution:
Lys to Glu (5) (3,4,8,19,20E-RP-13-TRI, Sequence No. 64):
Ala Thr Glu Glu Asn Gly Arg Glu Leu Cys Leu Asp Leu Gln Ala Ala Leu Tyr Glu Glu Charge Reversion Substitution:
Asp to Lys (6) (12K-RP-13-TRI, Sequence No. 65):
Ala Thr Lys Lys Asn Gly Arg Lys Leu Cys Leu Lys Leu Gln Ala Ala Leu Tyr Lys Lys Charge Reversion Substitution:
Arg to Glu (7) (7E-RP-13-TRI, Sequence No. 66):
Ala Thr Lys Lys Asn Gly Glu Lys Leu Cys Leu Asp Leu Gln Ala Ala Leu Tyr Lys Lys -continued Charge Neutralization Substitution:
Arg to Gly (8) (7G-RP-13-TRI, Sequence No. 67):
Ala Thr Lys Lys Asn Gly Gly

```
Charge Conservation Substitution:
Arg to Lys (3) (RP-64, Sequence No. 86):
Thr Lys Lys Asn Gly Lys Lys Leu Cys Leu Asp Leu Gln Ala Ala Leu Tyr Lys Lys Charge Conservation Substitution:
Asp to Glu (4) (RP-65, Sequence No. 87):
Thr Lys Lys Asn Gly Arg Lys Leu Cys Leu Glu Leu Gln Aia Ala Leu Tyr Lys Lys Charge Reversion Substitution:
Lys to Glu (5) (RP-66, Sequence No. 88):
Thr Glu Glu Asn Gly Arg Glu Leu Cys Leu Asp Leu Gln Ala Ala Leu Tyr Glu Glu Charge Reversion Substitution:
Asp to Lys (6) (RP-67, Sequence No. 89):
Thr Lys Lys Asn Gly Arg Lys Leu Cys Leu Lys Leu Gln Ala Ala Leu Tyr Lys Lys Charge Reversion Substitution:
Arg to Glu (7) (RP-68, Sequence No. 90):
Thr Lys Lys Asn Gly Glu Lys Leu Cys Leu Asp Leu Gln Ala Ala Leu Tyr Lys Lys Charge Neutralization Substitution:
Arg to Gly (8) (RP-69, Sequence No. 91):
Thr Lys Lys Asn Gly Gly Lys Leu Cys Leu Asp Leu Gln Ala Ala Leu Tyr Lys Lys Charge Neutralization Substitution:
Asp to Gly (9) (RP-70, Sequence No. 92):
Thr Lys Lys Asn Gly Arg Lys Leu Cys Leu Gly Leu Gln Ala Ala Leu Tyr Lys Lys Aromatic Substitution:
Tyr to Phe (10) (RP-71, Sequence No. 93):
Thr Lys Lys Asn Gly Arg Lys Leu Cys Leu Asp Leu Gln Ala Ala Leu Phe Lys Lys Aromatic Substitution:
Tyr to Trp (11) (RP-72, Sequence No. 94):
Thr Lys Lys Asn Gly Arg Lys Leu Cys Leu Asp Leu Gln Ala Ala Leu Trp Lys Lys Retromer peptide (12) (RP-73, Sequence No. 95):
Lys Lys Tyr Leu Ala Ala Gln Leu Asp Leu Cys Leu Lys Arg Gly Asn Lys Lys Thr
```

The antimicrobial peptides of the invention can be utilized as 1) individual antimicrobial agents, 2) antimicrobial agents in combination with other antimicrobial peptides herein, 3) agents that enhance, potentiate, or restore efficacy of conventional antimicrobials, such as fluoroquinolones, tetracyclines, macrolides, beta-lactams, aminoglycosides, anti-metabolites, azoles, polyenes, or anti-virals, 4) agents that enhance the antimicrobial functions of leukocytes such as neutrophils, 5) prophylactic agents for the prevention of infectious diseases, 6) antimicrobial components of vascular catheters or indwelling prosthetic devices, 7) disinfectants or preservatives for use in foods, cosmetics, contact lens solutions, and the like, and 8) agents to improve efficiency of molecular biology techniques (e.g., transformation). The novel antimicrobial peptides of the invention can, for example, be formulated in a pharmaceutically acceptable carrier, to form 1) powdered or liquid formulations in buffers suitable for intravenous administration, 2) solid or liquid formulations for oral administration, 3) opthalmalogic solutions or ointments, 4) topical solutions or ointments, 5) aerosolized suspensions, lavage, or inhalation formulation, and 6) any combination of the above with medical instrumentation or materials. As an example, the mean activity of several peptides according to the invention, in various pharmaceutically acceptable carrier solutions, against *Staphylococcus aureus* and *Salmonella typhimurium*, is illustrated in FIGS. 4 to 11.

D. Determination of Antimicrobial Peptide In Vitro Activity by Using an Agarose Radial Diffusion Assay Introduction:

The following assay is designed to measure the relative antimicrobial activity of peptides by determining zones of growth inhibition.

Methods:

Antimicrobial Peptide Preparation:

Stock concentrations of antimicrobial peptides are prepared at 1 mg/mL in 0.01% acetic acid are adjusted to pH 7.2.

Media Preparation:

Molecular grade agarose (1.0%) in 10 mM $NaH_2PO_4H_2O$ is autoclaved for 15 minutes at 121° C., then held in a water-bath set at 48° C. until use. Mueller Hinton II overlay agarose is prepared by adding molecular grade agarose to Mueller Hinton II Broth at a final concentration of 1.0%, autoclaving for 10 minutes at 121° C., then holding at 48° C. until use.

Inoculum Preparation:

Trypticase Soy Broth (TSB) (10 mL) is inoculated with overnight growth of the test organism and incubated three to six hours until organism reaches log phase. The cells are collected by centrifugation, washed in PBS, then 0.01% acetic acid adjusted to pH 7.2. The pellet is resuspended in TSB and standardized to a 0.5 McFarland turbidity standard. A 10 µl aliquot of the inoculum is added to 10 mL of 1.0% molecular grade agarose cooled to 48° C. resulting in a final inoculum concentration of $5 \times 10^5$ CFU/mL. The suspension is poured into a 15×100 mm petri dish and allowed to solidify.

After solidification has occurred, five 4 mm diameter wells are bored into the agarose. The central well is used as the acetic acid control while 10 µA of peptide stock solution is added to each of the other well resulting in a final concentration of 10 µg peptide/well. The plates are incubated upright for three hours at 37° C., then overlaid with 10 mL of Mueller Hinton II agarose. After the overlay solidifies, the plates are inverted and incubated overnight at 37° C.

Activity Determination:

Zones of growth inhibition are measured. The larger the zone size, the greater the antimicrobial activity of the peptide. The lack of a zone is an indication of no antimicrobial activity against the target organism.

E. Investigation of the Acute Toxicity of Antimicrobial Peptides in a Murine Model When Administered by a Single Intravenous, Intraperitoneal. Intramuscular or Subcutaneous Injection Introduction:

The acute toxicity of the antimicrobial peptides can be determined by dosing mice by intravenous (IV), intraperitoneal (IP.), intramuscular (IM.) or subcutaneous (SC.) injection. The highest dose for which the animals show no signs is considered to be the maximum tolerable does (MTD).

Methods:

Test Article Administration:

Swiss CD1 ICRBR male mice of approximately 5-6 weeks of age are weighed and randomized into groups of four mice. The antimicrobial peptide test article is administered as a single IV, SC., IM or IP injection to the first mouse in each group then the animal is observed for 10 to 30 min. Based on the mortality and morbidity outcome of this administration, the test article dose, dose volume and route of administration is reassessed before the test article is administrated to the next animal. The individual dose volume for administration will fall within the range of 5-15 mL/kg with the actual dose administered based on the weight of each animal on the day of the experiment.

Observations Upon Administration

Each mouse is to be observed 0 to 30 min post administration and again at 1-2, 4-6 and 24 hours. Surviving mice are observed once daily for the next 6 days. Observations include the activity level of the mouse as well as any physical side effects of the dose. The maximum tolerable dose (MTD) in mg/Kg is the concentration of peptide for which no observable adverse effect in noted. Antimicrobial peptides with MTD values of >40 mg/Kg are preferred.

It will be apparent from the foregoing that while particular forms of the invention have been illustrated and described, various modifications can be made without departing from the spirit and scope of the invention.

What is claimed is:

1. An antimicrobial peptide composition comprising: a peptide of no more than 20 amino acid residues, wherein said peptide comprises an amino acid core sequence of $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$-$aa_{17}$, wherein $aa_1$ is the amino-terminus of the peptide and is alanine; $aa_2$ is threonine; $aa_3$ and $aa_4$ are lysine; $aa_5$ is asparagine; $aa_6$ is glycine; $aa_7$ is arginine; $aa_8$ is lysine; $aa_9$, $aa_{11}$, $aa_{13}$, and $aa_{17}$ are leucine; $aa_{14}$ is glutamine, $aa_{15}$ and $aa_{16}$ are alanine; and $aa_{10}$ and $aa_{12}$ are independently:
  (i) an amino acid selected from the group consisting of asparagine, cysteine, aspartic acid, glutamic acid and methionine, or
  (ii) an amino acid having a modified amino acid group selected from the group consisting of N-$^\epsilon$monomethyl-lysine, a β-branched amino acid, a N-methyl amino acid, an α,β-dehydro amino acid, an α,α-dialkyl amino acid and a fluorinated amino acid.

2. The antimicrobial peptide composition of claim 1, wherein said $aa_{10}$ is cysteine or $aa_{12}$ is aspartic acid.

3. The antimicrobial peptide composition of claim 1, wherein said $aa_{10}$ or $aa_{12}$ is asparagine.

4. The antimicrobial peptide composition of claim 1, wherein said $aa_{10}$ or $aa_{12}$ is aspartic acid.

5. The antimicrobial peptide composition of claim 1, wherein said $aa_{10}$ or $aa_{12}$ is glutamic acid.

6. The antimicrobial peptide composition of claim 1, wherein said $aa_{10}$ or $aa_{12}$ is methionine.

7. The antimicrobial peptide composition of claim 1, wherein said $aa_{10}$ or $aa_{12}$ is N-$^\epsilon$monomethyl-lysine, a β-branched amino acid, a N-methyl amino acid, an α,β-dehydro amino acid, an α,α-dialkyl amino acid and a fluorinated amino acid.

8. The antimicrobial peptide composition of claim 1, wherein said $aa_{10}$ or $aa_{12}$ is N-$^\epsilon$monomethyl-lysine.

9. The antimicrobial peptide composition of claim 1, wherein said $aa_{10}$ or $aa_{12}$ is a β-branched amino acid.

10. The antimicrobial peptide composition of claim 1, wherein said $aa_{10}$ or $aa_{12}$ is a N-methyl amino acid.

11. The antimicrobial peptide composition of claim 1, wherein said $aa_{10}$ or $aa_{12}$ is an α,β-dehydro amino acid.

12. The antimicrobial peptide composition of claim 1, wherein said $aa_{10}$ or $aa_{12}$ is an α,α-dialkyl amino acid.

13. The antimicrobial peptide composition of claim 1, wherein said $aa_{10}$ or $aa_{12}$ is a fluorinated amino acid.

14. An antimicrobial peptide composition comprising: a peptide of no more than 20 amino acid residues, wherein said peptide comprises an amino acid core sequence of $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$-$aa_{17}$, wherein $aa_1$ is the amino-terminus of the peptide and is alanine; $aa_2$ is threonine; $aa_3$ and $aa_4$ are lysine; $aa_5$ is asparagine; $aa_6$ is glycine; $aa_7$ is arginine; $aa_8$ is lysine; $aa_9$, $aa_{11}$, $aa_{13}$, and $aa_{17}$ are leucine; $aa_{14}$ is glutamine, $aa_{15}$ and $aa_{16}$ are alanine; and $aa_{10}$ and $aa_{12}$ are independently a D-amino acid.

15. A fusion peptide comprising (a) a peptide of no more than 20 amino acid residues, wherein said peptide comprises an amino acid core sequence of $aa_1$-$aa_2$-$aa_3$-$aa_4$-$aa_5$-$aa_6$-$aa_7$-$aa_8$-$aa_9$-$aa_{10}$-$aa_{11}$-$aa_{12}$-$aa_{13}$-$aa_{14}$-$aa_{15}$-$aa_{16}$-$aa_{17}$, wherein $aa_1$ is the amino-terminus of the peptide and is alanine; $aa_2$ is threonine; $aa_3$ and $aa_4$ are lysine; $aa_5$ is asparagine; $aa_6$ is glycine; $aa_7$ is arginine; $aa_8$ is lysine; $aa_9$, $aa_{11}$, and $aa_{17}$ are leucine; $aa_{14}$ is glutamine, $aa_{15}$ and $aa_{16}$ are alanine; and $aa_{10}$ and $aa_{12}$ are independently:
   (i) an amino acid selected from the group consisting of asparagine, cysteine, aspartic acid, glutamic acid and methionine, or
   (ii) an amino acid having a modified amino acid group selected from the group consisting of N-$^\epsilon$monomethyl-lysine, a β-branched amino acid, a N-methyl amino acid, an α,β-dehydro amino acid, an α,α-dialkyl amino acid, and a fluorinated amino acid, and (b) RP-1 (SEQ ID NO: 3).

* * * * *

SEQUENCE LISTING

```
<160> NUMBER OF SEQ ID NOS: 111

<210> SEQ ID NO 1
<211> LENGTH: 74
<212> TYPE: PRT
<213> ORGANISM: Oryctolagus cuniculus

<400> SEQUENCE: 1

Ser Asp Asp Pro Lys Glu Ser Glu Gly Asp Leu His Cys Val Cys Val
1               5                   10                  15

Lys Thr Thr Ser Leu Val Arg Pro Arg His Ile Thr Asn Leu Glu Leu
            20                  25                  30

Ile Lys Ala Gly Gly His Cys Pro Thr Ala Asn Leu Ile Ala Thr Lys
        35                  40                  45

Lys Asn Gly Arg Lys Leu Cys Leu Asp Leu Gln Ala Ala Leu Tyr Lys
    50                  55                  60

Lys Lys Ile Ile Lys Lys Leu Leu Glu Ser
65                  70

<210> SEQ ID NO 2
<211> LENGTH: 74
<212> TYPE: PRT
<213> ORGANISM: Oryctolagus cuniculus

<400> SEQUENCE: 2

Ser Asp Asp Pro Lys Glu Ser Glu Gly Asp Leu His Cys Val Cys Val
1               5                   10                  15

Lys Thr Thr Ser Leu Val Arg Pro Gly His Ile Thr Asn Leu Glu Leu
            20                  25                  30

Ile Lys Ala Gly Gly His Cys Pro Thr Ala Asn Leu Ile Ala Thr Lys
        35                  40                  45

Lys Asn Gly Arg Lys Leu Cys Leu Asp Leu Gln Ala Ala Leu Tyr Lys
    50                  55                  60

Lys Lys Ile Ile Lys Lys Leu Leu Glu Ser
65                  70

<210> SEQ ID NO 3
<211> LENGTH: 18
<212> TYPE: PRT
<213> ORGANISM: Artificial Sequence
<220> FEATURE:
<223> OTHER INFORMATION: Antimicrobiocidal peptide designed in part upon
``` microbiocidal domains from platelet microbial
proteins 1 and 2 (PMP-1 and PMP-2) from rabbits.

<400> SEQUENCE: 3

Ala Leu Tyr Lys Lys Phe Lys Lys Leu Leu Lys Ser Leu Lys Arg
1               5                   10                  15

Leu Gly

<210> SEQ ID NO 4
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 4

Ala Arg Tyr Lys Lys Phe Lys Lys Leu Leu Lys Ser
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 5

Lys Leu Tyr Arg Lys Phe Lys Asn Lys Leu Leu Lys Leu Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 6

Ala Arg Tyr Arg Lys Phe Lys Asn Lys Ile Leu Lys Ser
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 7

Ala Arg Tyr Arg Lys Phe Arg Asn Lys Ile Leu Arg Ser
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 8

Lys Leu Tyr Lys Lys Trp Lys Lys Leu Leu Lys Leu Lys
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 9

Ala Leu Tyr Lys Lys Trp Lys Asn Lys Leu Leu Lys Ser
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 10

Lys Leu Tyr Lys Lys Trp Lys Asn Lys Leu Lys Arg Ser Leu Lys Arg
1               5                   10                  15

Leu Gly

<210> SEQ ID NO 11
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 11

Ala Leu Tyr Lys Lys Leu Phe Lys Lys Leu Leu Lys Arg
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 12

Gly Leu Tyr Lys Arg Leu Phe Lys Lys Leu Leu Lys Ser
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 13

```
Ala Leu Tyr Lys Arg Leu Phe Lys Lys Leu Lys Lys Phe
1               5                   10
```

```
<210> SEQ ID NO 14
<211> LENGTH: 17
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 14
```

```
Ala Thr Lys Lys Asn Gly Arg Lys Leu Cys Leu Asp Leu Gln Ala Ala
1               5                   10                  15

Leu
```

```
<210> SEQ ID NO 15
<211> LENGTH: 8
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 15
```

```
Arg Phe Glu Lys Ser Lys Ile Lys
1               5
```

```
<210> SEQ ID NO 16
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 16
```

```
Ser Ala Ile His Pro Ser Ser Ile Leu Lys Leu Glu Val Ile Cys Ile
1               5                   10                  15

Gly Val Leu Gln
            20
```

```
<210> SEQ ID NO 17
<211> LENGTH: 14
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 17
```

```
Tyr Ala Glu Arg Leu Cys Thr Cys Ser Ile Lys Ala Glu Val
1               5                   10
```

```
<210> SEQ ID NO 18
<211> LENGTH: 11
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.
```

<400> SEQUENCE: 18

Lys Phe Lys His Tyr Phe Phe Trp Lys Tyr Lys
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 19

Lys Gly Tyr Phe Tyr Phe Leu Phe Lys Phe Lys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 20

Lys Trp Lys Trp Trp Trp Trp Trp Lys Trp Lys
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 21

Pro Arg Ile Lys Lys Ile Val Gln Lys Lys Leu Ala Gly
1               5                   10

<210> SEQ ID NO 22
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 22

Lys Trp Val Arg Glu Tyr Ile Asn Ser Leu Glu Met Ser Lys Lys Gly
1               5                   10                  15

Leu Ala Gly

<210> SEQ ID NO 23
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 23

Glu Trp Val Gln Lys Tyr Val Ser Asp Leu Glu Leu Ser Ala Trp Lys
1               5                   10                  15

Lys Ile Leu Lys
            20

<210> SEQ ID NO 24
<211> LENGTH: 12
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 24

Ser Trp Val Gln Glu Tyr Val Tyr Asp Leu Glu Leu
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 25

Ala Asp Ser Gly Glu Gly Asp Phe Leu Ala Glu Gly Gly Gly Val Arg
1               5                   10                  15

<210> SEQ ID NO 26
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 26

Ala Asp Ser Gly Glu Gly Asp Phe Leu Ala Glu Gly Gly Gly Val Arg
1               5                   10                  15

Lys Leu Ile Lys
            20

<210> SEQ ID NO 27
<211> LENGTH: 13
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 27

Glu Gly Val Asn Asp Asn Glu Glu Gly Phe Phe Ser Ala
1               5                   10

<210> SEQ ID NO 28
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

```
<400> SEQUENCE: 28

Lys Phe Asp Lys Ser Lys Leu Lys Lys Thr Glu Thr Gln Glu Lys Asn
 1               5                  10                  15

Pro Leu

<210> SEQ ID NO 29
<211> LENGTH: 15
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits.

<400> SEQUENCE: 29

Ala Asn Leu Ile Ala Thr Lys Lys Asn Gly Arg Lys Leu Cys Leu
 1               5                  10                  15

<210> SEQ ID NO 30
<211> LENGTH: 30
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 30

Ile Ala Thr Lys Lys Asn Gly Arg Lys Leu Cys Leu Asp Leu Gln Ala
 1               5                  10                  15

Ala Leu Tyr Lys Lys Lys Ile Ile Lys Lys Leu Leu Glu Ser
            20                  25                  30

<210> SEQ ID NO 31
<211> LENGTH: 47
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 31

Thr Asn Leu Glu Leu Ile Lys Ala Gly Gly His Cys Pro Thr Ala Asn
 1               5                  10                  15

Leu Ile Ala Thr Lys Lys Asn Gly Arg Lys Leu Cys Leu Asp Leu Gln
            20                  25                  30

Ala Ala Leu Tyr Lys Lys Lys Ile Ile Lys Lys Leu Leu Glu Ser
        35                  40                  45

<210> SEQ ID NO 32
<211> LENGTH: 32
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 32

Asn Leu Ile Ala Thr Lys Lys Asn Gly Arg Lys Leu Cys Leu Asp Leu
 1               5                  10                  15

Gln Ala Ala Leu Tyr Lys Lys Lys Ile Ile Lys Lys Leu Leu Glu Ser
            20                  25                  30
```

<210> SEQ ID NO 33
<211> LENGTH: 16
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 33

Gln Ala Ala Leu Tyr Lys Lys Lys Ile Ile Lys Lys Leu Leu Glu Ser
 1               5                  10                  15

<210> SEQ ID NO 34
<211> LENGTH: 25
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 34

Ala Leu Tyr Lys Lys Phe Lys Lys Lys Leu Leu Lys Ser Leu Lys Arg
 1               5                  10                  15

Leu Gly Ala Leu Tyr Lys Lys Lys Leu
            20                  25

<210> SEQ ID NO 35
<211> LENGTH: 35
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 35

Ala Leu Tyr Lys Lys Phe Lys Lys Lys Leu Leu Lys Ser Leu Lys Arg
 1               5                  10                  15

Leu Gly Ala Thr Lys Lys Asn Gly Arg Lys Leu Cys Leu Asp Leu Gln
            20                  25                  30

Ala Ala Leu
        35

<210> SEQ ID NO 36
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 36

Ala Thr Lys Lys Asn Gly Arg Lys Leu Cys Leu Asp Leu Gln Ala Ala
 1               5                  10                  15

Leu Tyr

<210> SEQ ID NO 37
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial proteins 1 and 2 (PMP-1 and PMP-2) from rabbits

<400> SEQUENCE: 37

Cys Ala Leu Tyr Lys Lys Phe Lys Lys Lys Leu Leu Lys Ser Leu Lys
1               5                   10                  15

Arg Leu Gly

<210> SEQ ID NO 38
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 38

Ala Leu Tyr Lys Lys Phe Lys Lys Lys Leu Leu Lys Cys Leu Lys Arg
1               5                   10                  15

Leu Gly

<210> SEQ ID NO 39
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 39

Ala Leu Tyr Lys Lys Phe Lys Lys Lys Leu Leu Lys Ser Leu Lys Arg
1               5                   10                  15

Leu Gly Cys

<210> SEQ ID NO 40
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 40

Cys Ala Leu Tyr Lys Lys Phe Lys Lys Lys Leu Leu Lys Ser Leu Lys
1               5                   10                  15

Arg Leu Gly Cys
            20

<210> SEQ ID NO 41
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 41

Ala Arg Tyr Lys Lys Phe Lys Lys Lys Leu Leu Lys Ser Leu Lys Arg
1               5                   10                  15

Leu Gly

```
<210> SEQ ID NO 42
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 42

Ala Leu Tyr Lys Lys Phe Lys Lys Lys Phe Leu Lys Ser Leu Lys Arg
 1               5                  10                  15

Leu Gly

<210> SEQ ID NO 43
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 43

Ala Arg Tyr Lys Lys Phe Lys Lys Lys Phe Leu Lys Ser Leu Lys Arg
 1               5                  10                  15

Leu Gly

<210> SEQ ID NO 44
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 44

Gly Leu Arg Lys Leu Ser Lys Leu Leu Lys Lys Lys Phe Lys Lys Tyr
 1               5                  10                  15

Leu Ala

<210> SEQ ID NO 45
<211> LENGTH: 17
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 45

Leu Ala Ala Gln Leu Asp Leu Cys Leu Lys Arg Gly Asn Lys Lys Thr
 1               5                  10                  15

Ala

<210> SEQ ID NO 46
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 46
```

Ala Leu Tyr Lys Lys Phe Lys Lys Leu Cys Leu Asp Leu Gln Ala
1               5                   10                  15

Ala Leu

<210> SEQ ID NO 47
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 47

Ala Thr Lys Lys Asn Gly Arg Lys Leu Cys Leu Lys Ser Leu Lys Arg
1               5                   10                  15

Leu Gly

<210> SEQ ID NO 48
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 48

Ala Thr Lys Lys Asn Gly Arg Lys Leu Cys Leu Asp Leu Gln Ala Ala
1               5                   10                  15

Leu Tyr Lys Lys Lys
                20

<210> SEQ ID NO 49
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 49

Ala Thr Arg Arg Asn Gly Arg Arg Leu Cys Leu Asp Leu Gln Ala Ala
1               5                   10                  15

Leu Tyr Arg Arg Arg
                20

<210> SEQ ID NO 50
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 50

Ala Thr Lys Lys Asn Gly Lys Lys Leu Cys Leu Asp Leu Gln Ala Ala
1               5                   10                  15

Leu Tyr Lys Lys Lys
                20

<210> SEQ ID NO 51
<211> LENGTH: 21

<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 51

Ala Thr Lys Lys Asn Gly Arg Lys Leu Cys Leu Glu Leu Gln Ala Ala
1               5                   10                  15

Leu Tyr Lys Lys Lys
            20

<210> SEQ ID NO 52
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 52

Ala Thr Glu Glu Asn Gly Arg Glu Leu Cys Leu Asp Leu Gln Ala Ala
1               5                   10                  15

Leu Tyr Glu Glu Glu
            20

<210> SEQ ID NO 53
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 53

Ala Thr Lys Lys Asn Gly Arg Lys Leu Cys Leu Lys Leu Gln Ala Ala
1               5                   10                  15

Leu Tyr Lys Lys Lys
            20

<210> SEQ ID NO 54
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 54

Ala Thr Lys Lys Asn Gly Glu Lys Leu Cys Leu Asp Leu Gln Ala Ala
1               5                   10                  15

Leu Tyr Lys Lys Lys
            20

<210> SEQ ID NO 55
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits -continued

```
<400> SEQUENCE: 55

Ala Thr Lys Lys Asn Gly Gly Lys Leu Cys Leu Asp Leu Gln Ala Ala
1               5                   10                  15

Leu Tyr Lys Lys Lys
            20

<210> SEQ ID NO 56
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 56

Ala Thr Lys Lys Asn Gly Arg Lys Leu Cys Leu Gly Leu Gln Ala Ala
1               5                   10                  15

Leu Tyr Lys Lys Lys
            20

<210> SEQ ID NO 57
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 57

Ala Thr Lys Lys Asn Gly Arg Lys Leu Cys Leu Asp Leu Gln Ala Ala
1               5                   10                  15

Leu Phe Lys Lys Lys
            20

<210> SEQ ID NO 58
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 58

Ala Thr Lys Lys Asn Gly Arg Lys Leu Cys Leu Asp Leu Gln Ala Ala
1               5                   10                  15

Leu Trp Lys Lys Lys
            20

<210> SEQ ID NO 59
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 59

Lys Lys Lys Tyr Leu Ala Ala Gln Leu Asp Leu Cys Leu Lys Arg Gly
1               5                   10                  15

Asn Lys Lys Thr Ala
            20
```

<210> SEQ ID NO 60
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 60

Ala Thr Lys Lys Asn Gly Arg Lys Leu Cys Leu Asp Leu Gln Ala Ala
 1               5                  10                  15

Leu Tyr Lys Lys
            20

<210> SEQ ID NO 61
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 61

Ala Thr Arg Arg Asn Gly Arg Arg Leu Cys Leu Asp Leu Gln Ala Ala
 1               5                  10                  15

Leu Tyr Arg Arg
            20

<210> SEQ ID NO 62
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 62

Ala Thr Lys Lys Asn Gly Lys Lys Leu Cys Leu Asp Leu Gln Ala Ala
 1               5                  10                  15

Leu Tyr Lys Lys
            20

<210> SEQ ID NO 63
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 63

Ala Thr Lys Lys Asn Gly Arg Lys Leu Cys Leu Glu Leu Gln Ala Ala
 1               5                  10                  15

Leu Tyr Lys Lys
            20

<210> SEQ ID NO 64
<211> LENGTH: 20
<212> TYPE: PRT
<213> ORGANISM: Artificial Sequence
<220> FEATURE:

```
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 64

Ala Thr Glu Glu Asn Gly Arg Glu Leu Cys Leu Asp Leu Gln Ala Ala
 1               5                  10                  15

Leu Tyr Glu Glu
            20

<210> SEQ ID NO 65
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 65

Ala Thr Lys Lys Asn Gly Arg Lys Leu Cys Leu Lys Leu Gln Ala Ala
 1               5                  10                  15

Leu Tyr Lys Lys
            20

<210> SEQ ID NO 66
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 66

Ala Thr Lys Lys Asn Gly Glu Lys Leu Cys Leu Asp Leu Gln Ala Ala
 1               5                  10                  15

Leu Tyr Lys Lys
            20

<210> SEQ ID NO 67
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 67

Ala Thr Lys Lys Asn Gly Gly Lys Leu Cys Leu Asp Leu Gln Ala Ala
 1               5                  10                  15

Leu Tyr Lys Lys
            20

<210> SEQ ID NO 68
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 68

Ala Thr Lys Lys Asn Gly Arg Lys Leu Cys Leu Gly Leu Gln Ala Ala
```

```
                1               5                  10                 15

Leu Tyr Lys Lys
            20

<210> SEQ ID NO 69
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 69

Ala Thr Lys Lys Asn Gly Arg Lys Leu Cys Leu Asp Leu Gln Ala Ala
1               5                   10                  15

Leu Phe Lys Lys
            20

<210> SEQ ID NO 70
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 70

Ala Thr Lys Lys Asn Gly Arg Lys Leu Cys Leu Asp Leu Gln Ala Ala
1               5                   10                  15

Leu Trp Lys Lys
            20

<210> SEQ ID NO 71
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 71

Lys Lys Tyr Leu Ala Ala Gln Leu Asp Leu Cys Leu Lys Arg Gly Asn
1               5                   10                  15

Lys Lys Thr Ala
            20

<210> SEQ ID NO 72
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 72

Thr Lys Lys Asn Gly Arg Lys Leu Cys Leu Asp Leu Gln Ala Ala Leu
1               5                   10                  15

Tyr Lys Lys Lys
            20

<210> SEQ ID NO 73
```

```
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 73

Thr Arg Arg Asn Gly Arg Arg Leu Cys Leu Asp Leu Gln Ala Ala Leu
1               5                   10                  15

Tyr Arg Arg Arg
            20

<210> SEQ ID NO 74
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 74

Thr Lys Lys Asn Gly Lys Lys Leu Cys Leu Asp Leu Gln Ala Ala Leu
1               5                   10                  15

Tyr Lys Lys Lys
            20

<210> SEQ ID NO 75
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 75

Thr Lys Lys Asn Gly Arg Lys Leu Cys Leu Glu Leu Gln Ala Ala Leu
1               5                   10                  15

Tyr Lys Lys Lys
            20

<210> SEQ ID NO 76
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 76

Thr Glu Glu Asn Gly Arg Glu Leu Cys Leu Asp Leu Gln Ala Ala Leu
1               5                   10                  15

Tyr Glu Glu Glu
            20

<210> SEQ ID NO 77
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits
```

<400> SEQUENCE: 77

Thr Lys Lys Asn Gly Arg Lys Leu Cys Leu Lys Leu Gln Ala Ala Leu
1               5                   10                  15

Tyr Lys Lys Lys
            20

<210> SEQ ID NO 78
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 78

Thr Lys Lys Asn Gly Glu Lys Leu Cys Leu Asp Leu Gln Ala Ala Leu
1               5                   10                  15

Tyr Lys Lys Lys
            20

<210> SEQ ID NO 79
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 79

Thr Lys Lys Asn Gly Gly Lys Leu Cys Leu Asp Leu Gln Ala Ala Leu
1               5                   10                  15

Tyr Lys Lys Lys
            20

<210> SEQ ID NO 80
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 80

Thr Lys Lys Asn Gly Arg Lys Leu Cys Leu Gly Leu Gln Ala Ala Leu
1               5                   10                  15

Tyr Lys Lys Lys
            20

<210> SEQ ID NO 81
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 81

Thr Lys Lys Asn Gly Arg Lys Leu Cys Leu Asp Leu Gln Ala Ala Leu
1               5                   10                  15

Phe Lys Lys Lys

```
<210> SEQ ID NO 82
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 82

Thr Lys Lys Asn Gly Arg Lys Leu Cys Leu Asp Leu Gln Ala Ala Leu
1               5                   10                  15

Trp Lys Lys Lys
            20

<210> SEQ ID NO 83
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 83

Lys Lys Tyr Leu Ala Ala Gln Leu Asp Leu Cys Leu Lys Arg Gly Asn
1               5                   10                  15

Lys Lys Thr Ala
            20

<210> SEQ ID NO 84
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 84

Thr Lys Lys Asn Gly Arg Lys Leu Cys Leu Asp Leu Gln Ala Ala Leu
1               5                   10                  15

Tyr Lys Lys

<210> SEQ ID NO 85
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 85

Thr Arg Arg Asn Gly Arg Arg Leu Cys Leu Asp Leu Gln Ala Ala Leu
1               5                   10                  15

Tyr Arg Arg

<210> SEQ ID NO 86
<211> LENGTH: 19
<212> TYPE: PRT
<213> ORGANISM: Artificial Sequence
<220> FEATURE:
<223> OTHER INFORMATION: Antimicrobiocidal peptide designed in part upon
``` microbiocidal domains from platelet microbial
proteins 1 and 2 (PMP-1 and PMP-2) from rabbits

<400> SEQUENCE: 86

Thr Lys Lys Asn Gly Lys Lys Leu Cys Leu Asp Leu Gln Ala Ala Leu
1               5                   10                  15

Tyr Lys Lys

<210> SEQ ID NO 87
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 87

Thr Lys Lys Asn Gly Arg Lys Leu Cys Leu Glu Leu Gln Ala Ala Leu
1               5                   10                  15

Tyr Lys Lys

<210> SEQ ID NO 88
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 88

Thr Glu Glu Asn Gly Arg Glu Leu Cys Leu Asp Leu Gln Ala Ala Leu
1               5                   10                  15

Tyr Glu Glu

<210> SEQ ID NO 89
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 89

Thr Lys Lys Asn Gly Arg Lys Leu Cys Leu Lys Leu Gln Ala Ala Leu
1               5                   10                  15

Tyr Lys Lys

<210> SEQ ID NO 90
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 90

Thr Lys Lys Asn Gly Glu Lys Leu Cys Leu Asp Leu Gln Ala Ala Leu
1               5                   10                  15

Tyr Lys Lys

<210> SEQ ID NO 91
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 91

Thr Lys Lys Asn Gly Gly Lys Leu Cys Leu Asp Leu Gln Ala Ala Leu
 1               5                  10                  15

Tyr Lys Lys

<210> SEQ ID NO 92
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 92

Thr Lys Lys Asn Gly Arg Lys Leu Cys Leu Gly Leu Gln Ala Ala Leu
 1               5                  10                  15

Tyr Lys Lys

<210> SEQ ID NO 93
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 93

Thr Lys Lys Asn Gly Arg Lys Leu Cys Leu Asp Leu Gln Ala Ala Leu
 1               5                  10                  15

Phe Lys Lys

<210> SEQ ID NO 94
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 94

Thr Lys Lys Asn Gly Arg Lys Leu Cys Leu Asp Leu Gln Ala Ala Leu
 1               5                  10                  15

Trp Lys Lys

<210> SEQ ID NO 95
<211> LENGTH: 19
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 95

```
Lys Lys Tyr Leu Ala Ala Gln Leu Asp Leu Cys Leu Lys Arg Gly Asn
1               5                   10                  15

Lys Lys Thr

<210> SEQ ID NO 96
<211> LENGTH: 22
<212> TYPE: PRT
<213> ORGANISM: Oryctolagus cuniculus

<400> SEQUENCE: 96

Ser Asp Asp Pro Lys Glu Ser Glu Gly Asp Leu His Cys Val Cys Val
1               5                   10                  15

Lys Thr Thr Ser Leu Val
            20

<210> SEQ ID NO 97
<211> LENGTH: 37
<212> TYPE: PRT
<213> ORGANISM: Oryctolagus cuniculus

<400> SEQUENCE: 97

Ser Asp Asp Pro Lys Glu Ser Glu Gly Asp Leu His Cys Val Cys Val
1               5                   10                  15

Lys Thr Thr Ser Leu Val Arg Pro Arg His Ile Thr Asn Leu Glu Leu
            20                  25                  30

Ile Lys Ala Gly Gly
        35

<210> SEQ ID NO 98
<211> LENGTH: 22
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 98

Ser Asp Asp Pro Lys Glu Ser Glu Gly Asp Leu His Cys Val Cys Val
1               5                   10                  15

Lys Thr Thr Ser Lys Val
            20

<210> SEQ ID NO 99
<211> LENGTH: 22
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 99

Ser Asp Asp Pro Lys Glu Ser Glu Gly Glu Leu Arg Cys Val Cys Val
1               5                   10                  15

Lys Thr Thr Ser Leu Val
            20

<210> SEQ ID NO 100
<211> LENGTH: 22
<212> TYPE: PRT
<213> ORGANISM: Artificial Sequence
<220> FEATURE:
<223> OTHER INFORMATION: Antimicrobiocidal peptide designed in part upon
``` microbiocidal domains from platelet microbial
proteins 1 and 2 (PMP-1 and PMP-2) from rabbits

<400> SEQUENCE: 100

Ser Asp Asp Pro Lys Glu Ser Glu Gly Glu Leu Arg Cys Val Cys Val
1               5                   10                  15

Lys Thr Thr Ser Lys Val
            20

<210> SEQ ID NO 101
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 101

Ser Asp Asp Pro Lys Glu Ser Glu Gly Asp Leu His Cys Cys Val Lys
1               5                   10                  15

Thr Thr Ser Lys Val
            20

<210> SEQ ID NO 102
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 102

Ser Asp Asp Pro Lys Glu Ser Glu Gly Glu Leu Arg Cys Cys Val Lys
1               5                   10                  15

Thr Thr Ser Leu Val
            20

<210> SEQ ID NO 103
<211> LENGTH: 21
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 103

Ser Asp Asp Pro Lys Glu Ser Glu Gly Glu Leu Arg Cys Cys Val Lys
1               5                   10                  15

Thr Thr Ser Lys Val
            20

<210> SEQ ID NO 104
<211> LENGTH: 40
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 104

Ala Leu Tyr Lys Lys Phe Lys Lys Lys Leu Leu Lys Ser Leu Lys Arg
1               5                   10                  15

```
Leu Gly Ser Asp Asp Pro Lys Glu Ser Glu Gly Asp Leu His Cys Val
            20                  25                  30

Cys Val Lys Thr Thr Ser Leu Val
            35                  40
```

<210> SEQ ID NO 105
<211> LENGTH: 35
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 105

```
Ala Leu Tyr Lys Arg Leu Phe Lys Lys Leu Lys Lys Phe Ser Asp Asp
 1               5                  10                  15

Pro Lys Glu Ser Glu Gly Asp Leu His Cys Val Cys Val Lys Thr Thr
            20                  25                  30

Ser Leu Val
        35
```

<210> SEQ ID NO 106
<211> LENGTH: 40
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 106

```
Ala Leu Thr Lys Lys Phe Lys Lys Leu Leu Lys Ser Leu Lys Arg
 1               5                  10                  15

Leu Gly Ser Asp Asp Pro Lys Glu Ser Glu Gly Glu Leu Arg Cys Val
            20                  25                  30

Cys Val Lys Thr Thr Ser Lys Val
            35                  40
```

<210> SEQ ID NO 107
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 107

```
Glu Trp Val Gln Lys Tyr Val Ser Asn Leu Glu Leu Ser Ala Trp Lys
 1               5                  10                  15

Lys Ile Leu Lys
            20
```

<210> SEQ ID NO 108
<211> LENGTH: 12
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 108

```
Ser Trp Val Gln Glu Tyr Val Tyr Asn Leu Glu Leu
1               5                   10
```

<210> SEQ ID NO 109
<211> LENGTH: 16
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 109

```
Ala Asn Ser Gly Glu Gly Asn Phe Leu Ala Glu Gly Gly Gly Val Arg
1               5                   10                  15
```

<210> SEQ ID NO 110
<211> LENGTH: 20
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 110

```
Ala Asn Ser Gly Glu Gly Asn Phe Leu Ala Glu Gly Gly Gly Val Arg
1               5                   10                  15

Lys Leu Ile Lys
            20
```

<210> SEQ ID NO 111
<211> LENGTH: 18
<212> TYPE: PRT
<213> ORGANISM: Artificial Sequence
<220> FEATURE:
<223> OTHER INFORMATION: Antimicrobiocidal peptide designed in part upon
      microbiocidal domains from platelet microbial
      proteins 1 and 2 (PMP-1 and PMP-2) from rabbits

<400> SEQUENCE: 111

```
Lys Phe Asn Lys Ser Lys Leu Lys Lys Thr Glu Thr Gln Glu Lys Asn
1               5                   10                  15

Pro Leu
```